(12) United States Patent
Moormann et al.

(10) Patent No.: US 6,180,109 B1
(45) Date of Patent: Jan. 30, 2001

(54) NUCLEOTIDE AND POLYPEPTIDE SEQUENCES OF PESTIVIRUS STRAINS

(75) Inventors: Robertus Jacobus Maria Moormann, Dronten; Petrus Antonius Van Rijn, Lelystad, both of (NL)

(73) Assignee: Instituut Voor Dierhouderij en Diergezondheid, Lelystad (NL)

( * ) Notice: Under 35 U.S.C. 154(b), the term of this patent shall be extended for 0 days.

(21) Appl. No.: 08/750,717

(22) PCT Filed: Jun. 16, 1995

(86) PCT No.: PCT/NL95/00214

§ 371 Date: Dec. 24, 1996

§ 102(e) Date: Dec. 24, 1996

(87) PCT Pub. No.: WO95/35380

PCT Pub. Date: Dec. 28, 1995

(30) Foreign Application Priority Data

Jun. 17, 1994 (EP) .................................................. 94201743

(51) Int. Cl.⁷ ............................. A61K 39/12; C07K 1/00; C07K 17/00

(52) U.S. Cl. ........................ 424/204.1; 424/89; 530/350; 530/395; 435/5; 435/7.1

(58) Field of Search ................................. 424/204.1, 89; 530/350, 395; 435/5, 7.1, 7.2

(56) References Cited

U.S. PATENT DOCUMENTS

| | | | |
|---|---|---|---|
| 4,753,884 | * 6/1988 | Kit et al. ............................. | 435/235 |
| 5,122,447 | 6/1992 | McGinley et al. . | |

FOREIGN PATENT DOCUMENTS

| | | | |
|---|---|---|---|
| 0 322 990 | 7/1989 | (EP) . | |
| 0 351 901 | 1/1990 | (EP) . | |
| 0 351 901 | * 1/1991 | (EP) ............................. | A61K/39/187 |
| WO 87/00862 | 2/1987 | (WO) . | |
| WO 91/00352 | 1/1991 | (WO) . | |
| 91/00352 | * 1/1991 | (WO) ............................. | C12N/15/40 |

OTHER PUBLICATIONS

Moorman, et al. : Molecular cloning and nucleotide sequence of Hog Cholera Virus . . . : Vir. : 177: pp. 184–198, 1990.*

Moormann et al., "Molecular cloning and nucleotide sequence of hog cholera virus strain brescia and mapping of the genomic region encoding envelope protein e1", *Virology*, vol. 177, New York, p. 184, No Year.

Muyldermans et al., "Polymerase chain reaction–mediated cloning and in vitro translation of the genes coding for the structural proteins of hog cholera virus", *Archives of Virology*, vol. 132, Vienna, AT, pp. 429–435, No Year.

Vydelingum et al., "Duplicated genes within the variable right end of the genome of a pathogenic isolate of African swine fever virus", *Journal of General Virology*, vol. 74, Colchester, GB, p. 2125, No Year.

* cited by examiner

*Primary Examiner*—Jeffrey Stucker
*Assistant Examiner*—Brett Nelson
(74) *Attorney, Agent, or Firm*—Young & Thompson

(57) ABSTRACT

The invention provides a nucleotide sequence corresponding to a classical swine fever virus (CSFV) genome or a part or a mutant thereof, which comprises at least a part of the nucleotide sequence of the CSFV C-strain depicted in SEQ ID No. 1, or a complement or RNA equivalent of such nucleotide sequence, or which comprises a nucleotide sequence encoding at least the amino acid sequence 268–494 of the amino acid sequence depicted in SEQ ID No. 1, or a complement or RNA equivalent of such nucleotide sequence. Also provided is a pestivirus polypeptide corresponding to the amino acid sequence 690–1063 of SEQ ID No. 1 or part thereof, which contains a mutation in one of the epitopes within amino acid sequences 691–750 or 785–870, said mutation altering said epitope. Further provided is a method of determining the presence of a test substance capable of specifically binding with a binding site of a binding partner, in a sample, by means of competition of said test substance with a measurable amount of a reference substance capable of specifically binding with the same binding site of said binding partner, comprising: (1) contacting said sample with (a) said reference substance bound to a solid carrier, (b) the binding partner of said reference substance, said binding partner molecule containing at least two identical binding sites for said reference substance, and (c) said reference substance provided with a label; (2) measuring the degree of binding of said label to said carrier.

19 Claims, 6 Drawing Sheets

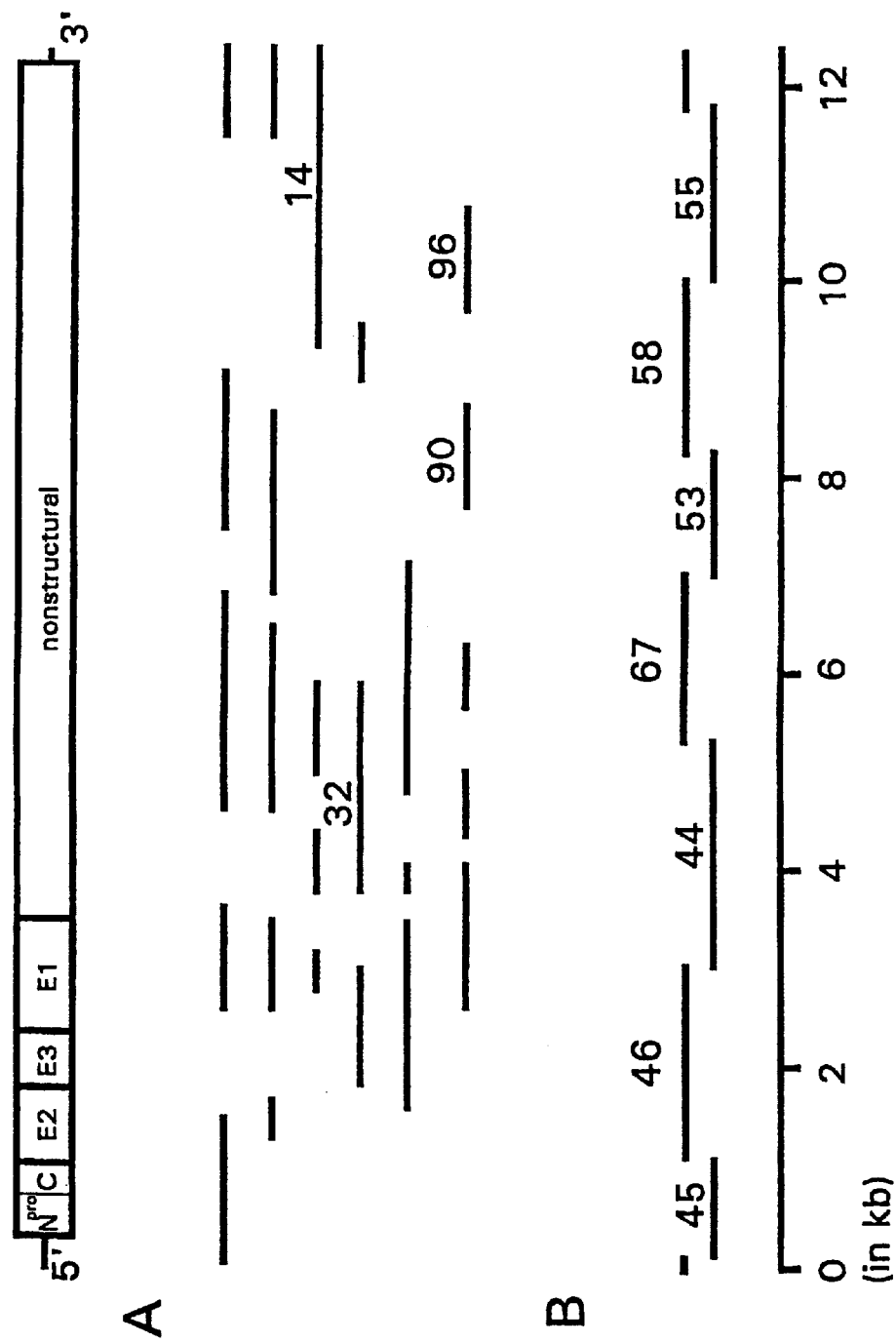

Fig-2A

```
Brescia    GTATACGAGG TTAGTTCATT CTCGTGTACA TGATTGGACA AATCAAAATC
Alfort     .......... ....C..T.. .....A...G AT......T. C.CT...-.T
C-strain   .......... .......... .....A.... C......... .........T Brescia    TCAATTTGGT TCAGGGCCTC CCTCCAGCGA CGGCCGAGCT GGGCTAGCCA
Alfort     ..G....... CT.....AC. .......... .......AA. ..........
C-strain   .T........ .......... .......... .......... ..........

Brescia    TGCCCACAGT AGGACTAGCA AA-CGGAGGG ACTAGCCGTA GTGGCGAGCT
Alfort     ......T... .......... ..-....... .......... ..........
C-strain   ......T... .......... ..A....... .......A.. ..........

Brescia    CCCTGGGTGG TCTAAGTCCT GAGTACAGGA CAGTCGTCAG TAGTTCGACG
Alfort     .......... .......... .......... .......... ..........
C-strain   .......... .......... .......... .......... ..........

Brescia    TGAGCAGAAG CCCACCTCGA GATGCTATGT GGACGAGGGC ATGCCCAAGA
Alfort     ......CT.. .......... .......C.. .......... ..........
C-strain   .......... .......... .......C.. .......... .....-....

Brescia    CACACCTTAA CC-TAGCGGG GGTCGTTAGG GTGAAATCAC ACCATGTGAT
Alfort     .......... ..C.G..... .....C.... .......... .TT.......
C-strain   .......... ..C....... .....C.... .......... ....C.....

Brescia    GGGAGTACGA CCTGATAGGG TGCTGCAGAG GCCCACTATT AGGCTAGTAT
Alfort     ...G...... .......... .......... .......GC .........
C-strain   .......... .......... C......... .......... ..........

Brescia    AAAAATCTCT GCTGTACATG GCACATG
Alfort     .......... .......... ....:..
C-strain   .......... .......... ....:..
```

Fig-2 B

```
Brescia    TGAGTGCGGG TGACCCGCGA TCTGGACCCG TCAGTAGGAC CCTATTGTAG
Alfort     ....CAT..T ..G...TT.. ..G..C..TA .......... .........A
C-strain   ....C..... .A.....G.. ....A..... C......... ..........

Brescia    ATAACACTAA ---------- ----TTTTTT ATTTATTTAG ATATTACTAT
Alfort     ......T... ---------- ---C..-A.. .A........ ...C..T...
C-strain   .......... TTTTCTTTTT TTTC...... .......... ......T...

Brescia    TTATTTATTT ATTTATTTAT TGAATGAGTA AGAACTGGTA CAAACTACCT
Alfort     .......... .......... .......C. ...T...... ..........
C-strain   .......... .......... .......... .......... T.........

Brescia    CATGTTACCA CACTACACTC A-TTTTAACA GCACTTTAGC TGGAAGGAAA
Alfort     .......... .......... .-.C...... .......... ....G.....
C-strain   ..A....... .......... .T........ .......... ..........

Brescia    ATTCCTGACG TCCACAGTTG GACTAAGGTA ATTTC-TAAC GGCCC
Alfort     ..-....... .......... .......... .....C.... ...--
C-strain   .......... .......... .......... .....-.... .....
```

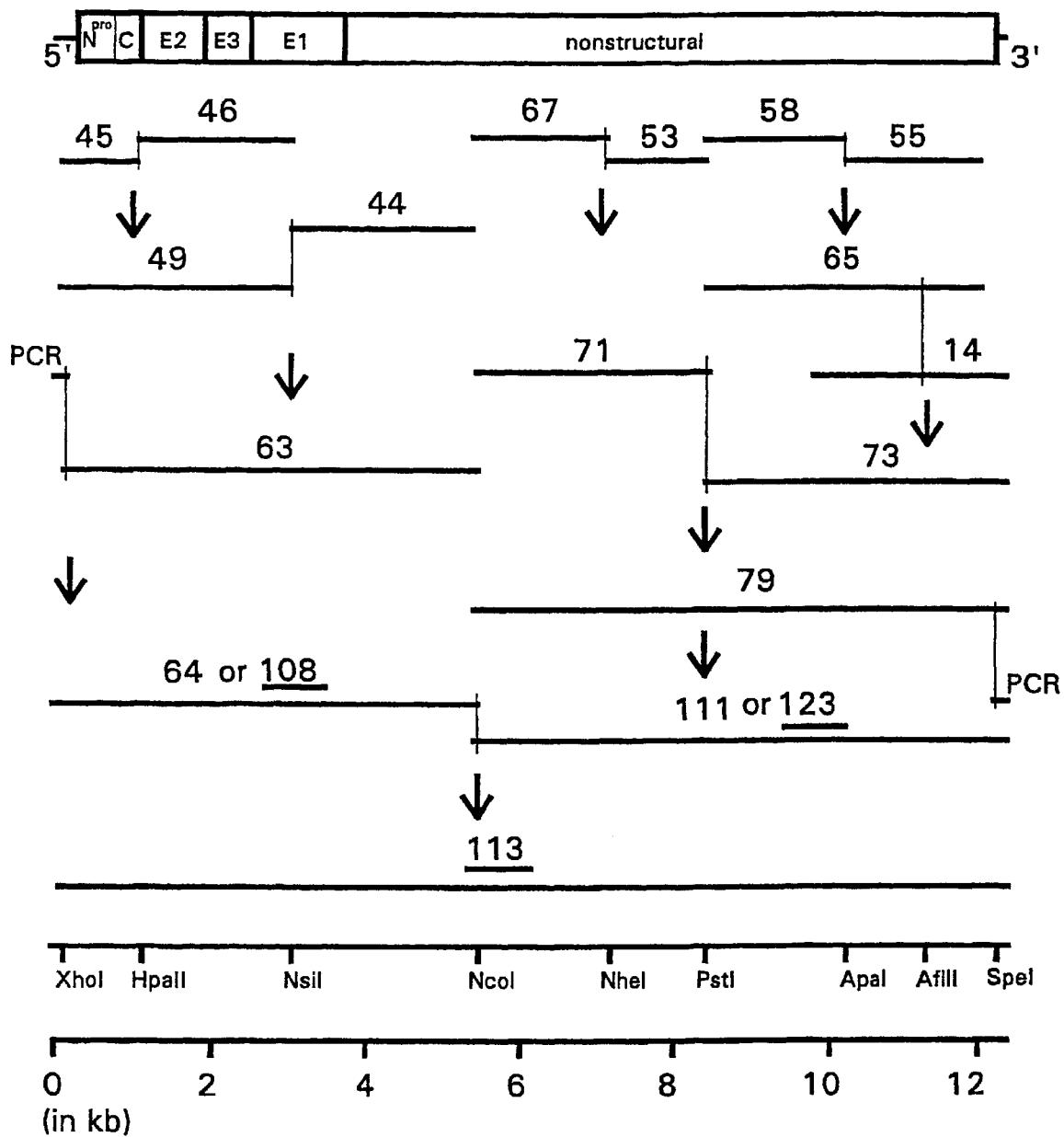

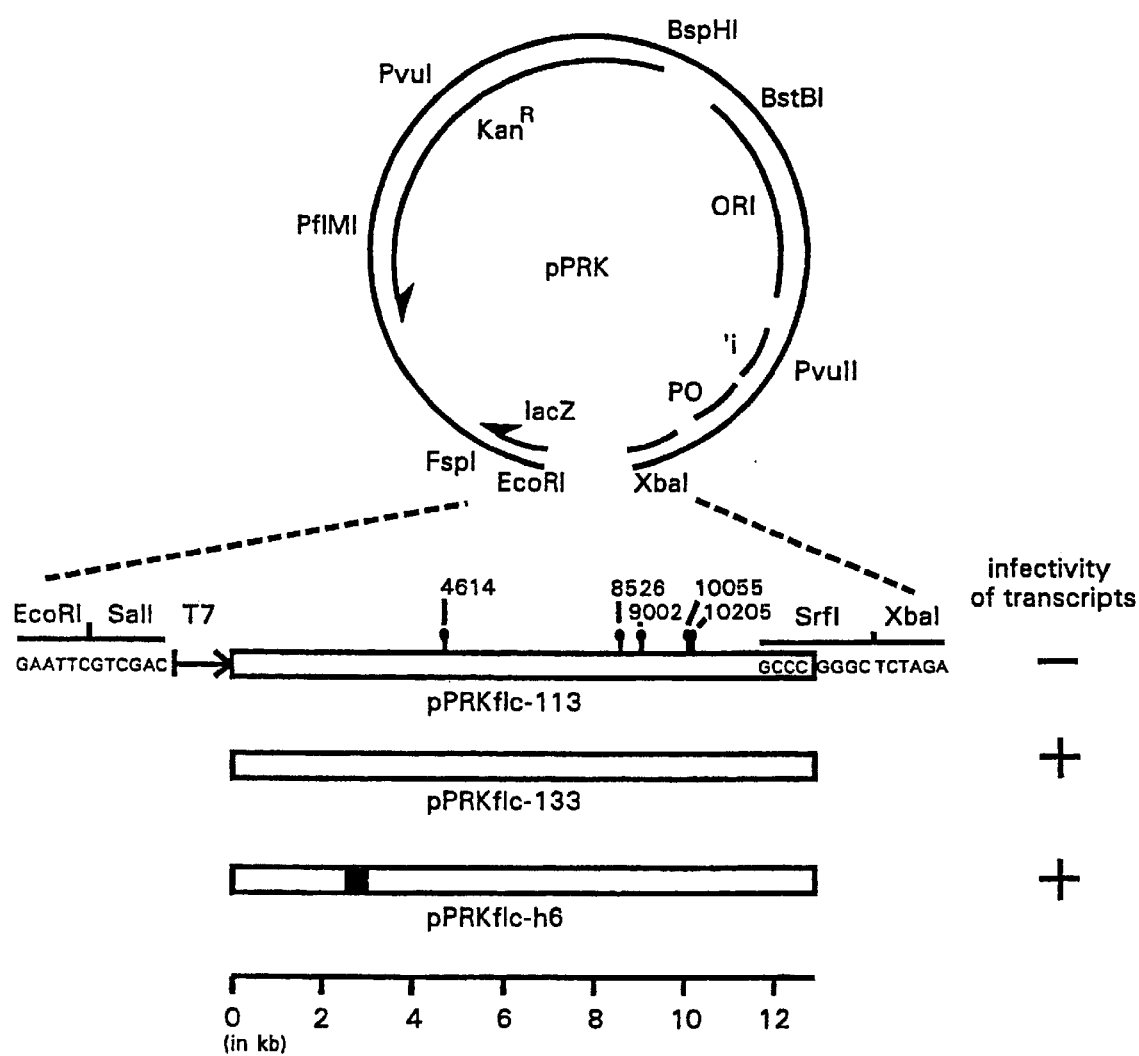

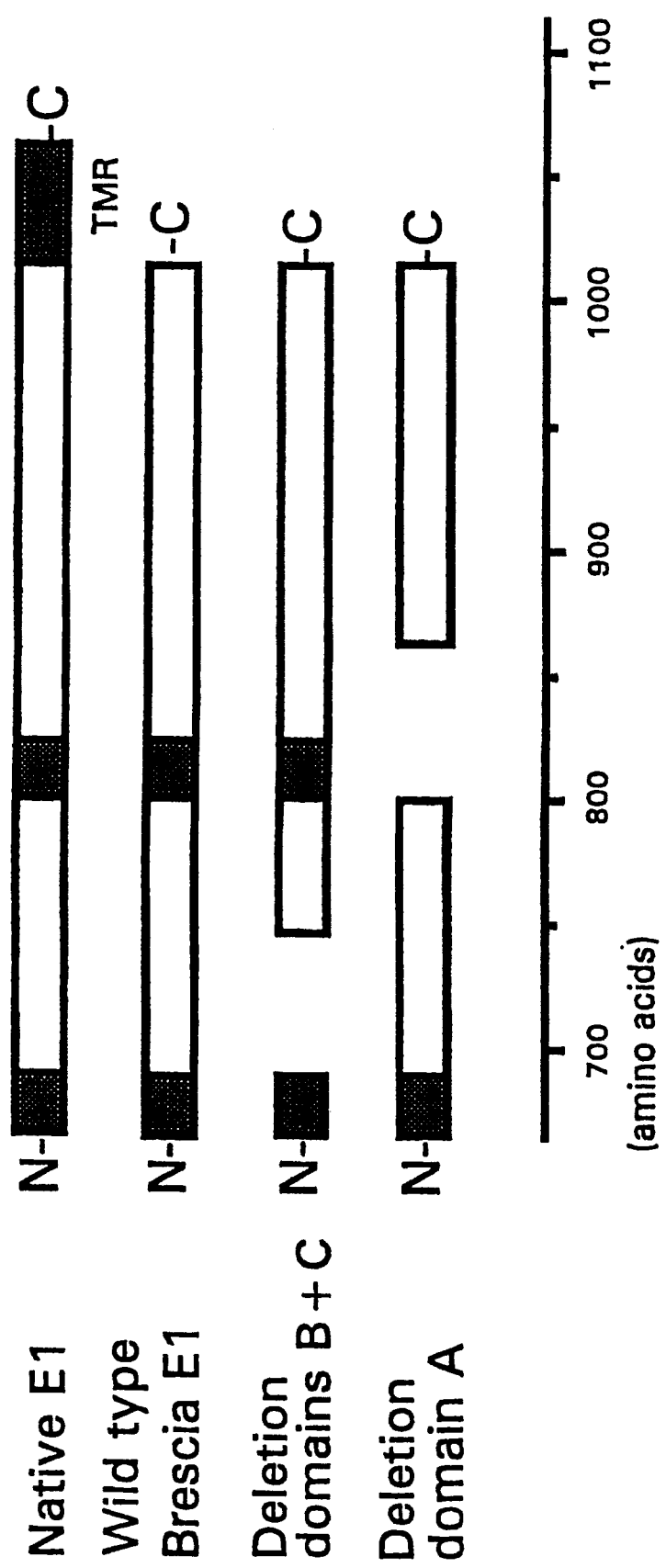

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
      (A) LENGTH: 12311 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 374..12067

(xi) SEQUENCE DESCRIPTION: SEQ ID NO:1:

```
GTATACGAGG TTAGTTCATT CTCGTATACA CGATTGGACA AATCAAAATT ATAATTTGGT      60

TCAGGGCCTC CCTCCAGCGA CGGCCGAACT GGGCTAGCCA TGCCCATAGT AGGACTAGCA     120

AAACGGAGGG ACTAGCCATA GTGGCGAGCT CCCTGGGTGG TCTAAGTCCT GAGTACAGGA     180

CAGTCGTCAG TAGTTCGACG TGAGCAGAAG CCCACCTCGA GATGCTACGT GGACGAGGGC     240

ATGCCAAGAC ACACCTTAAC CCTAGCGGGG GTCGCTAGGG TGAAATCACA CCACGTGATG     300
```

```
GGAGTACGAC CTGATAGGGC GCTGCAGAGG CCCACTATTA GGCTAGTATA AAAATCTCTG      360

CTGTACATGG CAC ATG GAG TTG AAT CAC TTT GAA CTT TTA TAC AAA ACA         409
           Met Glu Leu Asn His Phe Glu Leu Leu Tyr Lys Thr
            1               5                  10

AAC AAA CAA AAA CCA ATG GGA GTG GAG GAA CCG GTG TAC GAT GCC ACG        457
Asn Lys Gln Lys Pro Met Gly Val Glu Glu Pro Val Tyr Asp Ala Thr
            15                  20                  25

GGG AGA CCG TTG TTC GGA GAC CCG AGT GAG GTA CAC CCA CAA TCA ACA        505
Gly Arg Pro Leu Phe Gly Asp Pro Ser Glu Val His Pro Gln Ser Thr
         30                  35                  40

CTG AAG CTA CCA CAT GAT AGG GGT AGA GGC AAC ATT AAA ACA ACA CTG        553
Leu Lys Leu Pro His Asp Arg Gly Arg Gly Asn Ile Lys Thr Thr Leu
 45                  50                  55                  60

AAG AAC CTA CCT AGG AAA GGC GAC TGC AGG AGC GGC AAC CAT CTA GGC        601
Lys Asn Leu Pro Arg Lys Gly Asp Cys Arg Ser Gly Asn His Leu Gly
                 65                  70                  75

CCG GTC AGT GGG ATA TAT GTA AAA CCC GGC CCT GTC TTT TAC CAG GAC        649
Pro Val Ser Gly Ile Tyr Val Lys Pro Gly Pro Val Phe Tyr Gln Asp
             80                  85                  90

TAC ATG GGC CCG GTC TAC CAT AGA GCC CCT CTG GAG TTT TTT GAC GAA        697
Tyr Met Gly Pro Val Tyr His Arg Ala Pro Leu Glu Phe Phe Asp Glu
         95                  100                 105

GTG CAG TTC TGC GAG GTG ACC AAA AGG ATA GGT AGG GTG ACA GGT AGC        745
Val Gln Phe Cys Glu Val Thr Lys Arg Ile Gly Arg Val Thr Gly Ser
     110                 115                 120

GAC GGA AAG CTT TAC CAT ACA TAT GTG TGC ATC GAT GGC TGC ATA CTG        793
Asp Gly Lys Leu Tyr His Thr Tyr Val Cys Ile Asp Gly Cys Ile Leu
125                 130                 135                 140

CTG AAG CTG GCC AAG AGG GGT GAG CCA AGA ACC CTG AAG TGG ATT AGA        841
Leu Lys Leu Ala Lys Arg Gly Glu Pro Arg Thr Leu Lys Trp Ile Arg
                 145                 150                 155

AAT TTC ACC GAC TGT CCA TTG TGG GTT ACC AGT TGC TCC GAT GAT GGC        889
Asn Phe Thr Asp Cys Pro Leu Trp Val Thr Ser Cys Ser Asp Asp Gly
             160                 165                 170

GCA AGT GGG AGT AAA GAG AAG AAG CCA GAT AGG ATC AAC AAA GGC AAA        937
Ala Ser Gly Ser Lys Glu Lys Lys Pro Asp Arg Ile Asn Lys Gly Lys
         175                 180                 185

TTA AAA ATA GCC CCA AAA GAG CAT GAG AAG GAC AGC AGA ACT AGG CCA        985
Leu Lys Ile Ala Pro Lys Glu His Glu Lys Asp Ser Arg Thr Arg Pro
     190                 195                 200

CCT GAC GCT ACG ATC GTG GTG GAA GGA GTA AAA TAC CAG GTC AAA AAG       1033
Pro Asp Ala Thr Ile Val Val Glu Gly Val Lys Tyr Gln Val Lys Lys
205                 210                 215                 220

AAA GGT AAA GTT AAA GGA AAG AAT ACC CAA GAC GGC CTG TAC CAC AAC       1081
Lys Gly Lys Val Lys Gly Lys Asn Thr Gln Asp Gly Leu Tyr His Asn
                 225                 230                 235

AAG AAT AAA CCA CCA GAA TCT AGG AAG AAA CTA GAA AAA GCC CTA TTG       1129
Lys Asn Lys Pro Pro Glu Ser Arg Lys Lys Leu Glu Lys Ala Leu Leu
             240                 245                 250

GCA TGG GCG GTG ATA GCA ATT ATG TTG TAC CAA CCA GTT GAA GCC GAA       1177
Ala Trp Ala Val Ile Ala Ile Met Leu Tyr Gln Pro Val Glu Ala Glu
         255                 260                 265

AAT ATA ACT CAA TGG AAC CTG AGT GAC AAC GGC ACT AAT GGT ATC CAG       1225
Asn Ile Thr Gln Trp Asn Leu Ser Asp Asn Gly Thr Asn Gly Ile Gln
     270                 275                 280

CAT GCT ATG TAC CTT AGA GGG GTT AAC AGA AGC TTG CAT GGG ATC TGG       1273
His Ala Met Tyr Leu Arg Gly Val Asn Arg Ser Leu His Gly Ile Trp
285                 290                 295                 300
```

```
CCG GGG GAA ATA TGC AAA GGA GTC CCA ACC CAC CTG GCC ACA GAC GTG        1321
Pro Gly Glu Ile Cys Lys Gly Val Pro Thr His Leu Ala Thr Asp Val
                305                 310                 315

GAG CTG AAA GAA ATA CAG GGA ATG ATG GAT GCC AGC GAG GGG ACA AAC        1369
Glu Leu Lys Glu Ile Gln Gly Met Met Asp Ala Ser Glu Gly Thr Asn
            320                 325                 330

TAT ACG TGC TGT AAG TTA CAG AGA CAT GAA TGG AAC AAA CAT GGA TGG        1417
Tyr Thr Cys Cys Lys Leu Gln Arg His Glu Trp Asn Lys His Gly Trp
                335                 340                 345

TGT AAC TGG CAC AAT ATA GAC CCC TGG ATA CAG CTG ATG AAT AGA ACC        1465
Cys Asn Trp His Asn Ile Asp Pro Trp Ile Gln Leu Met Asn Arg Thr
350                 355                 360

CAA GCA GAC TTG GCA GAA GGC CCT CCG GTC AAG GAG TGC GCT GTG ACT        1513
Gln Ala Asp Leu Ala Glu Gly Pro Pro Val Lys Glu Cys Ala Val Thr
365                 370                 375                 380

TGC AGG TAC GAT AAA GAT GCT GAC ATC AAC GTG GTT ACC CAG GCT AGA        1561
Cys Arg Tyr Asp Lys Asp Ala Asp Ile Asn Val Val Thr Gln Ala Arg
                385                 390                 395

AAC AGG CCA ACA ACC CTG ACC GGC TGC AAG AAA GGG AAA AAT TTT TCT        1609
Asn Arg Pro Thr Thr Leu Thr Gly Cys Lys Lys Gly Lys Asn Phe Ser
            400                 405                 410

TTT GCG GGT ACA GTT ATA GAG AGC CCA TGT AAT TTC AAT GTT TCC GTG        1657
Phe Ala Gly Thr Val Ile Glu Ser Pro Cys Asn Phe Asn Val Ser Val
                415                 420                 425

GAG GAT ACC TTG TAT GGG GAT CAT GAG TGC GGC AGT TTG CTC CAG GAC        1705
Glu Asp Thr Leu Tyr Gly Asp His Glu Cys Gly Ser Leu Leu Gln Asp
            430                 435                 440

GCA GCT CTG TAC CTA GTA GAT GGA ATG ACC AAC ACT ATA GAG AAT GCC        1753
Ala Ala Leu Tyr Leu Val Asp Gly Met Thr Asn Thr Ile Glu Asn Ala
445                 450                 455                 460

AGA CAG GGA GCA GCG AGG GTG ACA TCC TGG CTC GGG AGG CAA CTC AGA        1801
Arg Gln Gly Ala Ala Arg Val Thr Ser Trp Leu Gly Arg Gln Leu Arg
                465                 470                 475

ACT GCT GGG AAG AGG TTG GAG GGT AGA AGC AAA ACC TGG TTT GGC GCT        1849
Thr Ala Gly Lys Arg Leu Glu Gly Arg Ser Lys Thr Trp Phe Gly Ala
            480                 485                 490

TAT GCC CTA TCG CCT TAC TGT AAT GTA ACA AGC AAA ATA GGG TAC ATA        1897
Tyr Ala Leu Ser Pro Tyr Cys Asn Val Thr Ser Lys Ile Gly Tyr Ile
                495                 500                 505

TGG TAC ACT AAC AAC TGC ACC CCA GCT TGC CTC CCC AAA AAC ACA AAG        1945
Trp Tyr Thr Asn Asn Cys Thr Pro Ala Cys Leu Pro Lys Asn Thr Lys
510                 515                 520

ATA ATA GGC CCT GGT AAA TTT GAC ACT AAT GCA GAA GAC GGA AAG ATT        1993
Ile Ile Gly Pro Gly Lys Phe Asp Thr Asn Ala Glu Asp Gly Lys Ile
525                 530                 535                 540

CTC CAT GAG ATG GGG GGC CAC CTA TCA GAA TTT CTG CTG CTT TCT CTG        2041
Leu His Glu Met Gly Gly His Leu Ser Glu Phe Leu Leu Leu Ser Leu
                545                 550                 555

GTT GTT CTG TCT GAC TTC GCC CCT GAA ACA GCC AGC GCG TTA TAC CTC        2089
Val Val Leu Ser Asp Phe Ala Pro Glu Thr Ala Ser Ala Leu Tyr Leu
            560                 565                 570

ATT TTG CAC TAC GTG ATT CCT CAA CCC CAT GAT GAA CCT GAA GGC TGC        2137
Ile Leu His Tyr Val Ile Pro Gln Pro His Asp Glu Pro Glu Gly Cys
                575                 580                 585

GAT ACG AAC CAG CTG AAT CTA ACA GTA GAA CTC AGG ACT GAA GAC GTA        2185
Asp Thr Asn Gln Leu Asn Leu Thr Val Glu Leu Arg Thr Glu Asp Val
            590                 595                 600

ATA CCG TCA TCA GTC TGG AAT GTT GGT AAA TAT GTG TGT GTT AGA CCA        2233
Ile Pro Ser Ser Val Trp Asn Val Gly Lys Tyr Val Cys Val Arg Pro
605                 610                 615                 620
```

```
GAC TGG TGG CCA TAT GAA ACC GAG GTG GCT CTG TTA TTT GAA GAG GTA    2281
Asp Trp Trp Pro Tyr Glu Thr Glu Val Ala Leu Leu Phe Glu Glu Val
                625                 630                 635

GGA CAG GTC GTA AAG TTA GCC TTA CGG GCG CTG AGG GAT TTG ACT AGG    2329
Gly Gln Val Val Lys Leu Ala Leu Arg Ala Leu Arg Asp Leu Thr Arg
                640                 645                 650

GTC TGG AAT AGC GCA TCA ACC ATT GCA TTC CTC ATC TGC TTG ATA AAA    2377
Val Trp Asn Ser Ala Ser Thr Ile Ala Phe Leu Ile Cys Leu Ile Lys
                655                 660                 665

GTA TTA AGA GGA CAG ATC GTG CAA GGT GTG GTA TGG CTG TTA CTA GTA    2425
Val Leu Arg Gly Gln Ile Val Gln Gly Val Val Trp Leu Leu Leu Val
                670                 675                 680

ACT GGG GCA CAA GGC CGG CTA GCC TGC AAG GAA GAT TAC AGG TAC GCA    2473
Thr Gly Ala Gln Gly Arg Leu Ala Cys Lys Glu Asp Tyr Arg Tyr Ala
685                 690                 695                 700

ATA TCG TCA ACC GAT GAG ATA GGG CTA CTT GGG GCC GGA GGT CTC ACC    2521
Ile Ser Ser Thr Asp Glu Ile Gly Leu Leu Gly Ala Gly Gly Leu Thr
                705                 710                 715

ACC ACC TGG AAG GAA TAC AAC CAC GAT TTG CAA CTG AAT GAC GGG ACC    2569
Thr Thr Trp Lys Glu Tyr Asn His Asp Leu Gln Leu Asn Asp Gly Thr
                720                 725                 730

GTT AAG GCC AGT TGC GTG GCA GGT TCC TTT AAA GTC ACA GCA CTT AAT    2617
Val Lys Ala Ser Cys Val Ala Gly Ser Phe Lys Val Thr Ala Leu Asn
                735                 740                 745

GTG GTC AGT AGG AGG TAT TTG GCA TCA TTG CAT AAG AAG GCT TTA CCC    2665
Val Val Ser Arg Arg Tyr Leu Ala Ser Leu His Lys Lys Ala Leu Pro
                750                 755                 760

ACT TCC GTG ACA TTC GAG CTC CTG TTC GAC GGG ACC AAC CCA TCA ACT    2713
Thr Ser Val Thr Phe Glu Leu Leu Phe Asp Gly Thr Asn Pro Ser Thr
765                 770                 775                 780

GAG GAA ATG GGA GAT GAC TTC AGG TCC GGG CTG TGC CCG TTT GAT ACG    2761
Glu Glu Met Gly Asp Asp Phe Arg Ser Gly Leu Cys Pro Phe Asp Thr
                785                 790                 795

AGT CCT GTT GTT AAG GGA AAG TAC AAT ACG ACC TTG TTG AAC GGT AGT    2809
Ser Pro Val Val Lys Gly Lys Tyr Asn Thr Thr Leu Leu Asn Gly Ser
                800                 805                 810

GCT TTC TAT CTT GTC TGC CCA ATA GGG TGG ACG GGT GTC ATA GAG TGC    2857
Ala Phe Tyr Leu Val Cys Pro Ile Gly Trp Thr Gly Val Ile Glu Cys
                815                 820                 825

ACA GCA GTG AGC CCA ACA ACT CTG AGA ACA GAA GTG GTA AAG ACC TTC    2905
Thr Ala Val Ser Pro Thr Thr Leu Arg Thr Glu Val Val Lys Thr Phe
830                 835                 840

AGG AGA GAC AAG CCC TTT CCG CAC AGA ATG GAT TGT GTG ACC ACC ACA    2953
Arg Arg Asp Lys Pro Phe Pro His Arg Met Asp Cys Val Thr Thr Thr
845                 850                 855                 860

GTG GAA AAT GAA GAT TTA TTC TAT TGT AAG TTG GGG GGC AAC TGG ACA    3001
Val Glu Asn Glu Asp Leu Phe Tyr Cys Lys Leu Gly Gly Asn Trp Thr
                865                 870                 875

TGT GTG AAA GGC GAG CCA GTG GTC TAC ACA GGG GGG CTA GTA AAA CAA    3049
Cys Val Lys Gly Glu Pro Val Val Tyr Thr Gly Gly Leu Val Lys Gln
                880                 885                 890

TGT AGA TGG TGT GGC TTC GAC TTC GAT GGG CCT GAC GGA CTC CCG CAT    3097
Cys Arg Trp Cys Gly Phe Asp Phe Asp Gly Pro Asp Gly Leu Pro His
                895                 900                 905

TAC CCC ATA GGT AAG TGC ATT TTG GCA AAT GAG ACA GGT TAC AGA ATA    3145
Tyr Pro Ile Gly Lys Cys Ile Leu Ala Asn Glu Thr Gly Tyr Arg Ile
                910                 915                 920

GTA GAT TCA ACG GAC TGT AAC AGA GAT GGC GTT GTA ATC AGC ACA GAG    3193
Val Asp Ser Thr Asp Cys Asn Arg Asp Gly Val Val Ile Ser Thr Glu
```

```
                925              930              935              940
GGG AGT CAT GAG TGC TTG ATC GGT AAC ACG ACT GTC AAG GTG CAT GCA              3241
Gly Ser His Glu Cys Leu Ile Gly Asn Thr Thr Val Lys Val His Ala
                945              950              955

TCA GAT GAA AGA TTG GGC CCT ATG CCA TGC AGA CCT AAA GAG ATT GTC              3289
Ser Asp Glu Arg Leu Gly Pro Met Pro Cys Arg Pro Lys Glu Ile Val
            960              965              970

TCT AGT GCT GGA CCT GTA AAG AAA ACC TCC TGT ACA TTC AAC TAC ACA              3337
Ser Ser Ala Gly Pro Val Lys Lys Thr Ser Cys Thr Phe Asn Tyr Thr
        975              980              985

AAA ACT TTG AAG AAC AGG TAC TAT GAG CCC AGG GAC AGC TAC TTC CAG              3385
Lys Thr Leu Lys Asn Arg Tyr Tyr Glu Pro Arg Asp Ser Tyr Phe Gln
    990              995              1000

CAA TAT ATG CTT AAG GGT GAG TAT CAG TAC TGG TTT GAC CTG GAT GCG              3433
Gln Tyr Met Leu Lys Gly Glu Tyr Gln Tyr Trp Phe Asp Leu Asp Ala
1005             1010             1015             1020

ACT GAC CGC CAC TCA GAT TAC TTC GCA GAA TTT GTT GTC TTG GTG GTG              3481
Thr Asp Arg His Ser Asp Tyr Phe Ala Glu Phe Val Val Leu Val Val
            1025             1030             1035

GTA GCA CTG TTA GGA GGA AGA TAT GTC CTG TGG CTG ATA GTG ACC TAC              3529
Val Ala Leu Leu Gly Gly Arg Tyr Val Leu Trp Leu Ile Val Thr Tyr
        1040             1045             1050

GTA GTT CTA ACA GAA CAA CTC GCC GCT GGT TTA CCA TTG GGC CAG GGT              3577
Val Val Leu Thr Glu Gln Leu Ala Ala Gly Leu Pro Leu Gly Gln Gly
    1055             1060             1065

GAG GTA GTG TTG ATA GGG AAC TTA ATT ACC CAT ACA GAC ATT GAG GTC              3625
Glu Val Val Leu Ile Gly Asn Leu Ile Thr His Thr Asp Ile Glu Val
1070             1075             1080

GTA GTA TAT TTT TTA CTA CTC TAT TTG GTC ATG AGG GAT GAA CCT ATA              3673
Val Val Tyr Phe Leu Leu Leu Tyr Leu Val Met Arg Asp Glu Pro Ile
1085             1090             1095             1100

AAG AAA TGG ATA CTG CTG CTG TTC CAT GCT ATG ACT AAC AAT CCA GTC              3721
Lys Lys Trp Ile Leu Leu Leu Phe His Ala Met Thr Asn Asn Pro Val
            1105             1110             1115

AAG ACC ATA ACA GTG GCA TTG CTC ATG GTT AGT GGA GTT GCC AAG GGT              3769
Lys Thr Ile Thr Val Ala Leu Leu Met Val Ser Gly Val Ala Lys Gly
        1120             1125             1130

GGA AAG ATA GAT GGC GGT TGG CAG CGA CTG CCG GGG ACC AGC TTT GAC              3817
Gly Lys Ile Asp Gly Gly Trp Gln Arg Leu Pro Gly Thr Ser Phe Asp
    1135             1140             1145

ATC CAA CTC GCG CTG ACA GTT ATA GTA GTC GCT GTG ATG TTG CTG GCA              3865
Ile Gln Leu Ala Leu Thr Val Ile Val Val Ala Val Met Leu Leu Ala
1150             1155             1160

AAG AGA GAT CCG ACT ACT GTC CCC TTG GTT ATA ACA GTG GCA CCC CTG              3913
Lys Arg Asp Pro Thr Thr Val Pro Leu Val Ile Thr Val Ala Pro Leu
1165             1170             1175             1180

AGG ACA GCT AAG ATG ACT AAC GGA CTT AGT ACG GAT ATA GCC ATA GCC              3961
Arg Thr Ala Lys Met Thr Asn Gly Leu Ser Thr Asp Ile Ala Ile Ala
            1185             1190             1195

ACA GTG TCA GCA GCG TTG CTA ACC TGG ACC TAC ATT AGT GAC TAT TAC              4009
Thr Val Ser Ala Ala Leu Leu Thr Trp Thr Tyr Ile Ser Asp Tyr Tyr
        1200             1205             1210

AGA TAC AAG ACC TGG CTA CAG TAC CTT ATC AGC ACA GTG ACA GGT ATC              4057
Arg Tyr Lys Thr Trp Leu Gln Tyr Leu Ile Ser Thr Val Thr Gly Ile
    1215             1220             1225

TTT TTA ATA AGG GTA CTG AAG GGA ATA GGT GAG TTG GAT TTA CAC ACT              4105
Phe Leu Ile Arg Val Leu Lys Gly Ile Gly Glu Leu Asp Leu His Thr
1230             1235             1240

CCG ACC TTG CCA TCT CAT AGA CCC CTC TTT TTC ATT CTC GTG TAC CTT              4153
```

```
Pro Thr Leu Pro Ser His Arg Pro Leu Phe Phe Ile Leu Val Tyr Leu
1245                1250                1255                1260

ATT TCC ACT GCA GTG GTA ACA AGA TGG AAT CTG GAC ATA GCC GGA TTG         4201
Ile Ser Thr Ala Val Val Thr Arg Trp Asn Leu Asp Ile Ala Gly Leu
                1265                1270                1275

CTG TTG CAG TGT GTC CCA ACC CTT TTG ATG GTT TTT ACG ATG TGG GCA         4249
Leu Leu Gln Cys Val Pro Thr Leu Leu Met Val Phe Thr Met Trp Ala
                1280                1285                1290

GAC ATT CTC ACC CTG ATC CTC ATA CTG CCC ACT TAC GAG TTA ACG AAG         4297
Asp Ile Leu Thr Leu Ile Leu Ile Leu Pro Thr Tyr Glu Leu Thr Lys
                1295                1300                1305

CTA TAT TAT CTT AAG GAA GTG AGG ATT GGG GCA GAA AAG GGC TGG TTA         4345
Leu Tyr Tyr Leu Lys Glu Val Arg Ile Gly Ala Glu Lys Gly Trp Leu
                1310                1315                1320

TGG AAA ACC AAC TTC AAG AGG GTA AAC GAC ATA TAC GAA GTT GAC CAA         4393
Trp Lys Thr Asn Phe Lys Arg Val Asn Asp Ile Tyr Glu Val Asp Gln
1325                1330                1335                1340

GCT GGT GAA GGG GTA TAC CTA TTC CCG TCA AAA CAA AAG ACA AGT TCA         4441
Ala Gly Glu Gly Val Tyr Leu Phe Pro Ser Lys Gln Lys Thr Ser Ser
                1345                1350                1355

ATG ACA GGC ACC ATG TTG CCA TTG ATC AAA GCC ATA CTT ATC AGC TGC         4489
Met Thr Gly Thr Met Leu Pro Leu Ile Lys Ala Ile Leu Ile Ser Cys
                1360                1365                1370

GTC AGT AAT AAG TGG CAG TTC ATA TAT CTA CTG TAC TTG ATA TTT GAA         4537
Val Ser Asn Lys Trp Gln Phe Ile Tyr Leu Leu Tyr Leu Ile Phe Glu
                1375                1380                1385

GTA TCT TAC TAC CTC CAC AAG AAG ATC ATA GAT GAA ATA GCA GGA GGG         4585
Val Ser Tyr Tyr Leu His Lys Lys Ile Ile Asp Glu Ile Ala Gly Gly
                1390                1395                1400

ACC AAC TTC ATC TCA AGA CTT GTA GCC GCT TTG ATC GAA GTC AAT TGG         4633
Thr Asn Phe Ile Ser Arg Leu Val Ala Ala Leu Ile Glu Val Asn Trp
1405                1410                1415                1420

GCC TTT GAC AAC GAA GAA GTT AGG GGT TTG AAG AAG TTC TTC CTG TTG         4681
Ala Phe Asp Asn Glu Glu Val Arg Gly Leu Lys Lys Phe Phe Leu Leu
                1425                1430                1435

TCT AGT AGG GTT AAA GAA CTG ATC ATC AAA CAC AAA GTG AGG AAT GAA         4729
Ser Ser Arg Val Lys Glu Leu Ile Ile Lys His Lys Val Arg Asn Glu
                1440                1445                1450

GTA ATG GTC CGC TGG TTT GGT GAC GAA GAG GTC TAT GGG ATG CCG AAG         4777
Val Met Val Arg Trp Phe Gly Asp Glu Glu Val Tyr Gly Met Pro Lys
                1455                1460                1465

TTG GTT GGC CTA GTC AAG GCA GCA ACA TTG AGT AAA AAT AAA CAT TGT         4825
Leu Val Gly Leu Val Lys Ala Ala Thr Leu Ser Lys Asn Lys His Cys
                1470                1475                1480

ATT TTG TGC ACC GTC TGT GAA GAC AGA GAG TGG AGA GGA GAA ACC TGC         4873
Ile Leu Cys Thr Val Cys Glu Asp Arg Glu Trp Arg Gly Glu Thr Cys
1485                1490                1495                1500

CCA AAA TGC GGG CGT TTT GGG CCA CCA ATG ACC TGT GGC ATG ACC CTA         4921
Pro Lys Cys Gly Arg Phe Gly Pro Pro Met Thr Cys Gly Met Thr Leu
                1505                1510                1515

GCC GAC TTT GAA GAG AAA CAC TAT AAG AGG ATC TTT TTT AGA GAG GAT         4969
Ala Asp Phe Glu Glu Lys His Tyr Lys Arg Ile Phe Phe Arg Glu Asp
                1520                1525                1530

CAA TCA GAA GGG CCG GTT AGG GAG GAG TAC GCA GGG TAT CTG CAA TAT         5017
Gln Ser Glu Gly Pro Val Arg Glu Glu Tyr Ala Gly Tyr Leu Gln Tyr
                1535                1540                1545

AGA GCC AGA GGG CAA TTG TTC CTG AGG AAT CTC CCA GTG CTA GCA ACA         5065
Arg Ala Arg Gly Gln Leu Phe Leu Arg Asn Leu Pro Val Leu Ala Thr
                1550                1555                1560
```

```
AAA GTC AAG ATG CTC CTG GTC GGC AAT CTT GGG ACG GAG GTG GGA GAT      5113
Lys Val Lys Met Leu Leu Val Gly Asn Leu Gly Thr Glu Val Gly Asp
1565                1570                1575                1580

TTG GAA CAC CTT GGC TGG GTG CTT AGA GGG CCT GCC GTT TGC AAG AAG      5161
Leu Glu His Leu Gly Trp Val Leu Arg Gly Pro Ala Val Cys Lys Lys
                1585                1590                1595

GTC ACT GAA CAT GAG AAA TGT ACC ACA TCC ATG ATG GAC AAA TTG ACT      5209
Val Thr Glu His Glu Lys Cys Thr Thr Ser Met Met Asp Lys Leu Thr
    1600                1605                1610

GCT TTT TTC GGT GTT ATG CCG AGG GGC ACC ACA CCT AGA GCC CCT GTG      5257
Ala Phe Phe Gly Val Met Pro Arg Gly Thr Thr Pro Arg Ala Pro Val
        1615                1620                1625

AGA TTC CCT ACC TCT CTC TTA AAG ATA AGA AGG GGT TTG GAA ACT GGC      5305
Arg Phe Pro Thr Ser Leu Leu Lys Ile Arg Arg Gly Leu Glu Thr Gly
            1630                1635                1640

TGG GCG TAC ACA CAC CAA GGT GGC ATC AGT TCA GTG GAC CAT GTC ACT      5353
Trp Ala Tyr Thr His Gln Gly Gly Ile Ser Ser Val Asp His Val Thr
1645                1650                1655                1660

TGT GGA AAA GAC TTA CTG GTA TGT GAC ACT ATG GGC CGG ACA AGG GTT      5401
Cys Gly Lys Asp Leu Leu Val Cys Asp Thr Met Gly Arg Thr Arg Val
                1665                1670                1675

GTT TGC CAG TCA AAT AAT AAG ATG ACA GAT GAG TCC GAG TAT GGA GTT      5449
Val Cys Gln Ser Asn Asn Lys Met Thr Asp Glu Ser Glu Tyr Gly Val
    1680                1685                1690

AAA ACT GAC TCC GGA TGC CCG GAA GGA GCT AGG TGT TAT GTG TTT AAC      5497
Lys Thr Asp Ser Gly Cys Pro Glu Gly Ala Arg Cys Tyr Val Phe Asn
        1695                1700                1705

CCA GAG GCG GTT AAC ATA TCA GGG ACT AAA GGA GCC ATG GTC CAC TTA      5545
Pro Glu Ala Val Asn Ile Ser Gly Thr Lys Gly Ala Met Val His Leu
            1710                1715                1720

CAA AAA ACT GGA GGA GAA TTC ACC TGT GTG ACA GCA TCA GGA ACT CCG      5593
Gln Lys Thr Gly Gly Glu Phe Thr Cys Val Thr Ala Ser Gly Thr Pro
1725                1730                1735                1740

GCT TTC TTT GAT CTT AAA AAC CTT AAA GGC TGG TCA GGG CTA CCG ATA      5641
Ala Phe Phe Asp Leu Lys Asn Leu Lys Gly Trp Ser Gly Leu Pro Ile
                1745                1750                1755

TTT GAG GCA TCA AGT GGA AGG GTA GTC GGC AGG GTC AAG GTC GGT AAG      5689
Phe Glu Ala Ser Ser Gly Arg Val Val Gly Arg Val Lys Val Gly Lys
    1760                1765                1770

AAT GAG GAC TCT AAA CCA ACC AAG CTT ATG AGT GGA ATA CAA ACA GTT      5737
Asn Glu Asp Ser Lys Pro Thr Lys Leu Met Ser Gly Ile Gln Thr Val
        1775                1780                1785

TCC AAA AGT ACC ACA GAC TTG ACA GAA ATG GTA AAG AAA ATA ACT ACC      5785
Ser Lys Ser Thr Thr Asp Leu Thr Glu Met Val Lys Lys Ile Thr Thr
            1790                1795                1800

ATG AGC AGG GGA GAA TTC AGA CAA ATA ACC CTT GCT ACA GGT GCC GGA      5833
Met Ser Arg Gly Glu Phe Arg Gln Ile Thr Leu Ala Thr Gly Ala Gly
1805                1810                1815                1820

AAA ACC ACG GAA CTC CCT AGG TCA GTC ATA GAA GAG ATA GGG AGG CAT      5881
Lys Thr Thr Glu Leu Pro Arg Ser Val Ile Glu Glu Ile Gly Arg His
                1825                1830                1835

AAG AGA GTC TTG GTC TTG ATT CCT CTG AGG GCG GCA GCA GAG TCA GTA      5929
Lys Arg Val Leu Val Leu Ile Pro Leu Arg Ala Ala Ala Glu Ser Val
    1840                1845                1850

TAC CAA TAT ATG AGA CAA AAA CAT CCA AGC ATC GCA TTT AAC CTG AGG      5977
Tyr Gln Tyr Met Arg Gln Lys His Pro Ser Ile Ala Phe Asn Leu Arg
        1855                1860                1865

ATA GGG GAG ATG AAG GAA GGG GAC ATG GCC ACA GGG ATA ACT TAT GCT      6025
Ile Gly Glu Met Lys Glu Gly Asp Met Ala Thr Gly Ile Thr Tyr Ala
            1870                1875                1880
```

```
TCA TAC GGT TAC TTC TGT CAG ATG CCA CAA CCT AAG TTG CGA GCC GCA      6073
Ser Tyr Gly Tyr Phe Cys Gln Met Pro Gln Pro Lys Leu Arg Ala Ala
1885                1890                1895                1900

ATG GTT GAG TAC TCC TTC ATA TTT CTT GAT GAG TAC CAC TGT GCC ACC      6121
Met Val Glu Tyr Ser Phe Ile Phe Leu Asp Glu Tyr His Cys Ala Thr
                1905                1910                1915

CCT GAA CAA TTG GCT ATC ATG GGA AAG ATT CAC AGA TTT TCA GAG AAC      6169
Pro Glu Gln Leu Ala Ile Met Gly Lys Ile His Arg Phe Ser Glu Asn
            1920                1925                1930

CTG CGG GTG GTG GCC ATG ACC GCA ACA CCA GTA GGC ACG GTA ACG ACC      6217
Leu Arg Val Val Ala Met Thr Ala Thr Pro Val Gly Thr Val Thr Thr
        1935                1940                1945

ACA GGG CAG AAA CAC CCT ATA GAA GAA TTC ATA GCC CCA GAT GTG ATG      6265
Thr Gly Gln Lys His Pro Ile Glu Glu Phe Ile Ala Pro Asp Val Met
1950                1955                1960

AAA GGG AAA GAC TTA GGT TCA GAG TAC TTG GAC ATT GCT GGA TTA AAG      6313
Lys Gly Lys Asp Leu Gly Ser Glu Tyr Leu Asp Ile Ala Gly Leu Lys
1965                1970                1975                1980

ATA CCA GTA GAG GAG ATG AAG AGC AAT ATG CTG GTT TTT GTG CCC ACC      6361
Ile Pro Val Glu Glu Met Lys Ser Asn Met Leu Val Phe Val Pro Thr
                1985                1990                1995

AGG AAC ATG GCA GTG GAG ACA GCA AAG AAA TTG AAA GCT AAG GGT TAT      6409
Arg Asn Met Ala Val Glu Thr Ala Lys Lys Leu Lys Ala Lys Gly Tyr
            2000                2005                2010

AAC TCA GGC TAC TAT TAT AGT GGT GAG GAT CCA TCT AAC CTG AGG GTG      6457
Asn Ser Gly Tyr Tyr Tyr Ser Gly Glu Asp Pro Ser Asn Leu Arg Val
        2015                2020                2025

GTA ACA TCG CAG TCC CCG TAC GTG GTG GTG GCA ACC AAC GCG ATA GAA      6505
Val Thr Ser Gln Ser Pro Tyr Val Val Val Ala Thr Asn Ala Ile Glu
2030                2035                2040

TCA GGT GTT ACT CTC CCG GAC TTG GAT GTG GTT GTC GAT ACA GGG CTT      6553
Ser Gly Val Thr Leu Pro Asp Leu Asp Val Val Val Asp Thr Gly Leu
2045                2050                2055                2060

AAG TGT GAA AAG AGA ATA CGG CTG TCA CCT AAG ATG CCC TTC ATA GTG      6601
Lys Cys Glu Lys Arg Ile Arg Leu Ser Pro Lys Met Pro Phe Ile Val
                2065                2070                2075

ACG GGC CTG AAG AGA ATG GCT GTC ACG ATT GGG GAA CAA GCC CAG AGA      6649
Thr Gly Leu Lys Arg Met Ala Val Thr Ile Gly Glu Gln Ala Gln Arg
            2080                2085                2090

AGG GGG AGA GTT GGG AGA GTA AAG CCT GGA AGA TAC TAC AGG AGT CAA      6697
Arg Gly Arg Val Gly Arg Val Lys Pro Gly Arg Tyr Tyr Arg Ser Gln
        2095                2100                2105

GAA ACT CCC GTT GGT TCT AAA GAT TAC CAT TAT GAT TTA CTG CAA GCA      6745
Glu Thr Pro Val Gly Ser Lys Asp Tyr His Tyr Asp Leu Leu Gln Ala
2110                2115                2120

CAG AGG TAC GGT ATT GAA GAT GGG ATA AAC ATC ACC AAA TCC TTT AGA      6793
Gln Arg Tyr Gly Ile Glu Asp Gly Ile Asn Ile Thr Lys Ser Phe Arg
2125                2130                2135                2140

GAG ATG AAC TAT GAT TGG AGC CTT TAT GAG GAG GAC AGT CTG ATG ATT      6841
Glu Met Asn Tyr Asp Trp Ser Leu Tyr Glu Glu Asp Ser Leu Met Ile
                2145                2150                2155

ACA CAA TTG GAA ATT CTT AAT AAT TTG TTG ATA TCA GAT GAA CTA CCA      6889
Thr Gln Leu Glu Ile Leu Asn Asn Leu Leu Ile Ser Asp Glu Leu Pro
            2160                2165                2170

ATG GCA GTA AAA AAT ATA ATG GCC AGG ACT GAC CAC CCA GAA CCA ATT      6937
Met Ala Val Lys Asn Ile Met Ala Arg Thr Asp His Pro Glu Pro Ile
        2175                2180                2185

CAG CTG GCG TAC AAC AGC TAC GAA ACA CAA GTG CCA GTG CTA TTC CCA      6985
Gln Leu Ala Tyr Asn Ser Tyr Glu Thr Gln Val Pro Val Leu Phe Pro
```

-continued

```
        2190               2195               2200
AAA ATA AAG AAT GGA GAG GTG ACT GAC AGT TAC GAT AAC TAT ACC TTC    7033
Lys Ile Lys Asn Gly Glu Val Thr Asp Ser Tyr Asp Asn Tyr Thr Phe
2205           2210               2215               2220

CTC AAC GCA AGA AAA TTA GGG GAT GAT GTA CCC CCT TAC GTG TAT GCC    7081
Leu Asn Ala Arg Lys Leu Gly Asp Asp Val Pro Pro Tyr Val Tyr Ala
                2225               2230               2235

ACA GAG GAT GAG GAC TTA GCG GTA GAG CTG CTG GGC TTA GAC TGG CCG    7129
Thr Glu Asp Glu Asp Leu Ala Val Glu Leu Leu Gly Leu Asp Trp Pro
            2240               2245               2250

GAC CCT GGA AAC CAA GGG ACC GTA GAG ACT GGC AGA GCA CTA AAA CAG    7177
Asp Pro Gly Asn Gln Gly Thr Val Glu Thr Gly Arg Ala Leu Lys Gln
        2255               2260               2265

GTA GTT GGT CTA TCA ACA GCT GAG AAT GCC CTG TTA GTA GCC TTA TTC    7225
Val Val Gly Leu Ser Thr Ala Glu Asn Ala Leu Leu Val Ala Leu Phe
    2270               2275               2280

GGC TAC GTA GGA TAT CAG GCG CTT TCA AAG AGG CAT ATA CCA GTA GTC    7273
Gly Tyr Val Gly Tyr Gln Ala Leu Ser Lys Arg His Ile Pro Val Val
2285               2290               2295               2300

ACA GAC ATA TAT TCA ATT GAA GAT CAC AGG TTG GAA GAC ACC ACA CAC    7321
Thr Asp Ile Tyr Ser Ile Glu Asp His Arg Leu Glu Asp Thr Thr His
                2305               2310               2315

CTA CAG TAC GCC CCA AAT GCT ATC AAG ACG GAG GGG AAG GAG ACA GAA    7369
Leu Gln Tyr Ala Pro Asn Ala Ile Lys Thr Glu Gly Lys Glu Thr Glu
            2320               2325               2330

TTG AAA GAG CTA GCT CAG GGG GAT GTG CAG AGA TGT GTG GAA GCC ATG    7417
Leu Lys Glu Leu Ala Gln Gly Asp Val Gln Arg Cys Val Glu Ala Met
        2335               2340               2345

ACC AAT TAT GCA AGA GAG GGT ATC CAA TTT ATG AAG TCT CAG GCA CTG    7465
Thr Asn Tyr Ala Arg Glu Gly Ile Gln Phe Met Lys Ser Gln Ala Leu
    2350               2355               2360

AAG GTG AAG GAA ACC CCT ACT TAC AAG GAG ACA ATG GAC ACT GTG ACG    7513
Lys Val Lys Glu Thr Pro Thr Tyr Lys Glu Thr Met Asp Thr Val Thr
2365               2370               2375               2380

GAC TAT GTA AAG AAA TTC ATG GAG GCG CTG GCA GAC AGT AAA GAA GAC    7561
Asp Tyr Val Lys Lys Phe Met Glu Ala Leu Ala Asp Ser Lys Glu Asp
                2385               2390               2395

ATC ATA AAA TAT GGG CTG TGG GGG ACG CAC ACA GCC TTA TAT AAG AGC    7609
Ile Ile Lys Tyr Gly Leu Trp Gly Thr His Thr Ala Leu Tyr Lys Ser
            2400               2405               2410

ATC AGT GCC AGG CTT GGG GGT GAG ACT GCG TTC GCT ACC CTG GTA GTG    7657
Ile Ser Ala Arg Leu Gly Gly Glu Thr Ala Phe Ala Thr Leu Val Val
        2415               2420               2425

AAG TGG CTG GCA TTT GGG GGT GAA TCA ATA GCA GAC CAT GTC AAA CAA    7705
Lys Trp Leu Ala Phe Gly Gly Glu Ser Ile Ala Asp His Val Lys Gln
    2430               2435               2440

GCG GCC ACA GAC TTG GTC GTT TAC TAT ATC ATC AAC AGA CCT CAG TTC    7753
Ala Ala Thr Asp Leu Val Val Tyr Tyr Ile Ile Asn Arg Pro Gln Phe
2445               2450               2455               2460

CCA GGA GAC ACG GAG ACA CAA CAA GAC GGA AGG AAA TTT GTG GCC AGC    7801
Pro Gly Asp Thr Glu Thr Gln Gln Asp Gly Arg Lys Phe Val Ala Ser
                2465               2470               2475

CTA CTG GCC TCA GCT CTA GCT ACT TAC ACA TAC AAA AGC TGG AAT TAC    7849
Leu Leu Ala Ser Ala Leu Ala Thr Tyr Thr Tyr Lys Ser Trp Asn Tyr
            2480               2485               2490

AAT AAC CTG TCC AAG ATA GTT GAA CCG GCT TTG GCC ACT CTG CCC TAT    7897
Asn Asn Leu Ser Lys Ile Val Glu Pro Ala Leu Ala Thr Leu Pro Tyr
        2495               2500               2505

GCC GCC ACA GCT CTC AAA TTA TTC GCC CCC ACC CGA TTG GAG AGC GTT    7945
```

```
                                                                    -continued Ala Ala Thr Ala Leu Lys Leu Phe Ala Pro Thr Arg Leu Glu Ser Val
        2510                2515                2520

GTC ATA TTA AGT ACC GCA ATC TAC AAA ACC TAC CTA TCA ATC AGG CGC         7993
Val Ile Leu Ser Thr Ala Ile Tyr Lys Thr Tyr Leu Ser Ile Arg Arg
2525                2530                2535                2540

GGA AAA AGC GAT GGT TTG CTA GGC ACG GGG GTT AGT GCG GCT ATG GAG         8041
Gly Lys Ser Asp Gly Leu Leu Gly Thr Gly Val Ser Ala Ala Met Glu
                2545                2550                2555

ATC ATG TCA CAA AAT CCA GTA TCC GTG GGC ATA GCA GTC ATG CTA GGG         8089
Ile Met Ser Gln Asn Pro Val Ser Val Gly Ile Ala Val Met Leu Gly
            2560                2565                2570

GTA GGG GCC GTG GCA GCC CAC AAT GCA ATC GAA GCC AGT GAG CAG AAA         8137
Val Gly Ala Val Ala Ala His Asn Ala Ile Glu Ala Ser Glu Gln Lys
        2575                2580                2585

AGA ACA CTA CTC ATG AAA GTC TTT GTA AAG AAC TTG GAC CAG GCA             8185
Arg Thr Leu Leu Met Lys Val Phe Val Lys Asn Phe Leu Asp Gln Ala
    2590                2595                2600

GCC ACA GAT GAA TTA GTC AAG GAG AGT CCT GAA AAA ATA ATA ATG GCT         8233
Ala Thr Asp Glu Leu Val Lys Glu Ser Pro Glu Lys Ile Ile Met Ala
2605                2610                2615                2620

TTG TTT GAA GCA GTG CAG ACA GTC GGC AAC CCT CTT AGA CTT GTA TAC         8281
Leu Phe Glu Ala Val Gln Thr Val Gly Asn Pro Leu Arg Leu Val Tyr
                2625                2630                2635

CAC CTT TAT GGA GTT TTT TAT AAA GGG TGG GAG GCA AAA GAG TTG GCC         8329
His Leu Tyr Gly Val Phe Tyr Lys Gly Trp Glu Ala Lys Glu Leu Ala
            2640                2645                2650

CAA AGG ACA GCC GGT AGG AAC CTT TTC ACT TTA ATC ATG TTC GAG GCT         8377
Gln Arg Thr Ala Gly Arg Asn Leu Phe Thr Leu Ile Met Phe Glu Ala
        2655                2660                2665

GTG GAA CTG CTG GGA GTA GAC AGT GAA GGA AAG GTC CGC CAG CTA TCA         8425
Val Glu Leu Leu Gly Val Asp Ser Glu Gly Lys Val Arg Gln Leu Ser
    2670                2675                2680

AGT AAT TAC ATA CTA GAG CTT TTG TAT AAG TTC CGT GAC AGT ATC AAG         8473
Ser Asn Tyr Ile Leu Glu Leu Leu Tyr Lys Phe Arg Asp Ser Ile Lys
2685                2690                2695                2700

TCT AGC GTG AGG GAG ATG GCA ATC AGC TGG GCC CCT GCC CCT TTC AGT         8521
Ser Ser Val Arg Glu Met Ala Ile Ser Trp Ala Pro Ala Pro Phe Ser
                2705                2710                2715

TGT GAT TGG ACA CCG ACG GAT GAC AGA ATA GGG CTC CCC CAA GAC AAT         8569
Cys Asp Trp Thr Pro Thr Asp Asp Arg Ile Gly Leu Pro Gln Asp Asn
            2720                2725                2730

TTC CAC CAA GTG GAG ACG AAA TGC CCC TGT GGT TAC AAG ATG AAG GCA         8617
Phe His Gln Val Glu Thr Lys Cys Pro Cys Gly Tyr Lys Met Lys Ala
        2735                2740                2745

GTT AAG AAT TGT GCT GGA GAA CTG AGA CTC TTG GAG GAG GAG GGT TCA         8665
Val Lys Asn Cys Ala Gly Glu Leu Arg Leu Leu Glu Glu Glu Gly Ser
    2750                2755                2760

TTT CTC TGC AGA AAT AAA TTC GGG AGA GGT TCA CGG AAC TAC AGA GTG         8713
Phe Leu Cys Arg Asn Lys Phe Gly Arg Gly Ser Arg Asn Tyr Arg Val
2765                2770                2775                2780

ACA AAA TAT TAT GAT GAC AAC CTA TTA GAA ATA AAG CCA GTG ATA AGA         8761
Thr Lys Tyr Tyr Asp Asp Asn Leu Leu Glu Ile Lys Pro Val Ile Arg
                2785                2790                2795

ATG GAA GGG CAT GTG GAA CTC TAC TAC AAG GGG GCC ACC ATC AAA CTG         8809
Met Glu Gly His Val Glu Leu Tyr Tyr Lys Gly Ala Thr Ile Lys Leu
            2800                2805                2810

GAT TTC AAC AAC AGC AAA ACA ATA TTG GCA ACC GAT AAA TGG GAG GTT         8857
Asp Phe Asn Asn Ser Lys Thr Ile Leu Ala Thr Asp Lys Trp Glu Val
        2815                2820                2825
```

```
GAT CAC TCC ACT CTG GTC AGG GTG CTC AAG AGG CAC ACA GGG GCT GGA    8905
Asp His Ser Thr Leu Val Arg Val Leu Lys Arg His Thr Gly Ala Gly
        2830                2835                2840

TAT CAT GGG GCA TAC CTG GGC GAG AAA CCG AAC CAC AAA CAC CTG ATA    8953
Tyr His Gly Ala Tyr Leu Gly Glu Lys Pro Asn His Lys His Leu Ile
2845                2850                2855                2860

GAG AGG GAC TGT GCA ACC ATC ACC AAA GAT AAG GTC TGT TTT CTC AAA    9001
Glu Arg Asp Cys Ala Thr Ile Thr Lys Asp Lys Val Cys Phe Leu Lys
                2865                2870                2875

ATG AAG AGA GGG TGC GCA TTT ACT TAT GAC TTA TCC CTT CAC AAC CTT    9049
Met Lys Arg Gly Cys Ala Phe Thr Tyr Asp Leu Ser Leu His Asn Leu
            2880                2885                2890

ACC CGA CTG ATT GAA TTG GTA CAC AAG AAT AAC TTG GAA GAC AAA GAG    9097
Thr Arg Leu Ile Glu Leu Val His Lys Asn Asn Leu Glu Asp Lys Glu
                2895                2900                2905

ATT CCC GCT GCT ACG GTT ACA ACC TGG CTG GCT TAC ACA TTT GTA AAT    9145
Ile Pro Ala Ala Thr Val Thr Thr Trp Leu Ala Tyr Thr Phe Val Asn
            2910                2915                2920

GAA GAT ATA GGG ACC ATA AAA CCA GCC TTC GGG GAG AAA GTA ACG CTG    9193
Glu Asp Ile Gly Thr Ile Lys Pro Ala Phe Gly Glu Lys Val Thr Leu
2925                2930                2935                2940

GAG ATG CAG GAG GAG ATA ACC TTG CAG CCT GCT GTT GTG GTG GAT ACA    9241
Glu Met Gln Glu Glu Ile Thr Leu Gln Pro Ala Val Val Val Asp Thr
                2945                2950                2955

ACA GAC GTA GCC GTG ACT GTG GTA GGG GAA GCC CCC ACT ATG ACT ACA    9289
Thr Asp Val Ala Val Thr Val Val Gly Glu Ala Pro Thr Met Thr Thr
            2960                2965                2970

GGG GAG ACA CCG ACA GTG TTC ACC AGC TCA GGT TCA GGC CTG AAA AGC    9337
Gly Glu Thr Pro Thr Val Phe Thr Ser Ser Gly Ser Gly Leu Lys Ser
            2975                2980                2985

CAA CAA GTT TTG AAA CTA GGG GTA GGT GAA GGC CAA TAT CCA GGG ACT    9385
Gln Gln Val Leu Lys Leu Gly Val Gly Glu Gly Gln Tyr Pro Gly Thr
    2990                2995                3000

AAT CCA CAG AGG GCA AGC CTG CAC GAA GCC ATA CAA GGT GCA GAT GAG    9433
Asn Pro Gln Arg Ala Ser Leu His Glu Ala Ile Gln Gly Ala Asp Glu
3005                3010                3015                3020

AGG CCC TCG GTG CTG ATA TTG GGG TCT GAT AAA GCC ACC TCT AAT AGA    9481
Arg Pro Ser Val Leu Ile Leu Gly Ser Asp Lys Ala Thr Ser Asn Arg
                3025                3030                3035

GTG AAG ACT GCA AAG AAT GTA AAG GTA TAC AGA GGC AGG GAC CCA CTA    9529
Val Lys Thr Ala Lys Asn Val Lys Val Tyr Arg Gly Arg Asp Pro Leu
            3040                3045                3050

GAA GTG AGA GAT ATG ATG AGG AGG GGA AAG ATC CTG GTC GTA GCC CTG    9577
Glu Val Arg Asp Met Met Arg Arg Gly Lys Ile Leu Val Val Ala Leu
        3055                3060                3065

TCT AGG GTT GAT AAT GCT CTA TTG AAA TTT GTT GAC TAC AAA GGC ACC    9625
Ser Arg Val Asp Asn Ala Leu Leu Lys Phe Val Asp Tyr Lys Gly Thr
    3070                3075                3080

TTT CTA ACT AGG GAG GCC CTA GAG GCA TTA AGT TTG GGC AGG CCT AAA    9673
Phe Leu Thr Arg Glu Ala Leu Glu Ala Leu Ser Leu Gly Arg Pro Lys
3085                3090                3095                3100

AAG AAA AAC ATA ACC AAG GCA GAA GCG CAG TGG TTG CTG TGC CCC GAG    9721
Lys Lys Asn Ile Thr Lys Ala Glu Ala Gln Trp Leu Leu Cys Pro Glu
                3105                3110                3115

GAC CAA ATG GAA GAG CTA CCC GAC TGG TTC GCA GCC GGG GAA CCC ATT    9769
Asp Gln Met Glu Glu Leu Pro Asp Trp Phe Ala Ala Gly Glu Pro Ile
            3120                3125                3130

TTT TTA GAG GCC AAC ATT AAA CAT GAC AGG TAC CAT CTG GTG GGG GAT    9817
Phe Leu Glu Ala Asn Ile Lys His Asp Arg Tyr His Leu Val Gly Asp
            3135                3140                3145
```

```
ATA GCT ACC ATC AAG GAA AAA GCC AAA CAG TTG GGG GCT ACA GAC TCC          9865
Ile Ala Thr Ile Lys Glu Lys Ala Lys Gln Leu Gly Ala Thr Asp Ser
        3150                3155                3160

ACA AAG ATA TCT AAG GAG GTT GGT GCT AAA GTG TAT TCT ATG AAA CTG          9913
Thr Lys Ile Ser Lys Glu Val Gly Ala Lys Val Tyr Ser Met Lys Leu
3165                3170                3175                3180

AGT AAT TGG GTG ATG CAA GAA GAA AAT AAA CAG GGC AAT CTG ACC CCC          9961
Ser Asn Trp Val Met Gln Glu Glu Asn Lys Gln Gly Asn Leu Thr Pro
                3185                3190                3195

TTG TTT GAA GAG CTC CTG CAA CAG TGT CCA CCC GGG GGC CAG AAC AAA         10009
Leu Phe Glu Glu Leu Leu Gln Gln Cys Pro Pro Gly Gly Gln Asn Lys
            3200                3205                3210

ACT GCA CAC ATG GTC TCT GCT TAC CAA CTA GCT CAA GGG AAC TGG ATG         10057
Thr Ala His Met Val Ser Ala Tyr Gln Leu Ala Gln Gly Asn Trp Met
        3215                3220                3225

CCG ACC AGC TGC CAT GTT TTC ATG GGG ACC GTA TCT GCC AGG AGA ACC         10105
Pro Thr Ser Cys His Val Phe Met Gly Thr Val Ser Ala Arg Arg Thr
3230                3235                3240

AAG ACC CAC CCA TAC GAA GCA TAC GTT AAG TTA AGG GAG TTG GTA GAG         10153
Lys Thr His Pro Tyr Glu Ala Tyr Val Lys Leu Arg Glu Leu Val Glu
3245                3250                3255                3260

GAG CAC AAG ATG AAA ACA CTG TGT CCC GGA TCA AGC CTG GGT AGG CAC         10201
Glu His Lys Met Lys Thr Leu Cys Pro Gly Ser Ser Leu Gly Arg His
                3265                3270                3275

AAC GAT TGG ATA ATT GGA AAA ATT AAA TAC CAG GGA AAC CTG AGG ACC         10249
Asn Asp Trp Ile Ile Gly Lys Ile Lys Tyr Gln Gly Asn Leu Arg Thr
            3280                3285                3290

AAA CAC ATG TTG AAC CCC GGC AAG GTG GCA GAG CAA CTG TGC AGA GAG         10297
Lys His Met Leu Asn Pro Gly Lys Val Ala Glu Gln Leu Cys Arg Glu
        3295                3300                3305

GGA CAC AGA CAC AAT GTG TAT AAC AAG ACA ATA AGC TCA GTA ATG ACA         10345
Gly His Arg His Asn Val Tyr Asn Lys Thr Ile Ser Ser Val Met Thr
3310                3315                3320

GCT ACT GGT ATC AGG TTG GAG AAG TTG CCC GTG GTT AGG GCC CAG ACA         10393
Ala Thr Gly Ile Arg Leu Glu Lys Leu Pro Val Val Arg Ala Gln Thr
3325                3330                3335                3340

GAC CCA ACC AAC TTC CAC CAA GCA ATA AGG GAT AAG ATA GAC AAG GAA         10441
Asp Pro Thr Asn Phe His Gln Ala Ile Arg Asp Lys Ile Asp Lys Glu
                3345                3350                3355

GAG AAC CTA CAA ACC CCG GGT TTA CAT AAG AAA TTA ATG GAA GTT TTC         10489
Glu Asn Leu Gln Thr Pro Gly Leu His Lys Lys Leu Met Glu Val Phe
            3360                3365                3370

AAC GCA TTG AAA CGA CCC GAG TTA GAG TCC TCC TAC GAC GCC GTG GAA         10537
Asn Ala Leu Lys Arg Pro Glu Leu Glu Ser Ser Tyr Asp Ala Val Glu
        3375                3380                3385

TGG GAG GAA CTG GAG AGA GGA ATA AAC AGG AAG GGT GCT GCT GGT TTT         10585
Trp Glu Glu Leu Glu Arg Gly Ile Asn Arg Lys Gly Ala Ala Gly Phe
3390                3395                3400

TTC GAA CGC AAA AAT ATA GGG GAA ATA TTG GAT TCA GAG AAA AAT AAA         10633
Phe Glu Arg Lys Asn Ile Gly Glu Ile Leu Asp Ser Glu Lys Asn Lys
3405                3410                3415                3420

GTC GAA GAG ATT ATT GAC AAT CTG AAA AAA GGT AGA AAC ATT AAA TAT         10681
Val Glu Glu Ile Ile Asp Asn Leu Lys Lys Gly Arg Asn Ile Lys Tyr
                3425                3430                3435

TAT GAA ACC GCG ATC CCA AAG AAT GAG AAG AGG GAC GTC AAC GAT GAC         10729
Tyr Glu Thr Ala Ile Pro Lys Asn Glu Lys Arg Asp Val Asn Asp Asp
            3440                3445                3450

TGG ACC GCC GGT GAT TTC GTG GAC GAG AAG AAA CCT AGA GTC ATA CAA         10777
Trp Thr Ala Gly Asp Phe Val Asp Glu Lys Lys Pro Arg Val Ile Gln
```

-continued

```
           3455              3460              3465
TAC CCT GAA GCA AAA ACA AGA CTG GCC ATC ACC AAG GTG ATG TAT AAG    10825
Tyr Pro Glu Ala Lys Thr Arg Leu Ala Ile Thr Lys Val Met Tyr Lys
    3470              3475              3480

TGG GTG AAG CAG AAG CCA GTA GTT ATA CCC GGG TAT GAA GGG AAG ACA    10873
Trp Val Lys Gln Lys Pro Val Val Ile Pro Gly Tyr Glu Gly Lys Thr
3485              3490              3495              3500

CCT CTA TTC CAA ATT TTT GAC AAA GTA AAG AAG GAA TGG GAT CAA TTT    10921
Pro Leu Phe Gln Ile Phe Asp Lys Val Lys Lys Glu Trp Asp Gln Phe
                3505              3510              3515

CAA AAT CCA GTG GCA GTG AGC TTC GAC ACT AAG GCG TGG GAC ACC CAG    10969
Gln Asn Pro Val Ala Val Ser Phe Asp Thr Lys Ala Trp Asp Thr Gln
            3520              3525              3530

GTA ACC ACA AAA GAT TTG GAG CTG ATA AGG GAC ATA CAA AAG TAT TAT    11017
Val Thr Thr Lys Asp Leu Glu Leu Ile Arg Asp Ile Gln Lys Tyr Tyr
        3535              3540              3545

TTC AAG AAG AAA TGG CAC AAA TTT ATT GAC ACC CTG ACC ACG CAT ATG    11065
Phe Lys Lys Lys Trp His Lys Phe Ile Asp Thr Leu Thr Thr His Met
    3550              3555              3560

TCA GAA GTA CCC GTG ATC AGT GCT GAT GGG GAA GTA TAC ATA AGG AAA    11113
Ser Glu Val Pro Val Ile Ser Ala Asp Gly Glu Val Tyr Ile Arg Lys
3565              3570              3575              3580

GGG CAA AGA GGC AGT GGA CAA CCT GAC ACA AGT GCG GGC AAC AGC ATG    11161
Gly Gln Arg Gly Ser Gly Gln Pro Asp Thr Ser Ala Gly Asn Ser Met
                3585              3590              3595

CTA AAT GTC TTA ACA ATG GTT TAC GCC TTC TGC GAG GCC ACA GGA GTA    11209
Leu Asn Val Leu Thr Met Val Tyr Ala Phe Cys Glu Ala Thr Gly Val
            3600              3605              3610

CCC TAC AAG AGC TTT GAC AGG GTG GCA AAA ATT CAT GTG TGC GGG GAT    11257
Pro Tyr Lys Ser Phe Asp Arg Val Ala Lys Ile His Val Cys Gly Asp
        3615              3620              3625

GAT GGC TTC CTG ATC ACA GAA AGA GCT CTC GGT GAG AAA TTT GCA AGT    11305
Asp Gly Phe Leu Ile Thr Glu Arg Ala Leu Gly Glu Lys Phe Ala Ser
    3630              3635              3640

AAG GGA GTC CAG ATC CTT TAT GAA GCT GGG AAG CCC CAG AAG ATC ACT    11353
Lys Gly Val Gln Ile Leu Tyr Glu Ala Gly Lys Pro Gln Lys Ile Thr
3645              3650              3655              3660

GAA GGG GAC AAA ATG AAA GTG GCC TAC CAA TTT GAT GAT ATT GAG TTT    11401
Glu Gly Asp Lys Met Lys Val Ala Tyr Gln Phe Asp Asp Ile Glu Phe
                3665              3670              3675

TGC TCC CAT ACA CCA ATA CAA GTA AGA TGG TCA GAT AAC ACT TCT AGT    11449
Cys Ser His Thr Pro Ile Gln Val Arg Trp Ser Asp Asn Thr Ser Ser
            3680              3685              3690

TAC ATG CCG GGG AGA AAT ACA ACC ACA ATC CTG GCA AAG ATG GCC ACG    11497
Tyr Met Pro Gly Arg Asn Thr Thr Thr Ile Leu Ala Lys Met Ala Thr
        3695              3700              3705

AGG TTA GAT TCC AGC GGT GAA AGG GGT ACC ATA GCA TAT GAG AAA GCA    11545
Arg Leu Asp Ser Ser Gly Glu Arg Gly Thr Ile Ala Tyr Glu Lys Ala
    3710              3715              3720

GTA GCA TTT AGC TTC CTG CTG ATG TAC TCC TGG AAC CCA CTA ATT AGA    11593
Val Ala Phe Ser Phe Leu Leu Met Tyr Ser Trp Asn Pro Leu Ile Arg
3725              3730              3735              3740

AGG ATC TGC TTA CTG GTG CTA TCA ACT GAA CTG CAA GTG AAA CCA GGG    11641
Arg Ile Cys Leu Leu Val Leu Ser Thr Glu Leu Gln Val Lys Pro Gly
                3745              3750              3755

AAG TCA ACT ACT TAC TAT TAT GAA GGA GAC CCG ATA TCT GCC TAC AAG    11689
Lys Ser Thr Thr Tyr Tyr Tyr Glu Gly Asp Pro Ile Ser Ala Tyr Lys
            3760              3765              3770

GAA GTC ATC GGC CAC AAC CTT TTT GAT CTT AAG AGA ACA AGC TTT GAG    11737
```

```
Glu Val Ile Gly His Asn Leu Phe Asp Leu Lys Arg Thr Ser Phe Glu
        3775                3780                3785

AAG CTG GCC AAG TTA AAT CTT AGC ATG TCT GTA CTC GGG GCC TGG ACT            11785
Lys Leu Ala Lys Leu Asn Leu Ser Met Ser Val Leu Gly Ala Trp Thr
    3790                3795                3800

AGA CAC ACC AGT AAA AGA CTA CTA CAA GAC TGT GTC AAT ATA GGT GTT            11833
Arg His Thr Ser Lys Arg Leu Leu Gln Asp Cys Val Asn Ile Gly Val
3805                3810                3815                3820

AAA GAG GGC AAT TGG CTA GTC AAT GCA GAC AGA CTA GTA AGT AGC AAG            11881
Lys Glu Gly Asn Trp Leu Val Asn Ala Asp Arg Leu Val Ser Ser Lys
                3825                3830                3835

ACC GGG AAT AGG TAC ATA CCC GGA GAG GGT CAC ACC CTG CAA GGA AGA            11929
Thr Gly Asn Arg Tyr Ile Pro Gly Glu Gly His Thr Leu Gln Gly Arg
        3840                3845                3850

CAT TAT GAA GAA CTG GTG TTG GCA AGA AAA CAG ATC AAC AAC TTT CAA            11977
His Tyr Glu Glu Leu Val Leu Ala Arg Lys Gln Ile Asn Asn Phe Gln
        3855                3860                3865

GGG ACA GAC AGG TAC AAC CTA GGC CCA ATA GTC AAC ATG GTG TTA AGG            12025
Gly Thr Asp Arg Tyr Asn Leu Gly Pro Ile Val Asn Met Val Leu Arg
    3870                3875                3880

AGG CTG AGA GTC ATG ATG ATG ACG CTG ATA GGG AGA GGG GCA                    12067
Arg Leu Arg Val Met Met Met Thr Leu Ile Gly Arg Gly Ala
3885                3890                3895

TGAGCGCGGG TAACCCGGGA TCTGAACCCG CCAGTAGGAC CCTATTGTAG ATAACACTAA          12127

TTTTCTTTTT TTTCTTTTTT ATTTATTTAG ATATTATTAT TTATTTATTT ATTTATTTAT          12187

TGAATGAGTA AGAACTGGTA TAAACTACCT CAAGTTACCA CACTACACTC ATTTTTAACA          12247

GCACTTTAGC TGGAAGGAAA ATTCCTGACG TCCACAGTTG GGCTAAGGTA ATTTCTAACG          12307

GCCC                                                                       12311

(2) INFORMATION FOR SEQ ID NO:2:

(i) SEQUENCE CHARACTERISTICS:
        (A) LENGTH: 3898 amino acids
        (B) TYPE: amino acid
        (D) TOPOLOGY: linear (ii) MOLECULE TYPE: protein (xi) SEQUENCE DESCRIPTION: SEQ ID NO:2:

Met Glu Leu Asn His Phe Glu Leu Leu Tyr Lys Thr Asn Lys Gln Lys
1               5                   10                  15

Pro Met Gly Val Glu Pro Val Tyr Asp Ala Thr Gly Arg Pro Leu
            20                  25                  30

Phe Gly Asp Pro Ser Glu Val His Pro Gln Ser Thr Leu Lys Leu Pro
        35                  40                  45

His Asp Arg Gly Arg Gly Asn Ile Lys Thr Thr Leu Lys Asn Leu Pro
    50                  55                  60

Arg Lys Gly Asp Cys Arg Ser Gly Asn His Leu Gly Pro Val Ser Gly
65              70                  75                  80

Ile Tyr Val Lys Pro Gly Pro Val Phe Tyr Gln Asp Tyr Met Gly Pro
                85                  90                  95

Val Tyr His Arg Ala Pro Leu Glu Phe Phe Asp Glu Val Gln Phe Cys
            100                 105                 110

Glu Val Thr Lys Arg Ile Gly Arg Val Thr Gly Ser Asp Gly Lys Leu
        115                 120                 125

Tyr His Thr Tyr Val Cys Ile Asp Gly Cys Ile Leu Leu Lys Leu Ala
    130                 135                 140
```

```
Lys Arg Gly Glu Pro Arg Thr Leu Lys Trp Ile Arg Asn Phe Thr Asp
145                 150                 155                 160

Cys Pro Leu Trp Val Thr Ser Cys Ser Asp Asp Gly Ala Ser Gly Ser
                165                 170                 175

Lys Glu Lys Lys Pro Asp Arg Ile Asn Lys Gly Lys Leu Lys Ile Ala
            180                 185                 190

Pro Lys Glu His Glu Lys Asp Ser Arg Thr Arg Pro Pro Asp Ala Thr
        195                 200                 205

Ile Val Val Glu Gly Val Lys Tyr Gln Val Lys Lys Gly Lys Val
    210                 215                 220

Lys Gly Lys Asn Thr Gln Asp Gly Leu Tyr His Asn Lys Asn Lys Pro
225                 230                 235                 240

Pro Glu Ser Arg Lys Lys Leu Glu Lys Ala Leu Leu Ala Trp Ala Val
                245                 250                 255

Ile Ala Ile Met Leu Tyr Gln Pro Val Glu Ala Glu Asn Ile Thr Gln
            260                 265                 270

Trp Asn Leu Ser Asp Asn Gly Thr Asn Gly Ile Gln His Ala Met Tyr
        275                 280                 285

Leu Arg Gly Val Asn Arg Ser Leu His Gly Ile Trp Pro Gly Glu Ile
    290                 295                 300

Cys Lys Gly Val Pro Thr His Leu Ala Thr Asp Val Glu Leu Lys Glu
305                 310                 315                 320

Ile Gln Gly Met Met Asp Ala Ser Glu Gly Thr Asn Tyr Thr Cys Cys
                325                 330                 335

Lys Leu Gln Arg His Glu Trp Asn Lys His Gly Trp Cys Asn Trp His
            340                 345                 350

Asn Ile Asp Pro Trp Ile Gln Leu Met Asn Arg Thr Gln Ala Asp Leu
        355                 360                 365

Ala Glu Gly Pro Pro Val Lys Glu Cys Ala Val Thr Cys Arg Tyr Asp
    370                 375                 380

Lys Asp Ala Asp Ile Asn Val Val Thr Gln Ala Arg Asn Arg Pro Thr
385                 390                 395                 400

Thr Leu Thr Gly Cys Lys Lys Gly Lys Asn Phe Ser Phe Ala Gly Thr
                405                 410                 415

Val Ile Glu Ser Pro Cys Asn Phe Asn Val Ser Val Glu Asp Thr Leu
            420                 425                 430

Tyr Gly Asp His Glu Cys Gly Ser Leu Leu Gln Asp Ala Ala Leu Tyr
        435                 440                 445

Leu Val Asp Gly Met Thr Asn Thr Ile Glu Asn Ala Arg Gln Gly Ala
    450                 455                 460

Ala Arg Val Thr Ser Trp Leu Gly Arg Gln Leu Arg Thr Ala Gly Lys
465                 470                 475                 480

Arg Leu Glu Gly Arg Ser Lys Thr Trp Phe Gly Ala Tyr Ala Leu Ser
                485                 490                 495

Pro Tyr Cys Asn Val Thr Ser Lys Ile Gly Tyr Ile Trp Tyr Thr Asn
            500                 505                 510

Asn Cys Thr Pro Ala Cys Leu Pro Lys Asn Thr Lys Ile Ile Gly Pro
        515                 520                 525

Gly Lys Phe Asp Thr Asn Ala Glu Asp Gly Lys Ile Leu His Glu Met
    530                 535                 540

Gly Gly His Leu Ser Glu Phe Leu Leu Leu Ser Leu Val Val Leu Ser
545                 550                 555                 560
```

-continued

```
Asp Phe Ala Pro Glu Thr Ala Ser Ala Leu Tyr Leu Ile Leu His Tyr
                565                 570                 575

Val Ile Pro Gln Pro His Asp Glu Pro Glu Gly Cys Asp Thr Asn Gln
            580                 585                 590

Leu Asn Leu Thr Val Glu Leu Arg Thr Glu Asp Val Ile Pro Ser Ser
        595                 600                 605

Val Trp Asn Val Gly Lys Tyr Val Cys Val Arg Pro Asp Trp Trp Pro
610                 615                 620

Tyr Glu Thr Glu Val Ala Leu Leu Phe Glu Glu Val Gly Gln Val Val
625                 630                 635                 640

Lys Leu Ala Leu Arg Ala Leu Arg Asp Leu Thr Arg Val Trp Asn Ser
                645                 650                 655

Ala Ser Thr Ile Ala Phe Leu Ile Cys Leu Ile Lys Val Leu Arg Gly
            660                 665                 670

Gln Ile Val Gln Gly Val Val Trp Leu Leu Leu Val Thr Gly Ala Gln
        675                 680                 685

Gly Arg Leu Ala Cys Lys Glu Asp Tyr Arg Tyr Ala Ile Ser Ser Thr
    690                 695                 700

Asp Glu Ile Gly Leu Leu Gly Ala Gly Gly Leu Thr Thr Thr Trp Lys
705                 710                 715                 720

Glu Tyr Asn His Asp Leu Gln Leu Asn Asp Gly Thr Val Lys Ala Ser
                725                 730                 735

Cys Val Ala Gly Ser Phe Lys Val Thr Ala Leu Asn Val Val Ser Arg
            740                 745                 750

Arg Tyr Leu Ala Ser Leu His Lys Lys Ala Leu Pro Thr Ser Val Thr
        755                 760                 765

Phe Glu Leu Leu Phe Asp Gly Thr Asn Pro Ser Thr Glu Glu Met Gly
    770                 775                 780

Asp Asp Phe Arg Ser Gly Leu Cys Pro Phe Asp Thr Ser Pro Val Val
785                 790                 795                 800

Lys Gly Lys Tyr Asn Thr Thr Leu Leu Asn Gly Ser Ala Phe Tyr Leu
                805                 810                 815

Val Cys Pro Ile Gly Trp Thr Gly Val Ile Glu Cys Thr Ala Val Ser
            820                 825                 830

Pro Thr Thr Leu Arg Thr Glu Val Val Lys Thr Phe Arg Arg Asp Lys
        835                 840                 845

Pro Phe Pro His Arg Met Asp Cys Val Thr Thr Thr Val Glu Asn Glu
    850                 855                 860

Asp Leu Phe Tyr Cys Lys Leu Gly Gly Asn Trp Thr Cys Val Lys Gly
865                 870                 875                 880

Glu Pro Val Val Tyr Thr Gly Gly Leu Val Lys Gln Cys Arg Trp Cys
                885                 890                 895

Gly Phe Asp Phe Asp Gly Pro Asp Gly Leu Pro His Tyr Pro Ile Gly
            900                 905                 910

Lys Cys Ile Leu Ala Asn Glu Thr Gly Tyr Arg Ile Val Asp Ser Thr
        915                 920                 925

Asp Cys Asn Arg Asp Gly Val Val Ile Ser Thr Glu Gly Ser His Glu
    930                 935                 940

Cys Leu Ile Gly Asn Thr Thr Val Lys Val His Ala Ser Asp Glu Arg
945                 950                 955                 960

Leu Gly Pro Met Pro Cys Arg Pro Lys Glu Ile Val Ser Ser Ala Gly
                965                 970                 975

Pro Val Lys Lys Thr Ser Cys Thr Phe Asn Tyr Thr Lys Thr Leu Lys
```

-continued

```
                   980              985              990
Asn Arg Tyr Tyr Glu Pro Arg Asp Ser Tyr Phe Gln Gln Tyr Met Leu
                995              1000             1005
Lys Gly Glu Tyr Gln Tyr Trp Phe Asp Leu Asp Ala Thr Asp Arg His
1010             1015             1020
Ser Asp Tyr Phe Ala Glu Phe Val Val Leu Val Val Ala Leu Leu
1025             1030             1035             1040
Gly Gly Arg Tyr Val Leu Trp Leu Ile Val Thr Tyr Val Val Leu Thr
                1045             1050             1055
Glu Gln Leu Ala Ala Gly Leu Pro Leu Gly Gln Gly Glu Val Val Leu
                1060             1065             1070
Ile Gly Asn Leu Ile Thr His Thr Asp Ile Glu Val Val Tyr Phe
                1075             1080             1085
Leu Leu Leu Tyr Leu Val Met Arg Asp Glu Pro Ile Lys Lys Trp Ile
                1090             1095             1100
Leu Leu Leu Phe His Ala Met Thr Asn Asn Pro Val Lys Thr Ile Thr
1105             1110             1115             1120
Val Ala Leu Leu Met Val Ser Gly Val Ala Lys Gly Gly Lys Ile Asp
                1125             1130             1135
Gly Gly Trp Gln Arg Leu Pro Gly Thr Ser Phe Asp Ile Gln Leu Ala
                1140             1145             1150
Leu Thr Val Ile Val Ala Val Met Leu Leu Ala Lys Arg Asp Pro
                1155             1160             1165
Thr Thr Val Pro Leu Val Ile Thr Val Ala Pro Leu Arg Thr Ala Lys
                1170             1175             1180
Met Thr Asn Gly Leu Ser Thr Asp Ile Ala Ile Ala Thr Val Ser Ala
1185             1190             1195             1200
Ala Leu Leu Thr Trp Thr Tyr Ile Ser Asp Tyr Tyr Arg Tyr Lys Thr
                1205             1210             1215
Trp Leu Gln Tyr Leu Ile Ser Thr Val Thr Gly Ile Phe Leu Ile Arg
                1220             1225             1230
Val Leu Lys Gly Ile Gly Glu Leu Asp Leu His Thr Pro Thr Leu Pro
                1235             1240             1245
Ser His Arg Pro Leu Phe Phe Ile Leu Val Tyr Leu Ile Ser Thr Ala
                1250             1255             1260
Val Val Thr Arg Trp Asn Leu Asp Ile Ala Gly Leu Leu Leu Gln Cys
1265             1270             1275             1280
Val Pro Thr Leu Leu Met Val Phe Thr Met Trp Ala Asp Ile Leu Thr
                1285             1290             1295
Leu Ile Leu Ile Leu Pro Thr Tyr Glu Leu Thr Lys Leu Tyr Tyr Leu
                1300             1305             1310
Lys Glu Val Arg Ile Gly Ala Glu Lys Gly Trp Leu Trp Lys Thr Asn
                1315             1320             1325
Phe Lys Arg Val Asn Asp Ile Tyr Glu Val Asp Gln Ala Gly Glu Gly
                1330             1335             1340
Val Tyr Leu Phe Pro Ser Lys Gln Lys Thr Ser Ser Met Thr Gly Thr
1345             1350             1355             1360
Met Leu Pro Leu Ile Lys Ala Ile Leu Ile Ser Cys Val Ser Asn Lys
                1365             1370             1375
Trp Gln Phe Ile Tyr Leu Leu Tyr Leu Ile Phe Glu Val Ser Tyr Tyr
                1380             1385             1390
Leu His Lys Lys Ile Ile Asp Glu Ile Ala Gly Gly Thr Asn Phe Ile
                1395             1400             1405
```

-continued

```
Ser Arg Leu Val Ala Ala Leu Ile Glu Val Asn Trp Ala Phe Asp Asn
    1410                1415                1420
Glu Glu Val Arg Gly Leu Lys Lys Phe Phe Leu Leu Ser Ser Arg Val
1425                1430                1435                1440
Lys Glu Leu Ile Ile Lys His Lys Val Arg Asn Glu Val Met Val Arg
                1445                1450                1455
Trp Phe Gly Asp Glu Glu Val Tyr Gly Met Pro Lys Leu Val Gly Leu
            1460                1465                1470
Val Lys Ala Ala Thr Leu Ser Lys Asn Lys His Cys Ile Leu Cys Thr
        1475                1480                1485
Val Cys Glu Asp Arg Glu Trp Arg Gly Glu Thr Cys Pro Lys Cys Gly
    1490                1495                1500
Arg Phe Gly Pro Pro Met Thr Cys Gly Met Thr Leu Ala Asp Phe Glu
1505                1510                1515                1520
Glu Lys His Tyr Lys Arg Ile Phe Phe Arg Glu Asp Gln Ser Glu Gly
                1525                1530                1535
Pro Val Arg Glu Glu Tyr Ala Gly Tyr Leu Gln Tyr Arg Ala Arg Gly
            1540                1545                1550
Gln Leu Phe Leu Arg Asn Leu Pro Val Leu Ala Thr Lys Val Lys Met
        1555                1560                1565
Leu Leu Val Gly Asn Leu Gly Thr Glu Val Gly Asp Leu Glu His Leu
    1570                1575                1580
Gly Trp Val Leu Arg Gly Pro Ala Val Cys Lys Lys Val Thr Glu His
1585                1590                1595                1600
Glu Lys Cys Thr Thr Ser Met Met Asp Lys Leu Thr Ala Phe Phe Gly
                1605                1610                1615
Val Met Pro Arg Gly Thr Thr Pro Arg Ala Pro Val Arg Phe Pro Thr
            1620                1625                1630
Ser Leu Leu Lys Ile Arg Arg Gly Leu Glu Thr Gly Trp Ala Tyr Thr
        1635                1640                1645
His Gln Gly Gly Ile Ser Ser Val Asp His Val Thr Cys Gly Lys Asp
    1650                1655                1660
Leu Leu Val Cys Asp Thr Met Gly Arg Thr Arg Val Val Cys Gln Ser
1665                1670                1675                1680
Asn Asn Lys Met Thr Asp Glu Ser Glu Tyr Gly Val Lys Thr Asp Ser
                1685                1690                1695
Gly Cys Pro Glu Gly Ala Arg Cys Tyr Val Phe Asn Pro Glu Ala Val
            1700                1705                1710
Asn Ile Ser Gly Thr Lys Gly Ala Met Val His Leu Gln Lys Thr Gly
        1715                1720                1725
Gly Glu Phe Thr Cys Val Thr Ala Ser Gly Thr Pro Ala Phe Phe Asp
    1730                1735                1740
Leu Lys Asn Leu Lys Gly Trp Ser Gly Leu Pro Ile Phe Glu Ala Ser
1745                1750                1755                1760
Ser Gly Arg Val Val Gly Arg Val Lys Val Gly Lys Asn Glu Asp Ser
                1765                1770                1775
Lys Pro Thr Lys Leu Met Ser Gly Ile Gln Thr Val Ser Lys Ser Thr
            1780                1785                1790
Thr Asp Leu Thr Glu Met Val Lys Lys Ile Thr Thr Met Ser Arg Gly
        1795                1800                1805
Glu Phe Arg Gln Ile Thr Leu Ala Thr Gly Ala Gly Lys Thr Thr Glu
    1810                1815                1820
```

-continued

```
Leu Pro Arg Ser Val Ile Glu Glu Ile Gly Arg His Lys Arg Val Leu
1825                1830                1835                1840

Val Leu Ile Pro Leu Arg Ala Ala Glu Ser Val Tyr Gln Tyr Met
            1845                1850                1855

Arg Gln Lys His Pro Ser Ile Ala Phe Asn Leu Arg Ile Gly Glu Met
            1860                1865                1870

Lys Glu Gly Asp Met Ala Thr Gly Ile Thr Tyr Ala Ser Tyr Gly Tyr
        1875                1880                1885

Phe Cys Gln Met Pro Gln Pro Lys Leu Arg Ala Ala Met Val Glu Tyr
        1890                1895                1900

Ser Phe Ile Phe Leu Asp Glu Tyr His Cys Ala Thr Pro Glu Gln Leu
1905                1910                1915                1920

Ala Ile Met Gly Lys Ile His Arg Phe Ser Glu Asn Leu Arg Val Val
            1925                1930                1935

Ala Met Thr Ala Thr Pro Val Gly Thr Val Thr Thr Thr Gly Gln Lys
            1940                1945                1950

His Pro Ile Glu Glu Phe Ile Ala Pro Asp Val Met Lys Gly Lys Asp
            1955                1960                1965

Leu Gly Ser Glu Tyr Leu Asp Ile Ala Gly Leu Lys Ile Pro Val Glu
        1970                1975                1980

Glu Met Lys Ser Asn Met Leu Val Phe Val Pro Thr Arg Asn Met Ala
1985                1990                1995                2000

Val Glu Thr Ala Lys Lys Leu Lys Ala Lys Gly Tyr Asn Ser Gly Tyr
            2005                2010                2015

Tyr Tyr Ser Gly Glu Asp Pro Ser Asn Leu Arg Val Val Thr Ser Gln
        2020                2025                2030

Ser Pro Tyr Val Val Ala Thr Asn Ala Ile Glu Ser Gly Val Thr
        2035                2040                2045

Leu Pro Asp Leu Asp Val Val Asp Thr Gly Leu Lys Cys Glu Lys
2050                2055                2060

Arg Ile Arg Leu Ser Pro Lys Met Pro Phe Ile Val Thr Gly Leu Lys
2065                2070                2075                2080

Arg Met Ala Val Thr Ile Gly Glu Gln Ala Gln Arg Arg Gly Arg Val
            2085                2090                2095

Gly Arg Val Lys Pro Gly Arg Tyr Tyr Arg Ser Gln Glu Thr Pro Val
        2100                2105                2110

Gly Ser Lys Asp Tyr His Tyr Asp Leu Leu Gln Ala Gln Arg Tyr Gly
        2115                2120                2125

Ile Glu Asp Gly Ile Asn Ile Thr Lys Ser Phe Arg Glu Met Asn Tyr
        2130                2135                2140

Asp Trp Ser Leu Tyr Glu Glu Asp Ser Leu Met Ile Thr Gln Leu Glu
2145                2150                2155                2160

Ile Leu Asn Asn Leu Leu Ile Ser Asp Glu Leu Pro Met Ala Val Lys
            2165                2170                2175

Asn Ile Met Ala Arg Thr Asp His Pro Glu Pro Ile Gln Leu Ala Tyr
            2180                2185                2190

Asn Ser Tyr Glu Thr Gln Val Pro Val Leu Phe Pro Lys Ile Lys Asn
        2195                2200                2205

Gly Glu Val Thr Asp Ser Tyr Asp Asn Tyr Thr Phe Leu Asn Ala Arg
        2210                2215                2220

Lys Leu Gly Asp Asp Val Pro Pro Tyr Val Tyr Ala Thr Glu Asp Glu
2225                2230                2235                2240

Asp Leu Ala Val Glu Leu Leu Gly Leu Asp Trp Pro Asp Pro Gly Asn
```

-continued

```
                2245                2250                2255
Gln Gly Thr Val Glu Thr Gly Arg Ala Leu Lys Gln Val Gly Leu
            2260                2265                2270
Ser Thr Ala Glu Asn Ala Leu Leu Val Ala Leu Phe Gly Tyr Val Gly
        2275                2280                2285
Tyr Gln Ala Leu Ser Lys Arg His Ile Pro Val Val Thr Asp Ile Tyr
        2290                2295                2300
Ser Ile Glu Asp His Arg Leu Glu Asp Thr Thr His Leu Gln Tyr Ala
2305                2310                2315                2320
Pro Asn Ala Ile Lys Thr Glu Gly Lys Glu Thr Leu Lys Glu Leu
            2325                2330                2335
Ala Gln Gly Asp Val Gln Arg Cys Val Glu Ala Met Thr Asn Tyr Ala
        2340                2345                2350
Arg Glu Gly Ile Gln Phe Met Lys Ser Gln Ala Leu Lys Val Lys Glu
        2355                2360                2365
Thr Pro Thr Tyr Lys Glu Thr Met Asp Thr Val Thr Asp Tyr Val Lys
        2370                2375                2380
Lys Phe Met Glu Ala Leu Ala Asp Ser Lys Glu Asp Ile Ile Lys Tyr
2385                2390                2395                2400
Gly Leu Trp Gly Thr His Thr Ala Leu Tyr Lys Ser Ile Ser Ala Arg
            2405                2410                2415
Leu Gly Gly Glu Thr Ala Phe Ala Thr Leu Val Val Lys Trp Leu Ala
        2420                2425                2430
Phe Gly Gly Glu Ser Ile Ala Asp His Val Lys Gln Ala Ala Thr Asp
        2435                2440                2445
Leu Val Val Tyr Tyr Ile Ile Asn Arg Pro Gln Phe Pro Gly Asp Thr
        2450                2455                2460
Glu Thr Gln Gln Asp Gly Arg Lys Phe Val Ala Ser Leu Leu Ala Ser
2465                2470                2475                2480
Ala Leu Ala Thr Tyr Thr Tyr Lys Ser Trp Asn Tyr Asn Asn Leu Ser
            2485                2490                2495
Lys Ile Val Glu Pro Ala Leu Ala Thr Leu Pro Tyr Ala Ala Thr Ala
        2500                2505                2510
Leu Lys Leu Phe Ala Pro Thr Arg Leu Glu Ser Val Val Ile Leu Ser
        2515                2520                2525
Thr Ala Ile Tyr Lys Thr Tyr Leu Ser Ile Arg Arg Gly Lys Ser Asp
        2530                2535                2540
Gly Leu Leu Gly Thr Gly Val Ser Ala Ala Met Glu Ile Met Ser Gln
2545                2550                2555                2560
Asn Pro Val Ser Val Gly Ile Ala Val Met Leu Gly Val Gly Ala Val
            2565                2570                2575
Ala Ala His Asn Ala Ile Glu Ala Ser Glu Gln Lys Arg Thr Leu Leu
        2580                2585                2590
Met Lys Val Phe Val Lys Asn Phe Leu Asp Gln Ala Ala Thr Asp Glu
        2595                2600                2605
Leu Val Lys Glu Ser Pro Glu Lys Ile Ile Met Ala Leu Phe Glu Ala
        2610                2615                2620
Val Gln Thr Val Gly Asn Pro Leu Arg Leu Val Tyr His Leu Tyr Gly
2625                2630                2635                2640
Val Phe Tyr Lys Gly Trp Glu Ala Lys Glu Leu Ala Gln Arg Thr Ala
            2645                2650                2655
Gly Arg Asn Leu Phe Thr Leu Ile Met Phe Glu Ala Val Glu Leu Leu
        2660                2665                2670
```

-continued

Gly Val Asp Ser Glu Gly Lys Val Arg Gln Leu Ser Ser Asn Tyr Ile
              2675                2680                2685

Leu Glu Leu Leu Tyr Lys Phe Arg Asp Ser Ile Lys Ser Ser Val Arg
2690                2695                2700

Glu Met Ala Ile Ser Trp Ala Pro Ala Pro Phe Ser Cys Asp Trp Thr
2705                2710                2715                2720

Pro Thr Asp Asp Arg Ile Gly Leu Pro Gln Asp Asn Phe His Gln Val
              2725                2730                2735

Glu Thr Lys Cys Pro Cys Gly Tyr Lys Met Lys Ala Val Lys Asn Cys
              2740                2745                2750

Ala Gly Glu Leu Arg Leu Leu Glu Glu Gly Ser Phe Leu Cys Arg
              2755                2760                2765

Asn Lys Phe Gly Arg Gly Ser Arg Asn Tyr Arg Val Thr Lys Tyr Tyr
              2770                2775                2780

Asp Asp Asn Leu Leu Glu Ile Lys Pro Val Ile Arg Met Glu Gly His
2785                2790                2795                2800

Val Glu Leu Tyr Tyr Lys Gly Ala Thr Ile Lys Leu Asp Phe Asn Asn
              2805                2810                2815

Ser Lys Thr Ile Leu Ala Thr Asp Lys Trp Glu Val Asp His Ser Thr
              2820                2825                2830

Leu Val Arg Val Leu Lys Arg His Thr Gly Ala Gly Tyr His Gly Ala
              2835                2840                2845

Tyr Leu Gly Glu Lys Pro Asn His Lys His Leu Ile Glu Arg Asp Cys
              2850                2855                2860

Ala Thr Ile Thr Lys Asp Lys Val Cys Phe Leu Lys Met Lys Arg Gly
2865                2870                2875                2880

Cys Ala Phe Thr Tyr Asp Leu Ser Leu His Asn Leu Thr Arg Leu Ile
              2885                2890                2895

Glu Leu Val His Lys Asn Asn Leu Glu Asp Lys Glu Ile Pro Ala Ala
              2900                2905                2910

Thr Val Thr Thr Trp Leu Ala Tyr Thr Phe Val Asn Glu Asp Ile Gly
              2915                2920                2925

Thr Ile Lys Pro Ala Phe Gly Glu Lys Val Thr Leu Glu Met Gln Glu
2930                2935                2940

Glu Ile Thr Leu Gln Pro Ala Val Val Asp Thr Thr Asp Val Ala
2945                2950                2955                2960

Val Thr Val Val Gly Glu Ala Pro Thr Met Thr Thr Gly Glu Thr Pro
              2965                2970                2975

Thr Val Phe Thr Ser Ser Gly Ser Gly Leu Lys Ser Gln Gln Val Leu
              2980                2985                2990

Lys Leu Gly Val Gly Glu Gly Gln Tyr Pro Gly Thr Asn Pro Gln Arg
              2995                3000                3005

Ala Ser Leu His Glu Ala Ile Gln Gly Ala Asp Glu Arg Pro Ser Val
              3010                3015                3020

Leu Ile Leu Gly Ser Asp Lys Ala Thr Ser Asn Arg Val Lys Thr Ala
3025                3030                3035                3040

Lys Asn Val Lys Val Tyr Arg Gly Arg Asp Pro Leu Glu Val Arg Asp
              3045                3050                3055

Met Met Arg Arg Gly Lys Ile Leu Val Val Ala Leu Ser Arg Val Asp
              3060                3065                3070

Asn Ala Leu Leu Lys Phe Val Asp Tyr Lys Gly Thr Phe Leu Thr Arg
              3075                3080                3085

-continued

```
Glu Ala Leu Glu Ala Leu Ser Leu Gly Arg Pro Lys Lys Lys Asn Ile
    3090            3095            3100

Thr Lys Ala Glu Ala Gln Trp Leu Leu Cys Pro Glu Asp Gln Met Glu
3105            3110            3115            3120

Glu Leu Pro Asp Trp Phe Ala Ala Gly Glu Pro Ile Phe Leu Glu Ala
            3125            3130            3135

Asn Ile Lys His Asp Arg Tyr His Leu Val Gly Asp Ile Ala Thr Ile
            3140            3145            3150

Lys Glu Lys Ala Lys Gln Leu Gly Ala Thr Asp Ser Thr Lys Ile Ser
            3155            3160            3165

Lys Glu Val Gly Ala Lys Val Tyr Ser Met Lys Leu Ser Asn Trp Val
            3170            3175            3180

Met Gln Glu Glu Asn Lys Gln Gly Asn Leu Thr Pro Leu Phe Glu Glu
3185            3190            3195            3200

Leu Leu Gln Gln Cys Pro Pro Gly Gly Gln Asn Lys Thr Ala His Met
            3205            3210            3215

Val Ser Ala Tyr Gln Leu Ala Gln Gly Asn Trp Met Pro Thr Ser Cys
            3220            3225            3230

His Val Phe Met Gly Thr Val Ser Ala Arg Arg Thr Lys Thr His Pro
            3235            3240            3245

Tyr Glu Ala Tyr Val Lys Leu Arg Glu Leu Val Glu Glu His Lys Met
            3250            3255            3260

Lys Thr Leu Cys Pro Gly Ser Ser Leu Gly Arg His Asn Asp Trp Ile
3265            3270            3275            3280

Ile Gly Lys Ile Lys Tyr Gln Gly Asn Leu Arg Thr Lys His Met Leu
            3285            3290            3295

Asn Pro Gly Lys Val Ala Glu Gln Leu Cys Arg Glu Gly His Arg His
            3300            3305            3310

Asn Val Tyr Asn Lys Thr Ile Ser Ser Val Met Thr Ala Thr Gly Ile
            3315            3320            3325

Arg Leu Glu Lys Leu Pro Val Val Arg Ala Gln Thr Asp Pro Thr Asn
            3330            3335            3340

Phe His Gln Ala Ile Arg Asp Lys Ile Asp Lys Glu Glu Asn Leu Gln
3345            3350            3355            3360

Thr Pro Gly Leu His Lys Lys Leu Met Glu Val Phe Asn Ala Leu Lys
            3365            3370            3375

Arg Pro Glu Leu Glu Ser Ser Tyr Asp Ala Val Glu Trp Glu Glu Leu
            3380            3385            3390

Glu Arg Gly Ile Asn Arg Lys Gly Ala Ala Gly Phe Phe Glu Arg Lys
            3395            3400            3405

Asn Ile Gly Glu Ile Leu Asp Ser Glu Lys Asn Lys Val Glu Glu Ile
            3410            3415            3420

Ile Asp Asn Leu Lys Lys Gly Arg Asn Ile Lys Tyr Tyr Glu Thr Ala
3425            3430            3435            3440

Ile Pro Lys Asn Glu Lys Arg Asp Val Asn Asp Asp Trp Thr Ala Gly
            3445            3450            3455

Asp Phe Val Asp Glu Lys Lys Pro Arg Val Ile Gln Tyr Pro Glu Ala
            3460            3465            3470

Lys Thr Arg Leu Ala Ile Thr Lys Val Met Tyr Lys Trp Val Lys Gln
            3475            3480            3485

Lys Pro Val Val Ile Pro Gly Tyr Glu Gly Lys Thr Pro Leu Phe Gln
            3490            3495            3500

Ile Phe Asp Lys Val Lys Lys Glu Trp Asp Gln Phe Gln Asn Pro Val
```

```
3505                3510                3515                3520
Ala Val Ser Phe Asp Thr Lys Ala Trp Asp Thr Gln Val Thr Thr Lys
                3525                3530                3535
Asp Leu Glu Leu Ile Arg Asp Ile Gln Lys Tyr Tyr Phe Lys Lys Lys
                3540                3545                3550
Trp His Lys Phe Ile Asp Thr Leu Thr Thr His Met Ser Glu Val Pro
            3555                3560                3565
Val Ile Ser Ala Asp Gly Glu Val Tyr Ile Arg Lys Gly Gln Arg Gly
        3570                3575                3580
Ser Gly Gln Pro Asp Thr Ser Ala Gly Asn Ser Met Leu Asn Val Leu
3585                3590                3595                3600
Thr Met Val Tyr Ala Phe Cys Glu Ala Thr Gly Val Pro Tyr Lys Ser
                3605                3610                3615
Phe Asp Arg Val Ala Lys Ile His Val Cys Gly Asp Asp Gly Phe Leu
                3620                3625                3630
Ile Thr Glu Arg Ala Leu Gly Glu Lys Phe Ala Ser Lys Gly Val Gln
                3635                3640                3645
Ile Leu Tyr Glu Ala Gly Lys Pro Gln Lys Ile Thr Glu Gly Asp Lys
                3650                3655                3660
Met Lys Val Ala Tyr Gln Phe Asp Asp Ile Glu Phe Cys Ser His Thr
3665                3670                3675                3680
Pro Ile Gln Val Arg Trp Ser Asp Asn Thr Ser Ser Tyr Met Pro Gly
                3685                3690                3695
Arg Asn Thr Thr Thr Ile Leu Ala Lys Met Ala Thr Arg Leu Asp Ser
                3700                3705                3710
Ser Gly Glu Arg Gly Thr Ile Ala Tyr Glu Lys Ala Val Ala Phe Ser
            3715                3720                3725
Phe Leu Leu Met Tyr Ser Trp Asn Pro Leu Ile Arg Arg Ile Cys Leu
        3730                3735                3740
Leu Val Leu Ser Thr Glu Leu Gln Val Lys Pro Gly Lys Ser Thr Thr
3745                3750                3755                3760
Tyr Tyr Tyr Glu Gly Asp Pro Ile Ser Ala Tyr Lys Glu Val Ile Gly
            3765                3770                3775
His Asn Leu Phe Asp Leu Lys Arg Thr Ser Phe Glu Lys Leu Ala Lys
                3780                3785                3790
Leu Asn Leu Ser Met Ser Val Leu Gly Ala Trp Thr Arg His Thr Ser
            3795                3800                3805
Lys Arg Leu Leu Gln Asp Cys Val Asn Ile Gly Val Lys Glu Gly Asn
        3810                3815                3820
Trp Leu Val Asn Ala Asp Arg Leu Val Ser Ser Lys Thr Gly Asn Arg
3825                3830                3835                3840
Tyr Ile Pro Gly Glu Gly His Thr Leu Gln Gly Arg His Tyr Glu Glu
                3845                3850                3855
Leu Val Leu Ala Arg Lys Gln Ile Asn Asn Phe Gln Gly Thr Asp Arg
                3860                3865                3870
Tyr Asn Leu Gly Pro Ile Val Asn Met Val Leu Arg Arg Leu Arg Val
            3875                3880                3885
Met Met Met Thr Leu Ile Gly Arg Gly Ala
        3890                3895

(2) INFORMATION FOR SEQ ID NO:3:

(i) SEQUENCE CHARACTERISTICS:
        (A) LENGTH: 375 base pairs
```

(B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

GTATACGAGG TTAGTTCATT CTCGTGTACA TGATTGGACA AATCAAAATC TCAATTTGGT    60

TCAGGGCCTC CCTCCAGCGA CGGCCGAGCT GGGCTAGCCA TGCCCACAGT AGGACTAGCA   120

AACGGAGGGA CTAGCCGTAG TGGCGAGCTC CCTGGGTGGT CTAAGTCCTG AGTACAGGAC   180

AGTCGTCAGT AGTTCGACGT GAGCAGAAGC CCACCTCGAG ATGCTATGTG GACGAGGGCA   240

TGCCCAAGAC ACACCTTAAC CTAGCGGGG TCGTTAGGGT GAAATCACAC CATGTGATGG    300

GAGTACGACC TGATAGGGTG CTGCAGAGGC CCACTATTAG GCTAGTATAA AAATCTCTGC   360

TGTACATGGC ACATG                                                   375

(2) INFORMATION FOR SEQ ID NO:4:

(i) SEQUENCE CHARACTERISTICS:
        (A) LENGTH: 375 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

GTATACGAGG TTAGCTCTTT CTCGTATACG ATATTGGATA CACTAAATTT CGATTTGGTC    60

TAGGGCACCC CTCCAGCGAC GGCCGAAATG GGCTAGCCAT GCCCATAGTA GGACTAGCAA   120

ACGGAGGGAC TAGCCGTAGT GGCGAGCTCC CTGGGTGGTC TAAGTCCTGA GTACAGGACA   180

GTCGTCAGTA GTTCGACGTG AGCACTAGCC CACCTCGAGA TGCTACGTGG ACGAGGGCAT   240

GCCCAAGACA CACCTTAACC CTGGCGGGGG TCGCTAGGGT GAAATCACAT TATGTGATGG   300

GGGTACGACC TGATAGGGTG CTGCAGAGGC CCACTAGCAG GCTAGTATAA AAATCTCTGC   360

TGTACATGGC ACATG                                                   375

(2) INFORMATION FOR SEQ ID NO:5:

(i) SEQUENCE CHARACTERISTICS:
        (A) LENGTH: 376 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

GTATACGAGG TTAGTTCATT CTCGTATACA CGATTGGACA AATCAAAATT TTAATTTGGT    60

TCAGGGCCTC CCTCCAGCGA CGGCCGAGCT GGGCTAGCCA TGCCCATAGT AGGACTAGCA   120

AAACGGAGGG ACTAGCCATA GTGGCGAGCT CCCTGGGTGG TCTAAGTCCT GAGTACAGGA   180

CAGTCGTCAG TAGTTCGACG TGAGCAGAAG CCCACCTCGA GATGCTACGT GGACGAGGGC   240

ATGCCAAGAC ACACCTTAAC CCTAGCGGGG GTCGCTAGGG TGAAATCACA CCACGTGATG   300

GGAGTACGAC CTGATAGGGC GCTGCAGAGG CCCACTATTA GGCTAGTATA AAAATCTCTG   360

CTGTACATGG CACATG                                                  376

(2) INFORMATION FOR SEQ ID NO:6:

(i) SEQUENCE CHARACTERISTICS:
    (A) LENGTH: 229 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "3' NON-CODING REGION OF
        BRESCIA"

(xi) SEQUENCE DESCRIPTION: SEQ ID NO:6:

```
TGAGTGCGGG TGACCCGCGA TCTGGACCCG TCAGTAGGAC CCTATTGTAG ATAACACTAA      60

TTTTTTATTT ATTTAGATAT TACTATTTAT TTATTTATTT ATTTATTGAA TGAGTAAGAA     120

CTGGTACAAA CTACCTCATG TTACCACACT ACACTCATTT TAACAGCACT TTAGCTGGAA     180

GGAAAATTCC TGACGTCCAC AGTTGGACTA AGGTAATTTC TAACGGCCC                 229
```

(2) INFORMATION FOR SEQ ID NO:7:

(i) SEQUENCE CHARACTERISTICS:
        (A) LENGTH: 227 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "3' NON-CODING REGION OF
            ALFORT"

(xi) SEQUENCE DESCRIPTION: SEQ ID NO:7:

```
TGAGCATGGT TGGCCCTTGA TCGGGCCCTA TCAGTAGGAC CCTATTGTAA ATAACATTAA      60

CTTATTAATT ATTTAGATAC TATTATTTAT TTATTTATTT ATTTATTGAA TGAGCAAGTA     120

CTGGTACAAA CTACCTCATG TTACCACACT ACACTCATCT TAACAGCACT TTAGCTGGAG     180

GGAAAATCCT GACGTCCACA GTTGGACTAA GGTAATTTCC TAACGGC                   227
```

(2) INFORMATION FOR SEQ ID NO:8:

(i) SEQUENCE CHARACTERISTICS:
        (A) LENGTH: 244 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "3' NON-CODING REGION OF
            C-STRAIN"

(xi) SEQUENCE DESCRIPTION: SEQ ID NO:8:

```
TGAGCGCGGG TAACCCGGGA TCTGAACCCG CCAGTAGGAC CCTATTGTAG ATAACACTAA      60

TTTTCTTTTT TTTCTTTTTT ATTTATTTAG ATATTATTAT TTATTTATTT ATTTATTTAT     120

TGAATGAGTA AGAACTGGTA TAAACTACCT CAAGTTACCA CACTACACTC ATTTTTAACA     180

GCACTTTAGC TGGAAGGAAA ATTCCTGACG TCCACAGTTG GACTAAGGTA ATTTCTAACG     240

GCCC                                                                  244
```

(2) INFORMATION FOR SEQ ID NO:9:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: other nucleic acid -continued (xi) SEQUENCE DESCRIPTION: SEQ ID NO:9:

TTTTCTTTTT TTT                                                              13

(2) INFORMATION FOR SEQ ID NO:10:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:10:

AGATTGGATC CTAAAGTATT AAGAGGACAG GT                                         32

(2) INFORMATION FOR SEQ ID NO:11:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:11:

TAGTCGGATC CTTAGAATTC TGCGAAGTAA TCTGA                                      35

NUCLEOTIDE AND POLYPEPTIDE SEQUENCES OF PESTIVIRUS STRAINS

This application is a continued prosecution application of an application of the same serial number filed Aug. 17, 1998, now abandoned, which was a continued prosecution application of an application of the same serial number, which was the U.S. national phase of international application PCT/NL95/00214, filed Jun. 16, 1995, the national stage application being now abandoned and having a §102(e) date of Dec. 17, 1996.

FIELD OF THE INVENTION

The invention discloses a method for the construction of a full-length DNA copy of the genome of the C-strain, a classical swine fever vaccine strain, and transcription of RNA thereof which after transfection in cells gives rise to synthesis of infectious C-strain virus. The invention also comprises C-strain derived (pestivirus) vaccines, as well as subunit vaccines against pestivirus and diagnostic means and methods in relation to pestivirus infections. The invention furthermore provides a method of detecting an immunoactive substance in a sample by means of a competitive assay.

BACKGROUND OF THE INVENTION

Classical swine fever (CSF) or hog cholera is a highly contagious and often fatal disease of pigs which is characterised by fever and haemorrhages and can run an acute or chronic course (Van Oirschot. 1986. Hog cholera, p. 289–300. In Diseases of Swine. Iowa State University Press, Ames). Outbreaks of the disease occur intermittently in several European and other countries and can cause large economic losses.

Vaccination of pigs with a live attenuated Classical swine fever virus (CSFV) vaccine strain, the "Chinese" strain (C-strain), protects pigs against CSF (Terpstra and Wensvoort. 1988. Vet. Microbiol. 16: 123–128). A major drawback of vaccinating pigs with the conventional vaccines, of which the C-strain is one, is that these vaccinated pigs cannot be distinguished serologically from pigs infected with a CSFV field strain. The C-strain, however, is considered one of the most effective and safe live vaccines. Addition of a (serological) marker to the C-strain would be highly advantageous and would improve the vaccine.

CSFV is a member of the Pestivirus genus of the Flaviviridae (Francki, R. I. B. et al. 1991. Flaviviridae, p. 223–233. In Fifth report of the International Committee on Taxonomy of Viruses. Archiv. Virol. Suppl. 2, Springer Verlag, Vienna). The other two members of the Pestivirus genus, which are structurally, antigenically and genetically closely related to CSFV, are Bovine viral diarrhoea virus (BVDV) mainly affecting cattle, and Border disease virus (BDV) mainly affecting sheep (Moennig and Plagemann, 1992. Adv. Virus Res. 41: 53–98; Moormann et al., 1990. Virology 177: 184–198; Becher et al. 1994. Virology 198: 542–551).

The genomes of pestiviruses consist of a positive strand RNA molecule of about 12.5 kb (Renard et al. 1985. DNA 4: 429–438; Moormann and Hulst 1988. Virus Res. 11: 281–291; Becher et al. 1994. Virology 198: 542–551). The positive strand RNA genomes of several non-cytopathogenic BVDV strains, however, may be considerably larger (Meyers et al. 1991. Virology 180: 602–616; Meyers et al. 1992. Virology 191: 368–386; Qi et al. 1992. Virology 189: 285–292).

An inherent property of viruses with a positive strand RNA genome is that their genomic RNA is infectious, i.e. after transfection of this RNA in cells that support viral replication infectious virus is produced. As expected, the genomic (viral) RNA of pestiviruses is also infectious (Moennig and Plagemann, 1992. Adv. Virus Res. 41: 53–98).

For several years recombinant DNA technology has allowed in vitro transcription of cloned DNA. This possibility has opened the way to synthesize infectious RNA in vitro from a DNA copy of the genome of a positive strand RNA virus. It is well known in the field of molecular engineering that DNA, in contrast to RNA, is easily manipulated by site directed mutagenesis. Hence, the availability of the technique to produce synthetic infectious RNA has greatly enhanced the study of e.g. replication, virulence, pathogenesis, RNA recombination, vector development, and antiviral strategies of the positive strand RNA viruses. However, application of the technology may cause severe problems. The nature of these problems has been described in a recent review by Boyer and Haenni. 1994. (Virology 198: 415–426). In fact, the success or failure to construct a full-length DNA copy of the genome of a positive strand RNA virus and to produce synthetic infectious RNA from such a full-length DNA copy cannot be reliably predicted.

SUMMARY OF THE INVENTION

The invention provides nucleotide sequences corresponding to a CSFV genome which comprise at least a part of the nucleotide sequence of the CSFV C-strain depicted in SEQ ID No. 1, or a complement or RNA equivalent of such nucleotide sequence, or mutants thereof. Also provided are degenerate nucleotide sequences having different nucleotides but encoding the same amino acids. The invention also covers potypeptides encoded by these nucleotide sequences, and vaccine strains, the genome of which contains such a nucleotide sequence, in particular a recombinant virus strain based on transcripts of a full-length DNA copy of the genome of the CSFV C-strain.

Partial nucleotide sequences as indicated above are also useful, in particular those which contain a mutation in the structural region of the virus genome, i.e. in the nucleotide sequence encoding amino acids 1–1063 of the sequence depicted in SEQ ID No. 1. The mutation may be a substitution by a corresponding part of the genome of another pestivirus strain, a substitution of one or amino acids, or a deletion. The mutation may also be an inserted or substituted heterologous nucleotide sequence altering the translation strategy of the CSFV nucleotide sequence or altering the processing of a polypeptide encoded by the CSFV nucleotide sequence. Furthermore, the mutation may be an inserted or substituted heterologous nucleotide sequence encoding a polypeptide inducing immunity against another pathogen; in this case the CSFV sequence is used as a vector for heterologous immunogens.

The invention is also concerned with nucleotide sequences of a pestivirus genome in general or a part or a mutant thereof, which sequences contain a mutation in a subregion of the E1 protein, i.e. in the nucleotide sequence encoding amino acids corresponding to amino acids 691–750 or 785–870 of the sequence depicted in SEQ ID No. 1, as well as the polypeptides encoded by these nucleotide sequences. These polypeptides are particularly useful for protecting animals against a pestivirus infection in such a way so as to allow a diagnosis which distinguishes between animals infected with field strains of the pestivirus and vaccinated animals.

The invention is furthermore concerned with vaccines containing a nucleotide sequence, a polypeptide, or a vaccine strain as indicated above, as well as to diagnostic compositions containing a nucleotide sequence or a polypeptide as mentioned above, or an antibody raised against such polypeptide.

The invention also relates to methods and means for diagnosis of pestivirus infections, especially with such means and methods which distinguish between infected animals infected and vaccinated animals.

The invention also provides a method for determining test substances, such as an antibody or an antigen in an immunoassay, by means of a specific binding test, wherein a specifically binding reference substance in immobilised form and the same specifically binding reference substance in labeled form are used.

DETAILED DESCRIPTION OF THE INVENTON

The invention provides the complete cDNA sequence of the RNA genome of the "Chinese" strain (C-strain; EP-A-351901) of CSFV. This allows the construction of a full-length DNA copy of this sequence, of which synthetic RNA can be transcribed that after transfection in suitable cells, such as SK6-M cells (Kasza, L. et al. 1972. Res. Vet. Sci., 13: 46–51; EP-A-351901) gives rise to synthesis of infectious C-strain virus. The use of this finding for the development of modified C-strain vaccines, e.g. vaccines which contain a (serological) marker, is described. Although the invention is illustrated for one CSFV strain, it is also applicable and useful for other pestivirus strains by exchanging specific genomic segments, described below, between the other pestivirus and the CSFV C-strain, or by constructing an "infectious", DNA copy of the other pestivirus.

The nucleotide sequence of a DNA copy of the genomic RNA of the C-strain is depicted in SEQ ID No. 1. The numerals mentioned in the text are all related to this sequence and may differ slightly in the sequences of other pestiviruses. The nucleotide sequence is 12,311 nucleotides in length and contains one large open reading frame (ORF) of 11,694 nucleotides encoding a polyprotein of 3,898 amino acids (SEQ ID NO. 2). The size of this ORF is the same as that of the genomes of CSFV strains Brescia (Moormann et al. 1990. Virology 177: 184–198) and Alfort (Meyers et al. 1989. Virology 171: 555–567).

The ORF starts with the ATG at nucleotide positions 374 to 376 and stops at the TGA codon at nucleotide positions 12,068 to 12,070. The 5' non-coding region which precedes the ORF is 373 nucleotides in length. Its sequence is highly conserved between strains Brescia, Alfort and C (SEQ ID NOS:3–5 in FIG. 2A), and the predicted secondary structure of this region resembles that of the 5'non-coding region of hepatitis C virus (Brown et al. 1992. Nucleic Acids Res. 20: 5041–5045), another member of the Flaviviridae. The 5' non-coding region of hepatitis C virus has been shown to contain an internal ribosome entry site (Tsukiyama-Kohara et al. 1992. J. Virol. 66:1476–1483). Such sites have important regulatory functions (Agol. 1991. Adv. Virus. Res. 40:103–180). The analogy with hepatitis C virus indicates that the 5'non-coding region of CSFV also contains an internal ribosome entry site, which is located approximately between nucleotides 124 and 374 of the sequence of SEQ ID No. 1, as important regulatory element. The internal ribosome entry site may be used as a site for mutation in order to attenuate the virus, as well as for altering the translation strategy of the ORF.

A second important region regulating replication of pestiviruses is the 3' non-coding region. Upon alignment of the C-strain sequence with the sequences of strains Brescia and Alfort, a sequence of 13 nucleotides unique to the C-strain was observed in this region (SEQ ID NOS:6–8 in FIG. 2B). This unique sequence TTTTCTTTTTTTT (SEQ ID NO:9) is located from nucleotide positions 12,128 to 12,140 in the sequence of SEQ ID No. 1. It is the only insertion of more than two nucleotides in a row observed in the sequence of the C strain compared to the sequences of strains Brescia and Alfort. For the rest, the sequences in the 3' non-cooding regions of three CSFV strains are highly homologous. The overall homology between sequences in this region is lower when CSFV strains and BVDV strains are compared. Nevertheless, it is clear that the TTTTCTTTTTTT sequence of the C-strain is also absent in the sequences of the 3' non-coding regions of the BVDV strains. The TTTTCTTTTTTT sequence therefore appears to be unique to the genome of the C-strain, and will provide an excellent marker for a C-strain specific sequence. This sequence can be used as a basis for nucleotide probes, and for sequence determination, to identify C-strain specific pestiviruses. Therefore, all pestivirus strains having this sequence in their 3' non-coding region (not necessarily at an identical position as in the C-strain) are considered related to the C-strain, and are also part of the invention.

A crucial parameter for infectivity of transcripts of a DNA copy of the genome of a pestivirus is the amino acid sequence. In this respect, two aspects regarding the cloning and sequencing of RNA viruses in general, and pestiviruses in particular, had to be considered. First, the mutation frequency of the genome of positive strand RNA viruses is high (about $1/10^4$ nucleotides during replication), and therefore no stock of virus or viral RNA preparation is ever clonal with regard to the viral RNA it contains. Among these RNA molecules there may also be molecules which are noninfectious. If this were caused by premature stop codons in the large open reading frame, this would be easily recognised. Also mutations affecting active sites of viral enzymes, or known structures of proteins would be recognizable. However, where the relation between the amino acid sequence and the function and structure of a protein is unknown, which is the case with most of the pestivirus proteins, it is impossible to predict which amino acid is valid and which one is not. Second, mutations may have been introduced during cDNA synthesis. Therefore, the genome of the C-strain was cloned and sequenced independently twice. Regions with discrepancies between the sequences were cloned and sequenced at least thrice (compare FIG. 1). The sequence which was encountered twice at a particular position was regarded as the correct one at that position. The necessity of this approach for the generation of infectious transcripts of a DNA copy of the genome of the C-strain is demonstrated by the following finding. Full-length DNA copy pPRKflc-113, composed after the second round of cloning and sequencing (FIG. 3), appeared to be noninfectious. After cloning and sequencing of regions with discrepancies between the sequences of cDNA clones of the first and second round, there appeared to be five amino acids which were different in the full-length copy of the second round cDNA clones and the sequence of the C-strain considered correct. After correction of these five amino acids in pPRKflc-113, clone pPRKflc-133 was obtained which generated infectious transcripts (FIG. 4). The 5 differences are located at amino acid positions 1414 (Val→Ala); 2718 (Gly→Asp); 2877 (Val→Met); 3228 (Leu→Met); 3278 (Tyr→Glu). The amino acids encoded at these positions by the cDNA sequence which is noninfectious are indicated before the arrow, amino acids at these positions in the copy that is infectious are indicated after the arrow (SEQ ID No. 1). Whether each of the amino acid changes individually will abolish infectivity of the C-strain DNA copy will have to be determined by analysing infectivity of transcripts with individual mutations of each of the five amino acids. However, this finding shows that small differences in the amino acid sequence may be crucial for infectivity of transcripts of a DNA copy of the genome of the C-strain. It also indicates that preparing infectious transcripts of a copy of the sequence of a pestivirus may in practice appear to be impossible because of small differences in sequences (even at the one amino acid level) which may go unnoticed.

C-strain derived mutants that are suitable for (marker) vaccine development are part of the invention. They may contain mutations like deletions, insertions, (multiple) nucleotide mutations, and inserted and/or exchanged genomic fragments originating from other pestivirus strains, in the nucleotide sequence described in SEQ ID No. 1.

The sequence of the C-strain can be divided in four regions suitable for mutation and/or exchange. Region one is the 5' non-coding sequence running from nucleotides 1 to 373. Region two encodes the structural proteins $N^{pro}$-C-E2-E3-E1 and runs from nucleotides 374 to 3563. Region three encodes the nonstructural proteins and runs from nucleotides 3564 to 12068. Region four is the 3' non-coding sequence which runs from nucleotides 12069 to 12311.

One region that is particularly suitable for making C-strain marker vaccines comprises the genomic region encoding the structural proteins $N^{pro}$-C-E2-E3-E1. This region is located between amino acids 1 and 1063 in the sequence of SEQ ID No. 1. Preferred subregions of this part of the genome are specified by the following amino acid sequences 1–168 ($N^{pro}$), 169 to 267 (C), 268 to 494 (E2), 495 to 689 (E3), and 690 to 1063 (E1), or parts thereof. As an example the N-terminal antigenic part of the region encoding E1 of the C-strain, running from amino acid 690 to 877, was exchanged with the corresponding region of E1 of strain Brescia (FIG. 4, pPRKflc-h6). The newly generated C-strain derivative is infectious and can be discriminated from the wild-type strain and from strain Brescia through reaction with C-strain and Brescia specific monoclonal antibodies, directed against E1 and E2; as an example, the resulting C-strain reacts with monoclonal antibodies specific for E1 of strain Brescia (Table 1). Thus, the antigenic properties of this new mutant have changed with respect to the parent virus, demonstrating that exchanging the N-terminal half of E1 of the C-strain with that of another CSFV strain is one approach to the development of a C-strain marker vaccine. However, the invention is not restricted to exchange of N-terminal halves of E1 between the C-strain and other CSFV strains. The N-terminal halves of E1 from any other pestivirus strain may be exchanged with corresponding parts of E1 of the C-strain. In this respect, E1 sequences of pestivirus strains which are isolated from pigs, but belong to an antigenic group other than the C-strain, are particularly suitable. Examples of such strains, which were selected on the basis of cross-neutralisation, include strains "Van EE", "Stam", "SF UK 87", "Wisman", and "5250" (Wensvoort et al. 1989. Vet. Microbiol. 20: 291–306; Wensvoort. 1992. In: Report on meeting of national swine laboratories within the European Community. Jun. 16–17, 1992. VI/4059/92-EN(PVET/EN/1479) 1992, p59–62).

The N-terminal half of E1 has been shown to contain three distinct antigenic domains, A, B and C, located on distinct parts of the E1 protein and each reacting with strongly neutralizing monoclonal antibodies (Wensvoort. 1989. J. Gen. Virol. 70: 2865–2876; Van Rijn et al. 1992. Vet. Microbiol. 33: 221–230; Van Rijn et al. 1993. J. Gen. Virol. 74: 2053–2060). Epitopes conserved among 94 CSFV strains tested, map to domain A, whereas the epitopes of domains B and C are non-conserved (Wensvoort. 1989. J. Gen. Virol. 70: 2865–2876). Mapping of epitopes with hybrids of the E1 genes of strains Brescia and C (Van Rijn et al. 1992. Vet. Microbiol. 33: 221–230), and with deletion mutants of E1 of strain Brescia, suggest that domains A and B+C form two distinct antigenic units in the N-terminal half of E1 (Van Rijn et al. 1993. J. Gen. Virol. 74: 2053–2060). This suggestion was further supported by the finding that the six cysteines located at positions 693, 737, 792, 818, 828, and 856, in the N-terminal half of E1 are critical for the correct folding of E1. However, at least Cys 792 is not crucial for infectivity of strain Brescia, because a monoclonal antibody resistant mutant of this virus was isolated with a Cys→Arg mutation at this position (Van Rijn et al. 1993. Presentation and abstract at the 9th International Congress of Virology, 8–13 August, Glasgow, Scotland).

Whereas small changes in the amino acid sequence may abolish infectivity of the RNA of the C-strain (see Example 2), the cysteine change at position 792 shows that an amino acid change at a position which is less predicted to be suitable for modification without loss of function, may still result in a viable virus mutant. Thus, the effects of a particular amino acid change on the properties of the virus will have to be determined empirically for each amino acid in the sequence of strain C. This again shows that no obvious target sequences for modification of the C-strain, e.g. for marker vaccine development, can be identified on the basis of previously published information.

Essential to the development of C-strain marker vaccines is the possibility to differentiate serologically between vaccinated pigs and pigs infected with a CSFV field strain. It was shown previously that a live attenuated pseudorabies virus vector expressing E1, or immunoaffinity purified E1, expressed in insect cells with a baculovirus vector, induces a protective immune response in pigs against hog cholera (WO 91/00352; Van Zijl et al. 1991. J. Virol. 65: 2761–2765; Hulst et al. 1993. J. Virol. 67: 5435–5442). It was surprisingly found that mutants of E1 with a deleted A domain or with deleted B+C domains (FIG. 5), also induce a protective immune response in pigs against hog cholera (Table 2). This indicates that protective immunity induced by the vaccine strain does not depend on neutralizing antibodies against both domains A and B+C. Therefore, pestivirus strain mutants having exchanged or mutated only the A domain, or only the B+C domains, or parts thereof, with the corresponding region of another pestivirus, preferably but not exclusively a pestivirus isolated from pigs belonging to a different antigenic group than the C-strain (for examples see above), are also part of the invention. The region of E1 covering domain A and suitable for exchange or mutation, is located between amino acids 785 and 870. Parts of this region may also be suitably exchanged or mutated, e.g. the subregions located between amino acids 785 and 830 and between amino acids 829 and 870. The region of E1 covering domains B+C and suitable for exchange or mutation is located between amino acids 691 and 750. Parts of this region may also be suitably exchanged or mutated, e.g. the subregions located between amino acids 691 and 718 and between amino acids 717 and 750.

Animals infected with pestiviruses develop antibodies against E2 (Kwang et al., 1992. Vet. Microbiol. 32: 281–292; Wensvoort. unpublished observation). Therefore, a second region suitable for (marker) vaccine development via mutation (deletions, insertions, point mutations), or exchange of corresponding genetic material with an antigenically different pestivirus, or with a pestivirus belonging to a different antigenic group, is the region encoding E2.

The C-strain may also be used as a vector for the insertion and expression of heterologous genetic material (sequences). For vector development, heterologous genetic material inserted into the C-strain serves to alter translation strategy of the large ORF and processing of the polyprotein encoded by this ORF. An example of a sequence suitable for altering the translation strategy of the large ORF is a sequence specifying an Internal Ribosome Entry Site (IRES) (Duke et al. 1992. J. Virol. 66: 1602–1609, and references therein). An example of a sequence suitable for altering processing of the polyprotein is a signal sequence responsible for translocation of proteins exported from the cell or inserted into membranes, across the membrane of the endoplasmatic reticulum (Blobel. 1980. Proc. Natl. Acad. Sci. U.S.A. 77: 1496–1500; Kreil. 1981. Annu. Rev. Biochem. 50: 317–348). Signal sequences are cleaved by cellular signal peptidases. However, sequences encoding cleavage sites of viral proteases may as well be used to alter processing of the polyprotein.

Sequences inserted and expressed by a C-strain vector may be used as a marker to identify vaccinated pigs, or may be used to protect pigs against the pathogen from which the heterologous inserted sequence originates. Marker sequences are preferably highly antigenic and belonging to microorganisms not replicating in pigs. They may encode known complete gene products (e.g. capsid or envelope proteins) or antigenic parts of these gene products (e.g. epitopes). Preferably marker sequences originate from viruses belonging to the families: Adenoviridae, Arenaviridae, Arteriviridae, Bunyaviridae, Caliciviridae, Circoviridae, Coronaviridae, Flaviviridae, Hepadnaviridae, Herpesviridae, Orthomyxoviridae, Paramyxoviridae, Papovaviridae, Rhabdoviridae, Parvoviridae, Poxviridae, Picornaviridae, Reoviridae, Retroviridae, and Togaviridae. However, marker sequences may also encode artificial antigens not normally encountered in nature, or histochemical markers like *Escherichia coli* β-galactosidase, Drosophila alcohol dehydrogenase, human placental alkaline phosphatase, firefly luciferase, and chloramphenicol acetyltransferase.

Heterologous genetic material encoding one or more proteins inducing protective immunity against disease caused by the pathogen corresponding with the heterologous genetic material may be derived from other pestivirus strains, including sequences of strains specified above, porcine parvovirus, porcine respiratory coronavirus, transmissible gastro-enteritis virus, porcine reproductive and respiratory syndrome virus (Lelystad virus, EP. 92200781.0), Aujeszky's disease virus (pseudorabies virus), porcine endemic diarrhoea virus, and porcine influenza virus, and bacteria, such as *Pasteurella multocida, Bordetella bronchiseptica, Actinobacillus pleuropneumoniae, Streptococcus suis, Treponema hyodysenteria, Escherichia coli*, Leptospira, and mycoplasmata, such as *M. hyopneumoniae* and *M. lyorhinis*.

Suitable sites for insertion of heterologous sequences in the C-strain, but not the only ones, are located between amino acid residues 170 and 171, between residues 690 and 691, and between residues 691 and 692 and are indicated in SEQ ID No. 1.

The invention also includes diagnostic tests which can be used to discriminate between pigs vaccinated with a marker vaccine, or a subunit vaccine containing (mutated) E1 and/or (mutated) E2, and pigs infected with a pestivirus field strain. Suitable forms of such differential diagnostic tests are described in Examples 4 and 5. In the conventional non-discrimiminatory CSFV ELISA test, E1 is used as antigen in the complex trapping blocking (CTB) ELISA assay described by Wensvoort et al., 1988. (Vet. Microbiol. 17:129–140). This prior art CTB-ELISA, also called Liquid Phase Blocking ELISA, or double antibody sandwich ELISA, uses two monoclonal antibodies (Mabs) which were raised against E1 of CSFV strain Brescia. The epitope for Mab b3, which is located within domain A, is conserved among CSFV strains, whereas the epitope of Mab b8, which is located within domain C, is nonconserved (Wensvoort. 1989. J. Gen. Virol. 70: 2865–2876). The above CTB-ELISA is sensitive, reliable and specifically detects CSFV specific antibodies in pigs infected with a pestivirus. Thus, the test differentiates between pigs infected with a CSFV strain and pigs infected with e.g. a BVDV strain. However, the test does not differentiate between pigs infected with a CSFV field strain and pigs vaccinated with the C-strain vaccine. Also this test is not suitable in conjunction with an E1 subunit vaccine whether live or dead.

One test according to the invention is a modfied CTB-ELISA, based on only one MAb, e.g. MAb b3. Such a CTB-ELISA, based on only one Mab which Mab is used for binding of the antigen to the surface of an ELISA plate as well as competition with a field serum has not yet been described and is an essential part of this invention. Now that the principle of this test has been described, it can be usefully applied to the development of diagnostic kits for the detection of other antibodies including antibodies against other viruses or other diseases, or antibodies which are indicative for other conditions of the human or animal body. The finding is therefore useful for all CTB-ELISA's, or ELISA's based on the same principle as a CTB-ELISA, which are developed on the basis of a single Mab and a dimerised or multimerised antigen. The claimed test method is also applicable to the determination of other members of pairs of specifically binding partner molecules, such as activators/receptors, enzymes/inhibitors and the like, wherein one of the partners has at least two identical binding sites.

Thus the invention also comprises a method of determining the presence of a test substance (e.g. antibody) capable of specifically binding with a binding site of a binding partner (e.g. antigen), in a sample, by means of competition of said test substance with a measurable amount of a reference substance (antibody) capable of specifically binding with the same binding site of said binding partner, comprising (1) contacting said sample with (a) said reference substance (antibody) bound to a solid carrier, (b) the binding partner (antigen) of said reference substance, said binding partner molecule containing at least two identical binding sites for said reference substance, and (c) said reference substance (antibody) provided with a label;

(2) measuring the degree of separation of said label from said carrier.

As an example, said binding partner (antigen) to said reference substance (antibody), containing at least two identical binding sites is a dimer of a binding partner (antigen) to said reference substance.

Using the same principle, the invention also comprises a method of determining the presence of a test substance (antigen) having at least two identical binding sites per molecule for specifically binding with a binding partner (antibody), in a sample, comprising (1) contacting said sample with (a) said binding partner (antibody) bound to a solid carrier, and (b) said binding partner (antibody) provided with a label;

(2) measuring the degree of binding of said label to said carrier.

In these methods, the antibodies and antigens are only referred to by way of example; they may be substituted by other specifically binding partner molecules.

Further provided is a diagnostic kit containing: (a) a reference monoclonal antibody bound to a solid carrier, (b) said reference monoclonal antibody provided with a label; and optionally (c) an antigen to said reference antibody containing at least two identical binding sites for said reference antibody; or a complex between said components (a) and/or (b) and (c); as well as further components for carrying out a competitive immunological assay.

The method is suitable as a differential diagnostic test in conjunction with an E1 subunit vaccine, which has a deletion in one or more epitopes of E1, e.g. domain A. The test is also suitable in conjunction with subunit E1 of which the A domain has been mutated such that antibodies induced against such mutated A domain do not compete with Mab b3 for the epitope of Mab b3. Furthermore, the test is suitable in conjunction with a modified C-strain or other CSFV strain vaccines with a deletion in domain A, with a domain A which has been exchanged with that of a pestivirus belonging to a different antigenic group as CSFV (see above), or with a domain A which has been mutated such that antibodies directed against that domain do not compete with Mab b3 for the epitope of Mab b3. Although the test is described and exemplified for domain A of E1, a similar test based on only Mab b8 can be used in conjunction with a vaccine with a deletion in domains B+C or domain C, with domain B+C or domain C which has been exchanged with that of a pestivirus belonging to a different antigenic group as CSFV (see above), or with domain B+C or domain C which has been mutated such that antibodies directed against those domains do not compete with Mab b8 for the epitope of Mab b8. The test is illustrated in conjunction with Mab b3 or Mab b8 of strain Brescia. However, the test may be usefully set up with other Mabs directed against domain A or domains B+C of E1 of strain Brescia or against domain A or domains B+C of any other CSFV strain, but also with Mabs against analogous domains in E1 of any other pestivirus. The test can also be based on epitopes of E2 (see Example 5). Antigens suitable in the (modified) CTB-ELISAs according to the invention are preferably dimers or multimers of E1 (plus or minus a 3'-TMR) or E2 (see Example 5) of CSFV strains reacting with Mab b3 or Mab b8 or similar MAbs directed against E2 epitopes. In the case of a vaccine with a mutated A domain, dimers or multimers of the antigen used for the diagnostic test may be synthesised by the deletion B+C construct (see Example 5), or in the case of a vaccine with mutated B+C domains, dimers or multimers of the antigen used for the diagnostic test may be synthesised by the deletion A construct (compare FIG. 5 for constructs; compare Examples 4 and 5). The dimerised (or multimerised) form of the E1 antigen is believed to be based on disulphide bridges formed by cysteine residues in the C-terminal part of E1. It allows a very sensitive immunoassay, as the dimerised antigen molecule contains two copies of the epitope of one Mab. Thus, this one Mab can be used for immobilising the dimerised antigen via one epitope, and for labeling the dimerised antigen via the other epitope. Competition by sample serum antibodies raised as a result of field strain infection inhibits binding of the labeled antibody to the antigen, and thus results in a sensitive test for the presence of such antibodies. The invention also relates to diagnostic kits based on this method, which kit comprises E1- or E2-based antigens, and (enzyme-) labeled and immobilised monoclonal antibodies of the same type directed at an E1 or E2 epitope, as well as further conventional components (plates, diluents, enzyme substrate, colouring agents, etc.) for carrying out an immunoassay of the competition type.

The vaccine according to the invention contains a nucleotide sequence as described above, either as such or as a vaccine strain or in a vector or host organism, or a polypeptide as described above, in an amount effective for producing protection against a pestivirus infection. The vaccine can also be a multipurpose vaccine comprising other immunogens or nucleotides encoding these. The vaccines can furthermore contain conventional carriers, adjuvants, solubilizers, emulsifiers, preservatives etc. The vaccines according to the invention can be prepared by conventional methods.

The method of the invention for the production of infectious transcripts of a full-length DNA copy of the genome of a CSFV strain, the C-strain, is useful for any other C-strain derived, or pestivirus strain. The method, described here for a live attenuated CSFV vaccine strain, may also be very usefully applied to in vitro attenuate (modify) the C-strain or any other CSFV or pestivirus strain, for vaccine purposes.

The C-strain vaccine according to the invention allows serological discrimination between vaccinated pigs and pigs infected with a CSFV field strain. Marker vaccines of any other CSFV-strain or pestivirus strain may equally well be obtained using the methods of the invention. Such marker vaccines may be developed for instance by mutating (deletions, point mutations, insertions) the region encoding E1, or the N-terminal half of E1, or domains A or B+C of E1. or the region encoding E2 of the C-strain, or analogous regions in the genomes of C-strain derived, or other pestivirus strains, or by exchanging these regions with the corresponding regions of antigenically different pestiviruses or of pestiviruses belonging to a different antigenic group.

An alternative approach to the development of a C-strain marker vaccine is to add to its genome heterologous genetic material expressing a highly antigenic protein or epitope(s) of a microorganism not replicating in pigs, or of artificial nature and not normally occurring in pigs.

Furthermore such heterologous genetic material may encode antigens inducing protective immunity against a disease caused by a microorganism pathogenic for pigs. Therefore, application of the C-strain, or strains derived from the C-strain, or whatever other pestivirus strain, as a vector for the expression of heterologous antigens inducing protection against a particular disease in a host organism, the host organism being a mammal, is also part of the invention. The construction of recombinant C-strain viruses expressing heterologous sequences and suitable sites for insertion of these heterologous sequences are described above. Analogous recombinant viruses can be made for C-strain derived viruses, or for any other pestivirus. These viruses are therefore also part of the invention.

An essential part of the invention relates to the immunogenic potential of subunit E1 with deletions in domain A, or domains B+C. As summarised in Table 2, both of these mutant E1s are capable of inducing protective immunity in pigs against challenge with a lethal dose of the highly virulent Brescia strain. The use of mutants of E1 containing deletions or other mutations in domains A and B+C as dead subunit vaccine, or as live subunit vaccine expressed by a vector system in the vaccinated animal. against CSF, is also part of the invention. Also mutated E1 together with other antigenic CSFV proteins, e.g. E2 or a mutated form of E2. is suitable as dead or live subunit vaccine (see above).

The invention also includes diagnostic tests which can be used to discriminate between pigs vaccinated with a CSFV marker vaccine, or a subunit vaccine containing (mutated) E1 and/or (mutated) E2, and pigs infected with a pestivirus field strain. Such a diagnostic test may be based on serology, antigen detection, or nucleic acid detection. The choice which test is appropriate in a given case is amongst others dependent on the specificity of the marker used. One suitable form of a serological diagnostic test is the modified CTB-ELISA, described in example 4. According to the invention, this method, based on a CTB-ELISA using a single antibody, is not restricted to the use in the context of CSFV or other pestiviruses, but is also applicable to the determination of other antibodies for other diagnostic purposes in the human or animal field, as well as to the determination of other specifically binding substances.

An example of a suitable antigen detection test in conjunction with a C-strain marker vaccine is a test detecting CSFV field strain E1 and not vaccine strain E1 in the blood of pigs. If the A domain of the C-strain has been modified by e.g. exchange of this domain with that of a pestivirus strain belonging to a different antigenic group than CSFV, such a test may be based on monoclonal antibodies recognizing conserved epitopes of the A domain of CSFV.

However, if the E2 region of the C-strain is modified for marker vaccine development, a serological or antigenic diagnostic test accompanying such a vaccine detects differences between vaccinated and infected animals, in relation to the modified E2 region. Such a diagnostic test thus uses E2 specific sequences as an antigen. These E2 specific sequences may originate from the parent C-strain (see example 5), from CSFV strains which are antigenically different from the C-strain, or from pestiviruses belonging to a different antigenic group than CSFV. However, these E2 specific sequences may also be obtained via mutation (deletion(s), insertion(s), or point mutation(s)) of native E2 of any pestivirus, or may consist of (mutated) parts of E2 of any pestivirus. Dimeric E2 and multimeric E2 may be used as antigen in a diagnostic test (see example 5). Also E2 in conjunction with one monoclonal antibody (oompare Examples 4 and 5) may be used in a CTB-ELISA test, the principle of which has been described above. A diagnostic test based on E2 is described in Example 5. Where an antigen detecting kit is to detect pestivirus E2 and is based on one Mab, such test kist preferably contains an antibody recognising a conserved epitope on E2. Such tests are also part of the invention.

Finally, a diagnostic test may be based on the specific detection of a region of CSFV field strains which is modified in the C-strain. Suitable techniques for this test include nucleic acid hybridisation, e.g. with specific probes, and/or amplification, e.g. with the polymerase chain reaction. Alternatively, C-strain sequences may be distinguished from CSFV field strain sequences by PCR amplification of (a part of the 3' non-coding region containing the TTTTCTTTTTTTT sequence unique to the C-strain genome.

If the C-strain is modified by insertion of a heterologous marker sequence, any form of a diagnostic test based on this sequence, e.g. based on the antigen, epitope(s), or histochemical product encoded by this sequence, or based on detection of the heterologous genetic information via nucleic acid hybridisation techniques, e.g. specific probes, and/or amplification techniques, like the polymerase chain reaction, is also part of the invention.

EXAMPLE 1

Molecular Cloning and Sequencing of the Genome of the C-strain

Cells and virus Swine kidney cells (SK6-M, EP-A-351901) were grown in Eagle's basal medium containing 5% fetal bovine serum (FBS) and antibiotics. FBS was tested for the presence of BVDV and BVDV antibodies as described (Moormann et al. 1990. Virology 177: 184–198). Only sera free from BVDV and BVDV antibodies were used. The "Chinese" vaccine strain (C-strain) of Classical swine fever virus (CSFV) was adapted to SK6-M cells as described in EP-A-351901. The strain designated "Cedipest" is noncytopathic and was biologically cloned by threefold endpoint dilution. After three amplification steps a cloned virus stock with a titer of $3,5.10^6$ $TCID_{50}$/ml was produced.

Isolation of Cytoplasmic RNA of SK-6 Cells Infected with the C-strain.

Intracellular RNA from cells infected with the C-strain was isolated essentially as described (Moormann et al. 1990. Virology 177: 184–198). Briefly, monolayers of SK6-M cells in 162 cm$^2$ bottles (Costar) were infected with Cedipest at a multiplicity of infection (m.o.i.) of 5 $TCID_{50}$ per cell. Subsequently, cells were incubated for 1.5 hr at 37° C., and fresh medium was added to a final volume of 40 ml. After 7 hrs Actinomycin D was added to a final concentration of 1 $\mu$g/ml. After 24 hrs cells were washed twice with ice cold phosphate buffered saline (PBS), and lysed in ice-cold lysisbuffer (50 mM Tris-HCl pH 82, 0.14 M NaCl, 2 mM MgCl$_2$, 5 mM DTT, 0.5% [v/v] NP-40, 0.5% [w/v] Na-deoxycholate, and 10 mM vanadyl ribonucleoside complexes (New England Biolabs)). The lysates were centrifuged (4° C., 5 min., 4000 g) and the supernatant was treated with proteinase K (250 $\mu$g/ml, final concentration) for 30 min. at 37° C. extracted twice with phenol, chloroform, and isoamyl alcohol (49:49:2), and extracted once with chloroform and isoamyl alcohol (24:1). RNA was stored in ethanol.

Synthesis and Amplification of cDNA

One to two $\mu$g of cytoplasmic RNA of cells infected with the C-strain, and 20 pmol (−)sense primer were incubated with 1 $\mu$l 10 mM methylmercury hydroxide for 10 min. at room temperature. The denaturated RNA was then incubated with 1 $\mu$l 286 mM β-mercaptoethanol for 5 min. at room temperature. The RNA was reverse transcribed with 200–400 units M-MLV reverse transcriptase deficient of RNase H (Promega) for 45 min. at 42° C. in 1×M-MLV reverse transcriptase buffer (50 mM Tris-HCl pH 8.3. 75 mM KCl, 3 mM MgCl$_2$ and 10 mM DTT), 40 U rRNasin (Promega), and 80 $\mu$M of dATP, dGTP, dCTP and dTTP. The final reaction volume was 25 $\mu$l. The samples were overlaid with 30 $\mu$l of mineral oil (Sigma).

After reverse transcription (RT) the samples were denaturated for 10 min. at 94° C. Portions of 2.5 $\mu$l of each RT-reaction were amplified in a polymerase chain reaction (PCR) of 39 cycles (cycle: 94° C., 60 sec.; 55° C., 60 sec. and 72° C., 1–2 min.) in 100 $\mu$l Taq polymerase buffer (supplied by the manufacturer of Taq polymerase) containing 1 $\mu$M of the (+) as well as the (−) sense primer, 200 $\mu$M of each of the four dNTPs, and 2.5 U Taq DNA polymerase (Boehringer Mannheim). The samples were overlaid with 75 $\mu$l of mineral oil (Sigma).

Cloning of cDNA Covering the Complete Genome of the C-strain

The genome of the C-strain was cloned indepently twice. During the first round of cloning (FIG. 1A), primers for first strand cDNA synthesis and PCR were selected on the basis of homology between the sequences of the CSFV strains Brescia (Moormann et al. 1990. Virology 177: 184–198) and Alfort (Meyers et al. 1989. Virology 171:555–567), and the BVDV strains Osloss (Renard et al. EP 0208672) and NADL (Collett et al. 1988. Virology. 165: 191–199). The sizes of the cDNA fragments were chosen between 0.5–2.5 kb in order to obtain optimal amplification. Gel purified amplification products were treated with T4 DNA potymerase and Klenow DNA polymerase I, and phosphorylated with T4 polynucleotide kinase. Thereafter, cDNA fragments were ligated with T4 ligase into the SmaI site of pGEM4z-blue.

In the second round of cloning (FIG. 1B), primers were selected from the sequence of the cDNA clones obtained after the first round of cloning. Where possible, primers contained restriction sites suitable for cloning of the amplified cDNA fragments. After RT and PCR amplification (see above), cDNA fragments were either cut with two different restriction enzymes, or blunted and phosphorylated (as described above) at one end, and digested with a suitable restriction enzyme at the other end. If it was not possible to use PCR introduced restriction sites located in the primers, a site within the amplified cDNA fragment was chosen for cloning. After gel purification, PCR products were ligated into gel purified pGEM4z-blue (Promega) or pGEM5zf(+) (Promega), digested with restriction enzymes creating ends compatible with those of the PCR products.

To obtain cDNA clones containing the ultimate 5' and 3' ends of the genome of the C-strain, we used the 3'–5' ligation method (Mandl et al. 1991. Journal of Virology 65:4070–4077). Cytoplasmic RNA was isolated from cells infected with the C-strain as described above, and was further purified through a 5.7 CsCl cushion (Moormann and Hulst. 1988. Virus Res. 11: 281–291). Based on results suggesting that there is no Cap structure at the 5' end of the BVDV genome (Brock et al. 1992. J. Virol. Meth. 38: 39–46), genomic RNA of the C-strain was ligated without previous treatment with pyrophosphatase. Eight $\mu$g of RNA was ligated in a reaction mix of 50 mM Tris-HCl pH 8.0, 10 mM MgCl2, 10 mM DTT, 20 U rRNasin (Promega), 10 $\mu$g/ml BSA (RNase free) and 1 mM ATP, using 10 U of T4 RNA ligase (New England Biolabs). The mixture was incubated for 4 hrs at 37° C. RNA was extracted with phenol/chloroform, precipitated with ethanol, pelleted, and resuspended in RNase-free water. Portions of 2 $\mu$g RNA were reverse transcribed and amplified as described above. Portions of 2 $\mu$l of each PCR were reamplified using a nested set of primers. For reverse transcription, a (−)sense primer was used hybridizing to the 5' noncoding region. For the two PCR amplification steps we used (+)sense primers hybridizing the 3' noncoding region and (−)sense primers hybridizing to the 5' noncoding region. After extraction with phenol/chloroform and ethanol precipitation, PCR products were digested with NcoI (incorporated in the (+)sense primer used in the nested PCR) and EagI (nucleotide 81 in the sequence of SEQ ID No. 1), and ligated into the NcoI-EagI sites of pUC21 (Vieira and Messing. 1991. Gene 100: 189–194).

All modification and cloning procedures used in Example 1 were carried out essentially as described (Sambrook et al. 1989. Molecular cloning: A Laboratory Manual. Cold Spring Harbor Laboratory, Cold Spring Harbor, N.Y.). Restriction enzymes and DNA modifying enzymes were commercially purchased and used as described by the suppliers. Plasmids were transformed and maintained in *Escherichia coli* strain DH5α (Hanahan. 1985. in DNA cloning 1: 109–135).

Sequencing of cDNA Clones.

Plasmid DNA used for sequencing was extracted and purified either by alkaline lysis and LiCl precipitation, or by CsCl centritugation (Sambrook et al. 1989. Molecular loning: A Laboratory Manual. Cold Spring Harbor Laboratory, Cold Spring Harbor, N.Y.). The T7 polymerase based sequencing kit (Pharmacia) was used for direct double stranded sequencing of plasmid DNA. In addition to the SP6, T7, and universal pUC/M13 forward and reverse primers, oligonucleotide primers were used based on the sequence of CSFV strain Brescia (Moormann et al. 1990. Virology 177: 184–198). Primers were synthesised with a Cyclone DNA synthesizer (New Brunswick Scientific) or with a 392 DNA/RNA synthesizer (Applied Biosystems). Sequence reactions were analysed on a 6% acrylamide gel containing 8 M urea. Sequence data were analysed with a Compaq 386 computer using Speedreader hardware, and PCgene software (Intelligenetics Inc, Applied Imaging Corp., Geneva, Switzerland) and with an Apple Macintosh computer using the program MacMollytetra.

Considering the possibility of sequence errors or differences caused by Taq polymerase or heterogeneity of C-strain RNA, the entire genomic sequence of cDNA clones of the C-strain was determined by sequencing a minimum of two cDNA clones, obtained after independent PCR reactions. If differences were observed between the nucleotide sequences of two clones of a particular region, the consensus nucleotide sequence of that region was determined by sequencing a third cDNA clone obtained after another independent PCR reaction (FIG. 1A).

EXAMPLE2

Generation of Infectious Transcripts of 8 Full-length DNA Copy of the Genome of the C-strain Construction of cDNA Clone pPRKflc-113.

A full-length DNA copy of the genomic RNA of the C-strain was composed according to the scheme depicted in FIG. 3. First, two subciones, one (pPRc64) containing the cDNA sequence of the 5' half of the genome (nucleotides 1–5,560), and the other (pPRc111) containing the cDNA sequence of the 3' half of the genome (nucleotides 5,463–12, 311) were constructed. Initially construction of the full-length cDNA clone was tried in pGEM4z-blue. However, this approach failed because of instability of the full-length insert in this vector. To increase stability of the clones, inserts of the 5' and 3' half clones were recloned in a derivative of the low copy number vector pOK12 (Vieira and Messing. 1991. Gene 100: 189–194), resulting in pPRc108 and pPRc123, respectively. To this end pOK12 was modified by deleting most of the restriction sites of the multiple cloning site (MCS), and the T7 promoter sequence. The resulting vector, pPRK, which was used for all further full-length cloning, still contains unique SpeI, NotI, EagI, BamI, EcoRI, EcoRI, and XbaI sites in the MCS.

In detail, the construction of full-length clone pPRKflc-113 proceeded as follows (FIG. 3). Inserts of plasmids pPRc45 and pPRc46 were joined at the HpaI site, located at nucleotide position 1249 in the sequence of the C-strain (SEQ ID No. 1), resulting in plasmid pPRc49. The insert of pPRc49 was subsequently joined with the insert of pPRc44 at the NsII site located at nucleotide position 3241 (SEQ ID No. 1), resulting in pPRc63. The 5' half clone pPRc64 (nucleotide 1 to 5560, SEQ ID No. 1) was constructed by joining the insert of pPRc63 with an amplified (PCR) cDNA fragment of the ultimate 5' region of the genomic RNA of the C-strain as follows. A 5' end (+)sense primer was synthesised containing an EcoRI and a SalI site followed by the T7 RNA polymerase promoter sequence and the first 23 nucleotides of the genomic RNA of the C-strain. This primer and a (−) sense primer of the second round of cloning were used to amplify a cDNA fragment that was digested with EcoRI and XhoI cloned into EcoRI-XhoI (nucleotide 216 in SEQ ID No. 1) digested pPRc63. Finally, the insert of pPRc64 was recloned into EcoRI-XbaI digested pPRK resulting in pPRc108.

The 3' half clone pPRc111 (nucleotide 5,463 to 12,311, SEQ ID No. 1) was constructed by joining 4 second round clones (pPRc67, 53, 58, and 55) and one first round clone (pPRc14). The inserts of pPRc67 and pPRc53 were joined at the NheI site located at nucleotide position 7,778, resulting in pPRc71. The inserts of pPRc55 and pPRc58 were joined at the ApaI site located at nucleotide position 10,387, resulting in pPRc65. The inserts of pPRc65 and pPRc14 were subsequently joined at the AflIII site at nucleotide position 11,717, resulting in pPRc73. The insert of pPRc73 was joined with the insert of pPRc71 at the PstI site located at nucleotide position 8,675, resulting in pPRc79. Then, the insert of pPRc79, which contains the complete 3' terminal sequence of the cDNA of the C-strain, was modified such that an SrlI site was introduced which after digestion generated the exact 3' end of the C-strain cDNA sequence (for exact run-off transcription at the 3'end). To achieve this, a 3' end (−)sense primer was synthesised containing an SrlI and an XbaI site and 18 nucleotides complementary to the 3' terminal sequence of the genomic RNA of the C-strain. This primer and a (+)sense primer of the first round of cloning were used to amplify a cDNA fragment. This fragment was digested with SpeI (nucleotide position 11,866, SEQ ID No. 1) and XbaI and cloned into SpeI-XbaI digested pPRc79, resulting in pPRc111.

Full-length cDNA clone pPRKflc-113, finally, was constructed by inserting the C-strain specific NcoI$^{5532}$-XbaI$^{mcs}$ fragment of pPRc111 into NcoI$^{5532}$-XbaI$^{mcs}$ digested pPRc108.

Construction of Full-length Clone pPRKflc-133.

Full-length cDNA clone pPRKflc-113 still had, besides silent nucleotide mutations, 5 point mutations leading to amino acid changes compared to the amino acid sequence determined from the sequence of at least two first round cDNA clones. These 5 point mutations in pPRKflc-1 13 were changed to the predominant sequence (2 out of 3) through exchange of affected DNA fragments with corresponding DNA fragments containing the predominant sequence.

The 5' half cDNA clone pPRc108, with a point mutation at nucleotide position 4,516, was changed by replacing the ScaI$^{3413}$-NcoI$^{5532}$ fragment of pPRc108 with that of pPRc124. Clone pPRc124 was made by exchanging the PvuII$^{4485}$-NheI$^{5065}$ fragment of pPRc44 by the corresponding fragment of pPRc32 (compare FIG. 1). The new 5' half cDNA clone was designated pPRc129.

For cloning purposes a 3' half clone was constructed by deleting the 5' part of the C-strain sequence of pPRKflc-113 from the SalI site in the vector (compare FIG. 3) up to the HpaI site at nucleotide position 5,509 (SEQ ID No. 1), resulting in pPRc123. In pPRc123 mutations at nucleotide positions 8,526, 9,002, 10,055, and 10,205 had to be changed. The mutation at position 8,526 was restored in two steps. First, the ApaI$^{8,506}$-PstI$^{8,675}$ fragment of pPRc53 was exchanged with that of pPRc90, resulting in pPRc125. Second, the NheI$^{7,378}$-PstI$^{8,675}$ fragment of pPRc123 was exchanged with that of pPRc125, resulting in pPRc127.

To be able to restore the 3 mutations at positions 9,002, 10,055, and 10,205, we first modified pPRc58 such that the FspI site in the vector was deleted. To this end the EcoRI$^{mcs}$-NdeI fragment of pPRc58 was deleted (NdeI cuts in pGEM4z-blue), resulting in pPRc126. Plasmid pPRc126 was used for restoring the mutations at positions 10,055 and 10,205 by replacing its SacI$^{9,975}$-ApaI$^{10,387}$ fragment with the corresponding fragment of pPRc96, resulting in pPRc128. The mutation at position 9002 was restored by replacing the AatII-FspI$^{9016}$ (AatII cuts in pGEM4z-blue) of pPRc128 with the AatII-FspI$^{9,016}$ fragment of pPRc90, resulting in pPRc130. Finally, the PstI$^{8,675}$-ApaI$^{10,387}$ fragment of pPRc127 was replaced with the corresponding fragment of pPRC130, resultng in plasmid pPRc132. All subcloning steps in which single mutations were changed were verified by sequencing.

Full-length clone pPRKflc-133 was constructed by inserting the NcoI$^{5,532}$-XbaI$^{mcs}$ fragment of pPRc132 into NcoI$^{5,532}$XbaI$^{mcs}$ digested pPRc129.

Construction of a Hybrid Full-length Clone pPRKflc-h6.

Antigenically different but viable C-strain mutants can be made from pPRKflc-133, by exchanging part of the E1 gene of this construct with that of CSFV strain Brescia. To this end, the NheI$^{2,443}$-AflIII$^{2,999}$ fragment of pPRc129 was replaced with the corresponding fragment of pPEh6 (van Rijn et al., 1992), resulting in the 5' half hybrid clone pPRc139. Hybrid full-length clone pPRKflc-h6 was constructed by inserting the NcoI$^{5,532}$-XbaI$^{mcs}$ fragment of pPRc132 into pPRc139. This clone now contained the antigenic region of E1 of CSFV-strain Brescia including a unique BglII site.

All modification and cloning procedures used in Example 2 were carried out essentially as described (Sambrook et al. 1989. Molecular cloning: a laboratory manual. Cold Spring Harbor Laboratory, Cold Spring Harbor, N.Y.). Restriction enzymes and DNA modifying enzymes were commercially purchased and used as described by the suppliers. Plasmids were transformed and maintained in *Escherichia coli* strain DH5α (Hanahan. 1985. in DNA cloning 1: 109–135).

In vitro RNA Transcription

Plasmid DNA used for in vitro RNA transcription was purified using Qiagen columns (Westburg), according to manufacturers conditions. After linearisation with XbaI or SrfI, plasmid DNA was extracted with phenol and chloroform, precipitated with ethanol, vacuum dried and dissolved in an appropriate volume of RNase-free water.

One µg of linearised plasmid DNA was used as template for in vitro transcription. RNA was synthesised at 37° C. for 1 hr in 100 µl reaction mixtures containing 40 mM Tris-HCl pH 7.5, 6 mM MgCl$_2$, 2 mM Spermidine, 10 mM DTT, 100 U rRNasin (Promega), 0.5 mM each of ATP, GTP, CTP, UTP and 170 Units of T7 RNA polymerase (Pharmacia). Template DNA was removed by digestion with RNase-free DNaseI (Pharmacia) for 15 min. at 37° C., followed by extraction with phenol and chloroform, and ethanol precipitation. The RNA was dissolved in 20 µl RNase-free H$_2$O, and quantitated by UV measurement at 260 nm.

RNA Transfection

The RNA transfection mix was composed by gently mixing 50 µl of a lipofectine (Gibco BRL) dilution (10 µg lipofectine in RNase-free H$_2$O) and 50 µl of an RNA solution (1 µg RNA in RNase-free H$_2$O), and incubation of this mix at room temperature for 15 minutes. Subconfluent monolayers of SK6-cells in φ35 mm, 6-well tissue culture plates (Greiner) were used for RNA transfection. The cells were washed twice with Dulbecco's modified Eagles medium (DMEM). Then 1 ml of DMEM was added to the cells, followed by the RNA transfection mix. After incubation for 16 hrs at 37° C., the medium was replaced by 2 ml DMEM supplemented with 5% FBS. Incubation was continued for another 3 days at 37° C. Then cells were immunostained with CSFV specific monoclonal antibodies (Mabs) by the immunoperoxidase monolayer assay (IPMA) as described by Wensvoort et al. (Vet. Microbiol. 1986. 12: 101–108).

Characterisation of Recombinant C-strain Viruses.

The supernatants of transfected cells were brought on confluent monolayers of SK6-cells in wells of φ35 mm, and incubated for 5 days at 37° C. Cells of the transfected monolayers were trypsinised and diluted 7.5 times with DMEM and grown for another 7 days at 37° C. in 75 cm² flasks (Costar). Hereafter, virus stocks were prepared by freeze-thawing the cells twice, clarifying cell suspensions by centrifugation at 5,000×g for 10 min. at 4° C., and harvesting of the supernatants.

Virus was characterised by IPMA, and by restriction analysis of RT-PCR amplified viral fragments. After infection of SK6-cells with viruses FLc-h6 and Flc-133, monolayers were incubated for 4 days at 37° C. Subsequently, monolayers were immunostained using Mabs directed against conserved (Mab b3, domain A) and non-conserved (Mabs b5 and b6, domains B+C) epitopes on E1 of Brescia, and with Mabs specific for the C-strain and directed against E1 (Mab c2) or E2 (Mab c5) (Wensvoort, G. 1989. In Thesis, pp 99–113, Utrecht, The Netherlands). Monolayers of SK6-cells infected with native Brescia virus or native C-strain virus were controls in this assay. The results are presented in Table 1, and are as expected. Briefly, Mab b3 recognizes an epitope on E1 conserved among CSFV strains, and therefore recognizes all strains in Table 1. Mabs b5 and b6 do not recognize E1 of the C-strain and thus only react with strains Brescia and Flc-h6. In contrast, Mabc2 does not recognize E1 of strain Brescia. and thus only reacts with strains C and FLc-133. Finally, Mab c5 does not recognize E2 of strain Brescia, and therefore reacts with all viruses in Table 1 except strain Brescia.

The genomic RNA of virus FLc-h6 should contain a unique BglII site, which is located in the E1 gene (see above). To check for the presence of this site, cytoplasmic RNA was isolated from SK6-cells infected with recombinant virus FLc-h6, or infected with FLc-133, PCR-amplified as described above, using primers described by Van Rijn et al, 1993. J. Gen. Virol. 74:2053–2060), and digested with BglII. Indeed, the amplified fragment of 1,091 basepairs of FLc-h6 was cut by BglII, resulting in fragments of 590 and 501 basepairs, whereas the amplified fragment of FLc-133 remained intact.

EXAMPLE 3

Immunisation of Pigs with Deletion Mutants of E1

Construction and Expression of Deletion Mutants of E1 of CSFV Strain Brescia.

It was previously shown that TMR-less E1 of CSFV strain Brescia, expressed by insect cells, induces a protective immune response in pigs against CSF (Huist et al., 1993. J. Virol. 67: 5435–5442). Two distinct antigenic units, A and B+C, in the N-terminal half of E1, which induce neutralizing antibodies against CSFV, were also defined (Wensvoort. 1989. J. Gen. Virol. 70:2865–2876; Van Rijn et al. 1992. Vet. Microbiol. 33: 221–230; Van Rijn et al. 1993. J. Gen. Virol. 74: 2053–2060). Moreover, neutralizing antibodies directed against domain A and domains B+C act synergistically in neutralizing CSFV (Wensvoort. 1989. J. Gen. Virol. 70: 2865–2876). To evaluate the immunogenicity of mutant E1s with a deletion of domains B+C or with a deletion of domain A, relevant constructs in a baculovirus vector were made, and expressed mutant proteins were tested in pigs.

Baculoviruses expressing mutant E1s were constructed via overlap recombination of wild type AcNPV (*Autographa californica* nuclear polyhedrosis virus) DNA and DNA of transfer vector pAcMo8 containing the sequence encoding a particular mutant E1. Transfer vector pAcMo8 was derived from pAcAs3 (Vlak et al., 1990. Virology 179: 312–320) by inserting a T directly 5' of the first base (G) of the unique BamH1 site of the latter vector. In this way an ATG start codon was generated overlapping the first G of the BamHI site. Messenger RNA is transcribed from heterologous sequences inserted into the BamHI site by the AcNPV p10 promoter.

The sequences encoding mutant E1s were derived from the E1 insert of pPRb2 (Van Rijn et al., 1992. Vet. Microbiol. 33: 221–230) via PCR amplification. To this end two primers were constructed which contained a BamHI site in their sequence. The 5' end (+ sense) primer has the sequence 5'-AGA TTG GAT CCT AAA GTA TTA AGAGGA CAG GT-3' (SEQ ID No. 10). The underlined sequence in this primer is identical to nucleotides 2362–2381 in the sequence of strain Brescia (Moormann et al., 1990. Virology 177: 184–198), bold letters indicate the BamHI site. The 3' end (− sense) primer contains a stop-codon adjacent to the BamH1 site. It has the sequence 5'-TA GTC GGA TCC TTA GAA TTC TGC GAA GTA ATC TGA-3' (SEQ ID No. 11). The underlined sequence in this primer is complementary to nucleotides 3433–3453 in the sequence of strain Brescia (Moormann et al., 1990. Virology 177: 184–198); bold letters indicate the BamHI site, and letters in italics indicate the stop-codon.

Amplified sequences were cloned into the BamHI site of pAcMo8 and checked for a correct orientation in the vector by restriction enzyme analysis. The correct transfer vector was designated pPAb11. Overlap recombination between AcNPV DNA and DNA of pPAb11, and selection and purification of a baculovirus vector expressing E1 was performed as described (Hulst et al., 1993. J. Virol. 67: 5435–5442). Further characterisation of E1 in radioimmunoprecipitation assays, and with E1 specific Mabs was also described by Hulst et al. (J. Virol., 1993. 67: 5435–5442). The resulting recombinant baculovirus expresses wild-type Brescia E1 without a TMR (compare $2^{nd}$ bar from top in FIG. 3). This TMR-less E1 is secreted from the cells (Hulst et al., 1993. J. Virol. 67: 5435–5442).

Deletion of the region encoding domains B+C from the E1 gene of pPAb11 was achieved by exchanging the NheI-BglII fragment of this construct with the corresponding fragment of pPEh14 (Van Rijn et al., 1993. J. Gen. Virol. 74: 2053–2060). The resulting transfer vector was designated pPAb16. It contains a deletion in the E1 gene running from codon 693 to 746. Similarly, the region encoding domain A was deleted from pPAb11 by exchanging the NheI-BglII fragment of pPAb11 with the corresponding fragment of pPEh18 (Van Rijn et al., 1993. J. Gen. Virol. 74: 2053–2060), resulting in transfer vector pPAb12. pPAb12 contains a deletion in the E1 gene running from codon 800 to 864.

Recombinant baculoviruses expressing the deleted E1s were constructed, selected, and characterised with regard to their E1 expression products, as described above.

Immunisation and Challenge Exposure of Pigs.

Groups of four (or two) specific-pathogen-free (SPF), 6 to 8 week old pigs were vaccinated intramuscularly on day 0 with 1 ml of a double water-oil emulsion containing 4 μg (mutant) E1, and revaccinated on day 28 with 1 ml of a double water-oil emulsion containing 15 μg (mutant) E1 (Table 2). The construction of mutant E1 containing a deletion in domain A, or a deletion in domain B/C, and of wild type E1 is described above and specified by the constructs depicted in FIG. 5. For the first vaccination on day 0, supernatant of insect cells infected with the appropriate recombinant baculoviruses was used. The amount of E1 in the supernatant was calibrated as described before (Hulst et al., 1993. J. Virol. 67: 5435–5442). For revaccination on day 28, E1 was immunoaffinity-purified from the supernatant of the infected insect cells (Hulst et al., 1993. ibid). Pigs of all vaccinated groups, and an unvaccinated control group of two SPF animals, were challenged intranasally with 100 $LD_{50}$ of CSFV strain Brescia 456610 (Terpstra and Wensvoort. 1988. Vet. Microbiol. 16: 123–128). This challenge dose leads to acute disease in unprotected pigs characterised by high fever and thrombocytopenia starting at days 3 to 5 and to death at days 7 to 11. Heparinised (EDTA) blood samples were taken on days 40, 42, 45, 47, 49, 51, 53, and 56 after vaccination, and analysed for thrombocytes and CSFV virus as described (Hulst et al., 1993. ibid). Serum blood samples were taken on days 0, 21, 28, 42, and 56 and tested in the CTB-ELISA (Wensvoort et al., 1988. Vet. Microbiol. 17: 129–140) and in the neutralizing peroxidase-linked assay (NPLA, Terpstra et al. 1984. Vet. Microbiol. 9: 113–120), to detect (neutralizing) antibodies against CSFV. Test results in the CTB-ELISA are expressed as the percentage inhibition of a standard signal; <30% inhibition is negative, 30–50% inhibition is doubtful, >50% inhibition is positive. NPLA titers are expressed as the reciprocal of the serum dilution that neutralised 100 $TCID_{50}$ of strain Brescia in 50% of the replicate cultures.

All animals were observed daily for signs of disease, and body temperatures were measured. Clinical signs of disease were: Fever, anorexia, leukopenia, thrombocytopenia, and paralysis.

EXAMPLE 4

Development of a CTB-ELISA (CTB-DIF) for CSFV, Based on One Monoclonal Antibody

Description of the Diagnostic Test.

This example describes a CTB-ELISA (CTB-DIF), which is a modification of the existing CTB-ELISA (Wensvoort et al., 1988. Vet. Microbiol. 17: 129–140) for the detection of CSFV specific antibodies.

The CTB-DIF is based on the finding that SF21 cells infected with a recombinant baculovirus expressing E1-TMR, efficiently secrete dimerised E1 into the medium. This dimerised secreted E1 was detected when media of cells infected with the above baculovirus was analysed on western blot after electrophoresis in SDS-PAGE under non-reduced conditions. For E1 specific Mabs, two copies of an epitope are present on dimers of E1 (one on each monomer). Thus, in conjunction with the dimerised antigen a particular E1 specific Mab can be used as capture antibody, coated to the wall of a microtiter plate well, as well as detecting, horseradish peroxidase (HRPO) conjugated antibody.

The CTB-DIF is shown to be useful in conjunction with an E1 subunit vaccine which has a deletion in domain A (see FIG. 5 for construct) and is shown to distinguish between CSFV specific antibodies induced in pigs vaccinated with E1 with a deleted domain A. and CSFV specific antibodies induced in pigs infected with low-virulent CSFV strains Henken, Zoelen, Bergen, 331, and Cedipest (EP-A-351901).

Four SPF pigs, numbered 766, 786, 789, and 770, were vaccinated with mutant E1 containing a deletion in domain A. as described in example 3 (see also Table 2), and challenged with virulent CSFV strain Brescia on day 44 after vaccination. Sera taken on days 28, 42, and 56 after vaccination, were tested.

Sera against the low-virulent CSFV strains were also prepared in groups of four SPF pigs. Sera from pigs infected with strains Henken, Zoelen, Bergen, and 331 were tested at days 0, 21, 28 and 42 after infection. Sera from pigs vaccinated with the Cedipest vaccine were tested at days 0, 44, 72, and 170 after vaccination.

Three different serological tests were performed with the above sera. Test 1 is the neutralizing peroxidase-linked assay (NPLA) described by Terpstra et al. 1984. (Vet. Microbiol. 9: 113–120), to detect neutralizing antibodies against CSFV. Test 2 is the CTB-ELISA (Wensvoort et al., 1988. Vet. Microbiol. 17: 129–140), to routinely detect antibodies against CSFV.

The CTB-DIF uses Mab b3 (also known as CVI-HCV-39.5) (Wensvoort. 1989. J. Gen. Virol. 70:2865–2876.), which recognizes an epitope located in domain A1 of E1 of CSFV. The wells of an ELISA plate are coated with Mab b3 (dilution 1:2.000) (capture antibody). After the wells are washed, Mab b3, conjugated to (HRPO), (dilution 1:4.000) (detecting antibody), is added to the wells. Media of Sf21 cells infected with a baculovirus producing E1-TMR and containing dimerised E1 to a concentration of 20 μg/ml is diluted 1:500, and pre-incubated with the test serum (diluted 1:2.5). The serum-antigen mixture is then added to the conjugate in the wells of the coated ELISA plate. After incubation, the wells are washed again and the chromogen-substrate solution is added. If both the capture and conjugated Mab have bound to the antigen, the HRPO induces a chromogenic reaction, indicating that the test serum is negative for CSFV antibodies. If the epitope on the antigen is blocked by antibodies from the test serum, the HRPO-conjugate will be washed away and the wells will remain clear, indicating the test serum contains antibodies against CSFV, domain A1. The results with the three different serological tests are indicated in Table 3.

Sera of pigs vaccinated with E1 with a deletion in domain A1. do react in the NPLA and CTB-ELISA, and not in the CTB-DIF, on day 42 after vaccination. After challenge with virulent CSFV strain Brescia sera of the same pigs react positively in all the 3 tests on day 56 after vaccination (day 12 after challenge), indicating that a booster response has taken place after challenge. Starting on day 21 after infection, sera from pigs vaccinated with strains Henken, Zoelen, Bergen, and 331 react positively in the NPLA, the CTB-ELISA, and the CTB-DIF. Starting on day 44 after vaccination, the same holds true for pigs vaccinated with the Cedipest vaccine strain.

Thus, the CTB-DIF exactly performs as desired, and is suited to accompany a CSFV marker vaccine with a mutated domain A of E1, such that antibodies directed against this mutated domain A do not compete with Mab b3 for the epitope of Mab b3.

The antigen used in the CTB-DIF is the dimerised TMR-less wild type Brescia E1 depicted in FIG. 5. However, dimerised E1 synthesised by the "deletion domains B+C" construct of FIG. 5 is also suitable as an antigen in the test.

EXAMPLE 5

Comparison of CTB-ELISA's for CSFV Based on E1 and E2

Description of the Diagnostic Tests

This example describes a modification of the CTB-DIF of example 4, and a CTB-ELISA based on E2 of CSFV, and compares the sensitivity of these ELISAs with 3 other CTB-ELISAs detecting antibodies directed against E1 and the NPLA (Terpstra et al. 1984. Vet. Microbiol. 9: 113–120).

The CTB-DIF of example 4, called E1-Bac-DIF in Tables 4 to 8, uses intact TMR-less E1 synthesized in insect cells (SF21 cells) as an antigen. The modification of E1-Bac-DIF, called E1-Bac-dBC-DIF, uses TMR-less E1 synthesized in insect cells (SF 21 cells) with a deleted domain B+C (compare FIG. 5) as an antigen. As established on western blot, TMR-less E1 with deleted domains B+C is secreted from the cell as a dimer (results not shown). Test E1-bac-dBC-DIF is performed as follows. The wells of an ELISA plate are coated with Mab b3 (dilution 1:4,000) (capture antibody), 16 h at 37° C., and washed. Medium containing dimerised antigen E1-dBC to a concentration of 20 µg/ml is diluted 1:50, and pre-incubated with the test serum (dilution 1–2.5) (0.5 h at 37° C.). The serum-antigen mixture is then added to the coated ELISA plate. After incubation, 1 h at 37° C., the wells are washed and Mab b3, conjugated to HRPO (dilution 1:1,000) (detection antibody), is added. After incubation, 1 h at 37° C., the wells are washed again and the chromogen-substrate solution is added. The chromogenic reaction is performed for 10 minutes at room temperature. The interpretation of the chromogenic reaction is the same as explained in example 4.

Other CTB-ELISAs detecting antibodies directed against E1 of CSFV described in Tables 4 to 8 are the E1-CSFV ELISA. using native E1 from CSFV infected cells as antigen (Wensvoort et al., 1988. Vet. Microbiol. 17:129–140); the E1-Bac and E1-Bac-DIF ELISAs, use TMR-less E1 synthesized in insect cells as antigen. The E1-CSFV and E1-Bac ELISAs use CSFV Mabs b3 and b8 (Wensvoort 1989. J. Gen. Virol. 70: 2,865–2,876) as capture and detection antibody, respectively, whereas the E1-Bac-DIF ELISA uses only Mab b3 as both capture and detection antibody. The E1-CSFV ELISA is performed exactly as described by Wensvoort et al., 1988. (Vet. Microbiol. 17:129–140). The E1-Bac, and E1-Bac-DIF ELISAs are performed as described above for the E1-Bac-dBC-DIF with the following modifications. In the E1-Bac ELISA the antigen used is a 1:400 dilution of dimerized E1 present in the medium of SF21 cells, infected with the relevant E1 baculovirus construct (compare FIG. 5), at a concentration of 20 µg/ml. Mab b8 which is conjugated to HRPO is the detection antibody in this ELISA, and is used at a dilution of 1:1000. The E1-Bac-DIF ELISA uses the same antigen as the E1-Bac ELISA but at a dilution of 1:200. HRPO conjugated Mab b3 is used as detection antibody in this ELISA at a dilution of 1:1,000.

The E2-Bac ELISA uses CSFV E2 antigen synthesized in SF21 cells infected with the Bac CE2 construct (Hulst et al., 1994. Virology 200: 558–565). Because E2 is not secreted from the infected insect cells, the lysate of these cells is used. Like E1, most of E2 is found as dimerized molecules when lysates of infected cells are analyzed under non-denaturing conditions in SDS-PAGE gels (results not shown). The CTB-ELISA developed on the basis of this E2 antigen performs optimally in conjunction with Mabs C5 and C12 (Wensvoort, G. 1989. In Thesis, pp99–113, Utrecht). However, also E2 in conjunction with only Mab C5 or Mab C12 may be used. In a competition assay Mabs C5 and C12 inhibit each other with regard to binding to E2. This indicates that these Mabs recognize the same, or overlapping epitopes on E2 (results not shown). The E2-Bac ELISA is performed as follows. Mab C12 is diluted 1:1,000, and coated to the wells of an ELISA plate (16 h at 37° C.). Hereafter, wells are washed. Lysates of SF21 cells infected with Bac CE2, diluted 1:1,250, are preincubated with the test serum (1:1) for 0.5 h at 37° C. The serum-antigen mixture is then added to the wells of the coated plates and incubated for 1 h at 37° C. Subsequently plates are washed and incubated with Mab C5 conjugated to HRPO (dilution 1:2,000). After 1 h at 37° C. plates are washed again and the chromogen-substrate solution is added. The chromogenic reaction is performed for 10 minutes at room temperature. The interpretation of the chromogenic reaction is the same as explained in example 4. All above described dilutions are performed in NPLA buffer+4% PS (Terpstra et al., Vet. Microbiol. 9: 113–120).

Table 4 shows the results of the analysis of sera of 3 SPF pigs vaccinated with the Cedipest vaccine with the above described CTB-ELISAs and the NPLA. Sera were analyzed at days 0, 16, 23, 30, 37, 44, 50, 72, 113, 141, and 170 after vaccination. Tables 5 to 8 show the results of the analysis with the above described CTB-ELISAs and the NPLA of sera of groups of 5 SPF pigs infected with the low-virulent CSFV strains 331, Bergen, Henken, and Zoelen, respectively. Sera were analyzed at days 0, 10, 14, 17, 24, 28, 35, and 42 after infection. Starting at day 16 after vaccination, sera from pigs vaccinated with the Cedipest strain react in each of the 5 CTB-ELISAs as well as in the NPLA. At this time point the sensitivity of the E2-Bac ELISA and the E1-Bac-dBC-DIF is as good, if not better, than that of the other 3 CTB-ELISAs. From day 37 after vaccination up till day 170, all sera react consistently (positive) in the 5 CTB-ELISAs as well as the NPLA. Sera of pigs infected with the low-virulent CSFV strains also react in all 5 CTB-ELISAs as well as in the NPLA. With an occasional exception consistency in the reaction of the sera in the 5 CTB-ELISAs and the NPLA is observed from day 21 after infection up till day 42. More sera of animals infected with low virulent strains need to be analyzed to be able to conclude whether there are significant differences between the sensitivity of the 5 CTB-ELISAs early after infection (up till day 17).

It can be concluded that the E2-Bac ELISA and the E1-Bac-CTB-DIF ELISA both perform as desired. Therefore the E2-Bac ELISA is suitable to accompany a CSFV marker vaccine (eg. subunit E1, whether mutated or not, a C-strain marker vaccine modified in the E2 region) which does not induce antibodies that compete with the Mabs in this ELISA. The E1-Bac-dBC-DIF ELISA is as suitable as the E1-Bac-DIF ELISA (CTB-DIF ELISA of example 4) to accompany a CSFV marker vaccine with a mutated domain A of E1, such that antibodies directed against this mutated domain A do not compete with Mab b3 for the epitope of Mab b3.

Description of the Figures

FIG. 1.

Schematic representation of the cDNA clones used to determine the nucleotide sequence of the C-strain. FIG. 1A indicates the first round cDNA clones (see text). cDNA clones with numbers 32, 90, and 96 were used to change pPRKflc-113 into pPRKflc-133 (see example 2). Clone 14 was the only first round cDNA clone used for construction of pPRKflc-113 (see FIG. 3). FIG. 1B indicates second round cDNA clones (see text). The numbered second round cDNA clones were used to construct pPRKflc-1 13 (see SEQ ID No. 1). Positions of the cDNA with respect to the nucleotide sequence of the genome of the C-strain are indicated by the scale bar (in kilobases) at the bottom of the figure. A schematic representation of the currently identified genes of CSFV, and their organisation in the CSFV genome is indicated at the top of the figure.

There is no consensus yet among workers in the field about the nomenclature of pestivirus proteins. The E2 protein as described here is also called gp42 (Tamura et al. 1993. Virology 193: 1–10), gp44/48 (Thiel et al. 1991. J. Virol. 65: 4705–4712) or E0 (Rümenapf et al. 1993. J. Virol. 67: 3288–3294). The E3 protein is also called gp25 (Tamura et al. 1993. Virology 193: 1–10), gp33 (Thiel et al. 1991. J. Virol. 65: 4705–4712) or E1 (Rümenapf et al. 1993. J. Virol. 67: 3288–3294). The E1 protein of this invention is also called gp53 (Tamura et al. 1993. Virology 193: 1–10), gp55 (Thiel et al. 1991. J. Virol. 65:4705–4712), gp51–54 (Moormann et al. 1990. Virology 177:184–198) and E2 (R ümenapf et al. 1993. J. Virol. 67: 3288–3294). The N-terminal autoprotease $N^{pro}$ of CSFV (p20 of BVDV, Wiskerchen et al. 1991. J. Virol. 64: 4508–4514), also called p23, was identified by Thiel et al. 1991. (J. virol. 65: 4705–4712). Cleavage of the recognition sequence, which is conserved among pestiviruses, of this protease results in the N-terminus of C (Stark et al. 1993. J. Virol. 67: 7088–7095).

FIGS. 2A–2B.

Alignment of the nucleotide sequences of the 5' (A) and 3' (B) non-coding regions of CSFV strains Brescia, Alfort, and C. Except for the first 12 nucleotides, the 5' non-coding sequence of strain Brescia has been described by Moormann et al., 1990. Virology 177: 184–198. The first 12 nucleotides of the 5' non-coding region of strain Brescia have not been published before. Like the ultimate 5' and 3' sequences of the genome of the C-strain, they were determined with the 3'–5' RNA ligation method described in Example 1 of this patent application. Except for the first 9 nucleotides, the 5' non-coding sequence of strain Alfort has been described by Meyers et al., 1989. Virology 171: 555–567. The first 9 nucleotides of the genome of strain Alfort were published by Meyers in a Thesis entitled: "Virus der Klassischen Schweinepest: Genomanalyse und Vergleich mit dem Virus der Bovinen Viralen Diarrhoe". 1990. Tübingen, Germany. The sequences of the 3' non-coding regions of strains Brescia and Alfort have been described by Moormann et al., 1990. Virology 177: 184–198 and Meyers et al., 1989. Virology 171: 555–567, respectively. The ATG start codon and the TGA stopcodon of the large ORF (compare SEQ ID No. 1), are underlined.

FIG. 3.

Construction scheme of full-length cDNA clone pPRKflc-113. Clone numbers have been explained in the legend of FIG. 1. Fusion sites of inserts of clones are indicated by vertical lines. The sites corresponding with these lines are indicated at the bottom of the figure. Underlined clone numbers indicate cDNA clones having pOK12 (Vieira and Messing. 1991. Gene 100: 189–194) derived vector sequences (see FIG. 4). The 5' and 3' ends of pPRKflc-113 were tailor made via PCR amplification of cDNA fragments (see text Example 2). The amplified fragments are indicated with PCR. The scale bar at the bottom of the figure, and the schematic representation of the genome organisation of CSFV, have been described in the legend of FIG. 1.

FIG. 4.

Schematic representation of the vector sequences and full-length cDNA inserts in clones pPRKflc-113, pPRKflc-133, and pPRKflc-h6. The construction of vector pPRK, a derivative of pOK12 (Vieira and Messing. 1991. Gene 100: 189–194), has been described in Example 2. $Kan^R$, kanamycin resistance gene; ORI, origin of replication: 'i, gene encoding repressor of β-galactosidase gene; PO, promoter/operator region of β-galactosidase gene; lacZ, part of the β-galactosidase gene encoding the subunit of β-galactosidase. Several restriction sites of the vector, and the sequences directly flanking the full-length inserts in the vector, are indicated. Relevant sites have been described in the text of Example 2. The lollypops and numbers in pPRKflc-113 correspond to the nucleotides of the five codons which were changed in this construct, resulting in pPRKflc-133. The latter construct has the sequence as indicated in SEQ ID No. 1.

The black box in pPRKflc-h6 indicates the region of E1 of pPRKflc-133 that was exchanged with the corresponding region of strain Brescia. Whether transcripts derived from a particular full-length construct are infectious (+) or not (−) is indicated to the right of the construct. T7, T7 promoter sequence. Inserts of full-length constructs are indicated in relation to a scale bar (in kilobases) representing the nucleotide sequence of the C-strain as indicated in SEQ ID No. 1.

FIG. 5.

Schematic representation of mutant E1 proteins expressed in insect cells with a baculovirus vector. All E1 proteins are encoded by the nucleotide sequence of strain Brescia (Moormann et al., 1990. Virology 177: 184–198), and start at their N-terminus with the Lys at codon position 668 in the large ORF of this sequence. The C-terminus of native E1 is the Leu at codon position 1,063 in the large ORF, whereas the C-termini of the three other E1 proteins are located at amino acid position 1,031. The dotted boxes in the bars represent the N-terrninal signal sequence, running from amino acid residues 668 to 689, the internal hydrophobic sequence, running from amino acid residues 806 to 826, and the C-terminal transmembrane region (TMR), located in the region running from amino acid residues 1,032 to 1,063, of E1. The deleted amino acid sequences in mutant E1s with a deleted B+C or A domain are indicated by interruptions in the bars representing these proteins. The location of these deletions in relation to the amino acid sequence of E1 can be determined from the scale bar at the bottom of the figure. The scale bar indicates the location of E1 in the amino acid sequence encoded by the large ORF of strain Brescia.

TABLE 1

Characterisation of recombinant C-strain viruses
Mabs specific for CSFV

| | directed against E1 | | | directed against E2 |
|---|---|---|---|---|
| virus | conserved epitopes | Brescia specific epitopes | "C" specific epitopes | "C" specific epitopes |
| "C" | + | − | + | + |
| Brescia | + | + | − | − |
| FLc-133 | + | − | + | + |
| FLc-h6 | + | + | − | + |

TABLE 2

Vaccination of pigs with deletion mutants of E1

| Pig no. | Construct used | % Inhibition in the CTB-ELISA on days: | | | | | Neutralizing antibody titer on days: | | | | | Results of CSFV challenge: | | |
|---|---|---|---|---|---|---|---|---|---|---|---|---|---|---|
| | | 0 | 21 | 28 | 42 | 56 | 0 | 21 | 28 | 42 | 56 | Disease | Viremia | Death |
| 766 | Deletion | 0 | 12 | 0 | 78 | 99 | <12.5 | <25 | <25 | 3,200 | >3,200 | ----- | − | − |
| 768 | Domain | 0 | 0 | 0 | 74 | 99 | <12.5 | <25 | <25 | 2,400 | >3,200 | ----- | − | − |
| 769 | A | 0 | 16 | 0 | 99 | 99 | <12.5 | <25 | <25 | 2,400 | >3,200 | ----- | − | − |
| 770 | | 0 | 14 | 0 | 83 | 99 | <12.5 | <25 | <25 | 400 | >3,200 | ----- | − | − |
| 771 | Deletion | 0 | 36 | 25 | 100 | 99 | <12.5 | <25 | <25 | 300 | >3,200 | ----- | − | − |
| 772 | Domain | 0 | 25 | 29 | 100 | 99 | <12.5 | <25 | <25 | 1,200 | >3,200 | ----- | − | − |
| 773 | B + C | 0 | 7 | 0 | 100 | 99 | <12.5 | <25 | <25 | 200 | 150 | ----- | − | − |
| 774 | | 0 | 49 | 52 | 99 | 99 | <12.5 | <25 | <25 | 300 | >3,200 | ----- | − | − |
| 792 | Wild type | 0 | 35 | 31 | 98 | 100 | <12.5 | 2,000 | 1,200 | >3,200 | >3,200 | +---- | − | − |
| 794 | BresciaE1 | 0 | 48 | 40 | 98 | 100 | <12.5 | <25 | <25 | 1,600 | >3,200 | +---- | − | − |
| 775 | None | 0 | 2 | 0 | 0 | | <12.5 | <25 | <25 | <25 | | +++++ | + | + |
| 795 | | 0 | 0 | 0 | 0 | | <12.5 | <25 | <25 | <25 | | +++++ | + | + |

Groups of four (or two) SPF pigs were inoculated intramuscularly on day 0 with 4 μg and on day 28 with 15 μg modified E1 protein. On day 42, the pigs were challenged intranasally with 100 LD50 of CSF strain Brescia 456610. All animals were observed daily for signs of disease. Blood samples were taken at days 0, 21, 28, 42, and 56 and tested in the CTB-ELISA and the neutralisation test for the detection of antibodies against CSFV(Terpstra et al., 1984. Vet. Microbiol. 9: 113–120). Clinical signs of disease were: Fever, anorexia, leukopenia, thrombocytopenia, and paralysis and the presence or absence of these signs is indicated in that order by a + or − in the table listed under disease.

TABLE 3

Differential diagnostic ELISA test for CSFV

| Serum | DPV or DPI[a] | NPLA[b] | CTB-ELISA[c] | CTB-DIF[c] |
|---|---|---|---|---|
| 766 | 28 | <25 | 9 | 27 |
| 768 | 28 | <25 | 0 | 27 |
| 769 | 28 | <25 | 17 | 0 |
| 770 | 28 | <25 | 11 | 0 |
| 766 | 42 | 3200 | 81 | 0 |
| 768 | 42 | 2400 | 52 | 0 |
| 769 | 42 | 2400 | 99 | 26 |
| 770 | 42 | 400 | 65 | 0 |
| 766 | 56 | >3200 | 99 | 65 |
| 768 | 56 | >3200 | 100 | 104 |
| 769 | 56 | >3200 | 101 | 105 |
| 770 | 56 | >3200 | 101 | 104 |
| Henken | 0 | <12.5 | 5 | 18 |
| Henken | 21 | 50 | 76 | 47 |
| Henken | 28 | 75 | 92 | 88 |
| Henken | 42 | 300 | 100 | 102 |
| Zoelen | 0 | <12.5 | 0 | 0 |
| Zoelen | 17 | 37.5 | 85 | 71 |
| Zoelen | 21 | 150 | 90 | 80 |
| Zoelen | 42 | 400 | 100 | 108 |
| Bergen | 0 | <12.5 | 1 | 49 |
| Bergen | 21 | 25 | 96 | 100 |
| Bergen | 28 | 100 | 99 | 95 |
| Bergen | 42 | 300 | 100 | 103 |
| 331 | 0 | 18.75 | 4 | 15 |
| 331 | 21 | 100 | 92 | 90 |
| 331 | 28 | 300 | 99 | 99 |
| 331 | 42 | 300 | 100 | 105 |
| Cedipest | 0 | <12.5 | 0 | 19 |
| Cedipest | 44 | 75 | 85 | 93 |
| Cedipest | 72 | 50 | 89 | 102 |
| Cedipest | 170 | 150 | 98 | 106 |

[a]DPV: days post vaccination; DPI: days post infection
[b]NPLA titers are expressed as the reciprocal of the serum dilution neutralizing 100 TCID$_{50}$ of HCV strain Brescia in 50% of the replicate cultures (Terpstra et al. 1984. Vet Microbiol. 9: 113–120).
[c]Complex trapping blocking-ELISA, CTB-ELISA, or differential CTB-ELISA, CTB-DIF. Test results are expressed as the percentage inhibition of a standard signal; <30% inhibition is negative, 30–50% inhibition is doubtful, >50% inhibition is positive.

TABLE 4

Comparison of CTB-ELISA's with CSFV strain Cedipest sera

| strain | pig | DPV[a] or DPI | NPLA[b] | CTB-ELISA[c] | | | | |
|---|---|---|---|---|---|---|---|---|
| | | | | E1 CSFV | E1-Bac | E1-Bac DIF | E1-Bac dBC-DIF | E2-Bac |
| Cedi- | 1 | 0 | <12.5 | 21 | ND | ND | ND | 0 |
| pest | 2 | 0 | <12.5 | 28 | 8 | 0 | 0 | 0 |
| | 3 | 0 | <12.5 | 25 | 0 | 0 | 0 | 0 |
| | 1 | 16 | 25 | 60 | 0 | 56 | 62 | 79 |
| | 2 | 16 | 25 | 66 | 51 | 26 | 76 | 79 |
| | 3 | 16 | 19 | 11 | 15 | 0 | 11 | 62 |
| | 1 | 23 | 25 | 54 | 66 | 60 | 68 | 79 |
| | 2 | 23 | 50 | 81 | 57 | 54 | 75 | 74 |
| | 3 | 23 | 25 | 25 | 37 | 32 | 54 | 74 |
| | 1 | 30 | 50 | 76 | 87 | 80 | 81 | 75 |
| | 2 | 30 | 75 | 87 | ND | ND | ND | ND |
| | 3 | 30 | 19 | 60 | 40 | 28 | 57 | 82 |
| | 1 | 37 | 50 | 82 | 90 | 80 | 87 | 85 |
| | 2 | 37 | 50 | 87 | 84 | 61 | 85 | 85 |
| | 3 | 37 | 19 | 49 | 62 | 63 | 79 | 77 |
| | 1 | 44 | 75 | 84 | 94 | 99 | 92 | 88 |
| | 2 | 44 | 75 | 90 | 89 | 74 | 93 | 92 |
| | 3 | 44 | 25 | 66 | 68 | 79 | 93 | 90 |
| | 1 | 50 | 75 | 86 | 93 | 92 | 98 | 89 |
| | 2 | 50 | 150 | 91 | 95 | 96 | 97 | 91 |
| | 3 | 50 | 19 | 74 | 67 | 58 | 95 | 88 |
| | 1 | 72 | 50 | 86 | 92 | 94 | 99 | 81 |
| | 2 | 72 | 200 | 94 | 96 | 93 | 100 | 89 |
| | 3 | 72 | 25 | 53 | 76 | 66 | 99 | 73 |
| | 1 | 113 | 75 | 94 | 99 | 100 | 100 | 92 |
| | 2 | 113 | 200 | 94 | 98 | 100 | 99 | 89 |
| | 3 | 113 | 75 | 93 | 99 | 100 | 96 | 84 |
| | 1 | 141 | 75 | 91 | 100 | 91 | 100 | 89 |
| | 2 | 141 | 150 | 76 | 100 | 95 | 100 | 85 |
| | 3 | 141 | 50 | 87 | 94 | 95 | 100 | 85 |
| | 1 | 190 | 150 | 92 | 97 | 100 | 100 | 94 |
| | 2 | 170 | 150 | 85 | 97 | 100 | 100 | 86 |
| | 3 | 170 | 150 | 74 | 88 | 84 | 98 | 88 |

[a],[b]For explanation see Table 3 footnotes a and b, respectively.
[c]CTB-ELISA's E1CSFV, E1-Bac, E1-Bac-DIF, E1-Bac-dBC-DIF and E2-Bac are explained on Example 5. Test results are expressed as the percentage inhibition of a standard signal; <30% inhibition is negative, 30–50% inhibition is doubtful, >50% inhibition is positive.

TABLE 5

Comparison of CTB-ELISA's with CSFV strain 331 sera

| | | | | CTB-ELISA[c] | | | | |
|---|---|---|---|---|---|---|---|---|
| strain | pig | DPI[a] | NPLA[b] | E1 CSFV | E1-Bac | E1-Bac DIF | E1-Bac dBC-DIF | E2-Bac |
| 331 | 1 | 0 | <12.5 | 0 | 0 | 0 | 8 | 0 |
| | 2 | 0 | <12.5 | 4 | 5 | 0 | 0 | 0 |
| | 3 | 0 | <19 | 4 | 13 | 0 | 0 | 0 |
| | 4 | 0 | <12.5 | 0 | 14 | 0 | 0 | 0 |
| | 5 | 0 | <12.5 | 5 | 11 | 11 | 0 | 0 |
| | 1 | 10 | <12.5 | 0 | 13 | 0 | 14 | 13 |
| | 2 | 10 | <12.5 | 0 | 11 | 0 | 0 | 13 |
| | 3 | 10 | <12.5 | 0 | 20 | 16 | 24 | 31 |
| | 4 | 10 | <12.5 | 0 | 29 | 0 | 9 | 26 |
| | 5 | 10 | <12.5 | 0 | 24 | 7 | 38 | 18 |
| | 1 | 14 | <12.5 | 0 | 34 | 9 | 34 | 8 |
| | 2 | 14 | <12.5 | 2 | 18 | 0 | 0 | 36 |
| | 3 | 14 | 19 | 28 | 67 | 22 | 60 | 60 |
| | 4 | 14 | 19 | 35 | 77 | 37 | 60 | 10 |
| | 5 | 14 | 25 | 32 | 99 | 74 | 90 | 23 |
| | 1 | 17 | 19 | 7 | 84 | 53 | 69 | 0 |
| | 2 | 17 | <12.5 | 23 | 0 | 0 | 0 | 4 |
| | 3 | 17 | 25 | 63 | 93 | 62 | 87 | 54 |
| | 4 | 17 | 37 | 55 | 82 | 36 | 80 | 0 |
| | 5 | 17 | 37 | 69 | 100 | 84 | 94 | 3 |
| | 1 | 21 | 37 | 57 | 84 | 100 | 50 | 39 |
| | 2 | 21 | 37 | 29 | 52 | 0 | 26 | 3 |
| | 3 | 21 | 100 | 76 | 93 | 100 | 96 | 96 |
| | 4 | 21 | 50 | 76 | 90 | 100 | 91 | 63 |
| | 5 | 21 | 75 | 65 | ND | ND | ND | 72 |
| | 1 | 28 | 75 | 73 | 95 | 100 | 96 | 96 |
| | 2 | 28 | 25 | 59 | 89 | 100 | 79 | 58 |
| | 3 | 28 | 300 | 78 | 100 | 100 | 100 | 100 |
| | 4 | 28 | 150 | 74 | 93 | 100 | 80 | 82 |
| | 5 | 28 | 100 | 72 | 98 | 100 | 100 | 91 |
| | 1 | 35 | 75 | 83 | 95 | 100 | 97 | 98 |
| | 2 | 35 | 150 | 80 | 98 | 100 | 100 | 96 |
| | 3 | 35 | 300 | 80 | 99 | 100 | 100 | 100 |
| | 4 | 35 | 200 | 81 | ND | ND | ND | ND |
| | 5 | 35 | 150 | 82 | 98 | 100 | 100 | 90 |
| | 1 | 42 | 150 | 81 | 98 | 100 | 96 | 99 |
| | 2 | 42 | 200 | 80 | 100 | 94 | 100 | 98 |
| | 3 | 42 | 300 | 79 | 94 | 100 | 100 | 100 |
| | 4 | 42 | 200 | 79 | 97 | 100 | 99 | 100 |
| | 5 | 42 | 150 | 80 | 98 | 100 | 100 | 90 |

[a,b,c] See footnotes of Table 4.

TABLE 6

Comparison of CTB-ELISA's with CSFV strain Bergen sera

| | | | | CTB-ELISA[c] | | | | |
|---|---|---|---|---|---|---|---|---|
| strain | pig | DPI[a] | NPLA[b] | E1 CSFV | E1-Bac | E1-Bac DIF | E1-Bac dBC-DIF | E2-Bac |
| Bergen | 1 | 0 | <12.5 | 0 | 2 | 0 | 0 | 0 |
| | 2 | 0 | <12.5 | 0 | 0 | 0 | 0 | 0 |
| | 3 | 0 | <12.5 | 0 | 2 | 0 | 0 | 0 |
| | 4 | 0 | <12.5 | 0 | 7 | 0 | 0 | 0 |
| | 5 | 0 | <12.5 | 0 | 4 | 0 | 2 | 0 |
| | 1 | 10 | <12.5 | 0 | 0 | 6 | 0 | 27 |
| | 2 | 10 | <12.5 | 0 | 5 | 0 | 0 | 4 |
| | 3 | 10 | 12.5 | 0 | 25 | 0 | 27 | 21 |
| | 4 | 10 | <12.5 | 0 | 15 | 0 | 13 | 29 |
| | 5 | 10 | 12.5 | 0 | 14 | 0 | 6 | 21 |
| | 1 | 14 | <12.5 | 0 | 51 | 32 | 18 | 12 |
| | 2 | 14 | <12.5 | 8 | 12 | 9 | 10 | 4 |
| | 3 | 14 | 37 | 20 | 76 | 53 | 72 | 11 |
| | 4 | 14 | 12.5 | 0 | 55 | 8 | 77 | 18 |
| | 5 | 14 | <12.5 | 0 | 17 | 9 | 10 | 0 |
| | 1 | 17 | 25 | 57 | 93 | 84 | 73 | 3 |
| | 2 | 17 | <12.5 | 28 | 45 | 0 | 51 | 29 |
| | 3 | 17 | 75 | 75 | 100 | 78 | 90 | 0 |
| | 4 | 17 | 37 | 47 | 88 | 57 | 85 | 16 |
| | 5 | 17 | 12.5 | 23 | 54 | 11 | 55 | 0 |
| | 1 | 21 | 25 | 76 | 96 | 100 | 100 | 96 |
| | 2 | 21 | 19 | 62 | 78 | 54 | 72 | 67 |
| | 3 | 21 | 50 | 77 | ND | ND | ND | 63 |
| | 4 | 21 | 50 | 72 | 95 | 100 | 93 | 96 |
| | 5 | 21 | 50 | 51 | 80 | 97 | 88 | 0 |
| | 1 | 28 | 100 | 81 | 100 | 100 | 100 | 96 |
| | 2 | 28 | 37 | 80 | 97 | 100 | 100 | 81 |
| | 3 | 28 | 100 | 80 | 96 | 100 | 100 | 72 |
| | 4 | 28 | 50 | 81 | 100 | 100 | 100 | 100 |
| | 5 | 28 | 150 | 79 | 98 | 100 | 99 | 3 |
| | 1 | 35 | 150 | 84 | 98 | 100 | 100 | 100 |
| | 2 | 35 | 50 | 82 | 95 | 100 | 100 | 49 |
| | 3 | 35 | 100 | 79 | 100 | 100 | 100 | 66 |
| | 4 | 35 | 200 | 79 | 100 | 100 | 100 | 82 |
| | 5 | 35 | 200 | 79 | 98 | 100 | 100 | 21 |
| | 1 | 42 | 300 | 82 | 100 | 97 | 89 | 74 |
| | 2 | 42 | 300 | 81 | 98 | 100 | 100 | 49 |
| | 3 | 42 | 300 | 82 | 100 | 65 | 100 | 65 |
| | 4 | 42 | 200 | 81 | 98 | 92 | 100 | 74 |
| | 5 | 42 | 600 | 81 | 98 | 100 | 98 | 0 |

[a,b,c] See footnotes of Table 4.

TABLE 7

Comparison of CTB-ELISA's with CSFV strain Henken sera

| | | | | CTB-ELISA[c] | | | | |
|---|---|---|---|---|---|---|---|---|
| strain | pig | DPI[a] | NPLA[b] | E1 CSFV | E1-Bac | E1-Bac DIF | E1-Bac dBC-DIF | E2-Bac |
| Henken | 1 | 0 | <12.5 | 0 | 0 | 0 | 0 | 0 |
| | 2 | 0 | <12.5 | 0 | 0 | 0 | 0 | 0 |
| | 3 | 0 | <12.5 | 1 | 0 | 0 | 0 | 0 |
| | 4 | 0 | <12.5 | 0 | 2 | 0 | 0 | 0 |
| | 5 | 0 | <12.5 | 0 | 0 | 0 | 0 | 0 |
| | 1 | 10 | <12.5 | 0 | 0 | 0 | 0 | 0 |
| | 2 | 10 | <12.5 | 3 | 6 | 1 | 1 | 25 |
| | 3 | 10 | <12.5 | 0 | 5 | 12 | 0 | 52 |
| | 4 | 10 | <12.5 | 0 | 6 | 0 | 4 | 27 |
| | 5 | 10 | <12.5 | 0 | 12 | 0 | 0 | 8 |
| | 1 | 14 | <12.5 | 0 | 0 | 6 | 1 | 0 |
| | 2 | 14 | <12.5 | 0 | 54 | 22 | 29 | 10 |
| | 3 | 14 | 50 | 5 | 57 | 67 | 100 | 20 |
| | 4 | 14 | <12.5 | 0 | 7 | 0 | 34 | 0 |
| | 5 | 14 | <12.5 | 0 | 12 | 10 | 9 | 0 |
| | 1 | 17 | <12.5 | 0 | 0 | 0 | 7 | 0 |
| | 2 | 17 | 12.5 | 48 | 73 | 26 | 63 | 53 |
| | 3 | 17 | 75 | 75 | 100 | 94 | 100 | 35 |
| | 4 | 17 | 19 | 7 | 56 | 0 | 60 | 23 |
| | 5 | 17 | 12.5 | 0 | 29 | 0 | 16 | 15 |
| | 1 | 21 | <12.5 | 29 | 0 | 0 | 0 | 0 |
| | 2 | 21 | 50 | 75 | ND | ND | ND | ND |
| | 3 | 21 | 300 | 84 | ND | ND | ND | ND |
| | 4 | 21 | 19 | 36 | 68 | 76 | 78 | 34 |
| | 5 | 21 | 50 | 63 | 83 | 61 | 82 | 32 |
| | 1 | 28 | <12.5 | 0 | 0 | 0 | 0 | 0 |
| | 2 | 28 | 75 | 80 | 92 | 100 | 100 | 92 |
| | 3 | 28 | 600 | 80 | 99 | 100 | 100 | 82 |
| | 4 | 28 | 50 | 58 | 93 | 100 | 100 | 100 |
| | 5 | 28 | 50 | 79 | 99 | 100 | 100 | 100 |
| | 1 | 35 | <12.5 | 22 | 13 | 13 | 0 | 1 |
| | 2 | 35 | 200 | 78 | 95 | 100 | 100 | 82 |
| | 3 | 35 | 300 | 78 | 100 | 100 | 100 | 75 |
| | 4 | 35 | 75 | 75 | 98 | 100 | 100 | 100 |
| | 5 | 35 | 150 | 80 | 98 | 100 | 100 | 97 |
| | 1 | 42 | <12.5 | 17 | 12 | 9 | 0 | 0 |

TABLE 7-continued

Comparison of CTB-ELISA's with CSFV strain Henken sera

| strain | pig | DPI[a] | NPLA[b] | CTB-ELISA[c] | | | | |
|---|---|---|---|---|---|---|---|---|
| | | | | E1 CSFV | E1-Bac | E1-Bac DIF | E1-Bac dBC-DIF | E2-Bac |
| | 2 | 42 | 400 | 79 | ND | ND | ND | ND |
| | 3 | 42 | 400 | 79 | ND | ND | ND | ND |
| | 4 | 42 | 400 | 79 | 98 | 100 | 100 | 100 |
| | 5 | 42 | 300 | 82 | 98 | 100 | 100 | 90 |

[a,b,c]See footnotes of Table 4.

TABLE 8

Comparison of CTB-ELISA's with CSFV strain Zoelen sera

| strain | pig | DPI[a] | NPLA[b] | CTB-ELISA[c] | | | | |
|---|---|---|---|---|---|---|---|---|
| | | | | E1 CSFV | E1-Bac | E1-Bac DIF | E1-Bac dBC-DIF | E2-Bac |
| Zoe-len | 1 | 0 | <12.5 | 0 | 0 | 0 | 0 | 0 |
| | 2 | 0 | <12.5 | 0 | 5 | 0 | 0 | 0 |
| | 3 | 0 | <12.5 | 14 | 4 | 0 | 0 | 0 |
| | 4 | 0 | 19 | 6 | 0 | 0 | 0 | 0 |
| | 5 | 0 | <12.5 | 16 | 35 | 0 | 19 | 0 |
| | 1 | 10 | <12.5 | 0 | 16 | 8 | 3 | 31 |
| | 2 | 10 | <12.5 | 0 | 14 | 0 | 0 | 15 |
| | 3 | 10 | <12.5 | 0 | 10 | 2 | 8 | 24 |
| | 4 | 10 | 19 | 12 | 8 | 0 | 0 | 22 |
| | 5 | 10 | <12.5 | 0 | 27 | 27 | 12 | 24 |
| | 1 | 14 | 19 | 19 | 60 | 18 | 75 | 41 |
| | 2 | 14 | <12.5 | 4 | 36 | 4 | 34 | 10 |
| | 3 | 14 | <12.5 | 19 | 26 | 14 | 23 | 12 |
| | 4 | 14 | 25 | 26 | 91 | 40 | 92 | 39 |
| | 5 | 14 | 12.5 | 0 | 50 | 16 | 41 | 0 |
| | 1 | 17 | 37 | 61 | 96 | 76 | 91 | 64 |
| | 2 | 17 | 19 | 29 | 94 | 62 | 73 | 0 |
| | 3 | 17 | 12.5 | 23 | 41 | 16 | 45 | 4 |
| | 4 | 17 | 37 | 65 | 97 | 82 | 95 | 0 |
| | 5 | 17 | 37 | 48 | 90 | 60 | 75 | 0 |
| | 1 | 21 | 150 | 78 | 95 | 100 | 99 | 84 |
| | 2 | 21 | 19 | 68 | 89 | 100 | 94 | 58 |
| | 3 | 21 | 37 | 60 | 73 | 99 | 77 | 0 |
| | 4 | 21 | 75 | 75 | 92 | 100 | 95 | 46 |
| | 5 | 21 | 37 | 54 | ND | ND | ND | 57 |
| | 1 | 28 | 200 | 75 | 100 | 100 | 100 | 100 |
| | 2 | 28 | 150 | 76 | 100 | 100 | 100 | 89 |
| | 3 | 28 | 75 | 77 | 97 | 100 | 100 | 56 |
| | 4 | 28 | 300 | 79 | 97 | 100 | 100 | 84 |
| | 5 | 28 | 100 | 67 | 100 | 100 | 100 | 80 |
| | 1 | 35 | 400 | 82 | 100 | 100 | 100 | 100 |
| | 2 | 35 | 150 | 72 | 100 | 100 | 100 | 91 |
| | 3 | 35 | 200 | 81 | 98 | 100 | 100 | 60 |
| | 4 | 35 | 150 | 80 | 94 | 100 | 100 | 77 |
| | 5 | 35 | 100 | 79 | 99 | 100 | 100 | 89 |
| | 1 | 42 | 400 | 82 | 93 | 100 | 100 | 100 |
| | 2 | 42 | 200 | 67 | 99 | 100 | 100 | 78 |
| | 3 | 42 | 400 | 83 | 94 | 100 | 100 | 84 |
| | 4 | 42 | 300 | 82 | 99 | 100 | 100 | 86 |
| | 5 | 42 | 150 | 82 | 94 | 100 | 100 | 32 |

[a,b,c]See footnotes of Table 4.

What is claimed is:

1. A nucleotide sequence of the genome of a hybrid classical swine fever virus (CSFV) strain in which at least one nucleotide region selected from the group consisting of the nucleotide regions encoding the amino acid sequences 268–494, 691–750, 785–870, 690–870 and 690–1063 of SEQ ID No. 2 has been substituted in its entirety by the corresponding region of the genome of another non-CSFV pestivirus strain.

2. The nucleotide sequence of claim 1, in which said other pestivirus strain is selected from the group consisting of bovine viral diarrhoea virus (BVDV) strains and border disease virus (BDV) strains.

3. A polypeptide encoded by the nucleotide sequence of claim 1.

4. A recombinant virus, the genome of which is derived from a member selected from the group consisting of full-length DNA copies of the nucleotide sequence of claim 1 and RNA transcripts thereof.

5. A diagnostic composition comprising the nucleotide of claim 1.

6. A diagnostic composition comprising the polypeptide of claim 3.

7. A vaccine comprising the polypeptide of claim 3 and at least a carrier.

8. A vaccine comprising the virus strain of claim 4 and at least a carrier.

9. A nucleotide sequence of the genome of a classical swine fever virus (CSFV) strain in which at least one nucleotide region selected from the group consisting of the nucleotide regions encoding the amino acid sequences 268–494, 691–750, 785–870, 690–870 and 690–1063 of SEQ ID No. 2 has been deleted in its entirety.

10. A polypeptide encoded by the nucleotide sequence of claim 9.

11. A recombinant virus, the genome of which is derived from a member selected from the group consisting of full-length DNA copies of the nucleotide sequence of claim 9 and RNA transcripts thereof.

12. A diagnostic composition comprising the nucleotide of claim 9.

13. A diagnostic composition comprising the polypeptide of claim 10.

14. A vaccine comprising the polypeptide of claim 10 and at least a carrier.

15. A vaccine comprising the virus strain of claim 12 and at least a carrier.

16. A method of distinguishing an animal naturally infected with a pestivirus field strain from a vaccinated animal, said vaccinated animal being vaccinated with a member selected from the group consisting of pestivirus polypeptides and pestivirus strains, said member being mutated by deletion or substitution of the entirety of at least one nucleotide region selected from the nucleotide regions encoding the amino acid sequences 268–494, 691–750, 785–870, 690–870 and 690–1063 of SEQ ID No. 2, said substitution being a substitution by the corresponding region of the genome of another pestivirus species, comprising the steps of:

providing a test sample containing an antibody of an animal to be distinguished;

contacting said test sample with a pestivirus antigen comprising the amino acid sequence which, as a result of the mutation, is absent in said pestivirus polypeptide or pestivirus strain used for vaccination and with an antibody directed against an epitope of said pestivirus antigen, and measuring competition between said antibody in said test sample and said antibody directed against an epitope of said pestivirus antigen.

17. The method of claim 16, in which said pestivirus field strain is a classical swine fever virus (CSFV) strain and said other pestivirus strain is selected from the group consisting of bovine viral diarrhoea virus (BVDV) strains and border disease virus (BDV) strains.

18. The method of claim 16, wherein said pestivirus antigen is a dimerized or multimerized polypeptide and said antibody directed against an epitope of said pestivirus antigen is simultaneously present in an immobilized form and in a labeled form.

19. The method of claim 16, wherein said pestivirus polypeptide is mutated by mutation of the nucleotide region encoding the amino acid sequence 690–1063, said antigen comprises amino acid sequence 690–1063, and said epitope is located between amino acids 785 and 870.

* * * * *